United States Patent
Frutos et al.

(10) Patent No.: US 7,919,436 B2
(45) Date of Patent: Apr. 5, 2011

(54) **SEQUENCES FOR DIFFERENTIAL DIAGNOSTIC OF *EHRLICHIA RUMINANTIUM* AND USE THEREOF**

(75) Inventors: Roger Frutos, Saint Mathieu de Treviers (FR); Conception Ferraz, Agde (FR); Jacques Demaille, Montferrier-sur-Lez (FR); Dominique Martinez, Sauve (FR)

(73) Assignees: Centre de Cooperation Internationale en Recherche Agronomique pour le Developpement (CIRAD), Paris (FR); Centre National de la Recherche Scientifique, Paris (FR)

(*) Notice: Subject to any disclaimer, the term of this patent is extended or adjusted under 35 U.S.C. 154(b) by 760 days.

(21) Appl. No.: 11/577,556

(22) PCT Filed: Oct. 22, 2004

(86) PCT No.: PCT/EP2004/013853
§ 371 (c)(1),
(2), (4) Date: Oct. 5, 2007

(87) PCT Pub. No.: WO2006/045338
PCT Pub. Date: May 4, 2006

(65) Prior Publication Data
US 2008/0305960 A1  Dec. 11, 2008

(51) Int. Cl.
*G01N 1/30* (2006.01)
*C12Q 1/68* (2006.01)
*C12Q 1/37* (2006.01)
*C12N 1/06* (2006.01)
*C40B 40/08* (2006.01)

(52) U.S. Cl. ............. 506/14; 435/6; 435/40.5; 435/259; 506/9; 506/33; 536/23.1

(58) Field of Classification Search ................ None
See application file for complete search history.

(56) References Cited

OTHER PUBLICATIONS

International Search Report and Written Opinion for PCT/EP2004/013853 filed Oct. 22, 2004.

Allsopp M T et al.; "*Ehrlichia ruminantium* Major Antigenic Protein Gene (map1) Variants Are Not Geographically Constrained and Show No Evidence of Having Evolved Under Positive Selection Pressure"; Journal of Clinical Microbiology, Nov. 2001; vol. 39, No. 11; pp. 4200-4203; XP002321870.

Barbet A F et al.; "A Subset of *Cowdria ruminantium* Genes Important for Immune Recognition and Protection"; Gene: An International Journal on Genes and Genomes, Elsevier Science Publishers, Barking, GB; vol. 275, No. 2; Sep. 19, 2001; pp. 287-298; XP004307852.

*Primary Examiner* — Amber D Steele
*Assistant Examiner* — Shannon Janssen
(74) *Attorney, Agent, or Firm* — Alston & Bird LLP

(57) ABSTRACT

The invention provides genes that are unique either to *Ehrlichia ruminantium* strain Gardel or to *Ehrlichia ruminantium* strain Welgevonden, or allelic couples which are present in both strains but whose sequences differ between the two strains, as genetic markers to differentiate between these two strains. The invention also provides diagnostic methods using these genetic markers.

6 Claims, 1 Drawing Sheet

```
                        SEQUENCE LISTING

<160> NUMBER OF SEQ ID NOS: 85

<210> SEQ ID NO 1
<211> LENGTH: 186
<212> TYPE: DNA
<213> ORGANISM: Ehrlichia ruminantium

<400> SEQUENCE: 1
atgagtcaca gttttattga gtttaaacaa atcaattatt acgatattaa cgcaatatat      60
acaatatcat ttgtaacaca tatcaataat tttataccaa aatataagag aaaaattatt     120
ataactctgc ttaatacact aattaacaat attacttctt gtgattttga gtgtaataaa     180
caatga                                                                186

<210> SEQ ID NO 2
<211> LENGTH: 270
<212> TYPE: DNA
<213> ORGANISM: Ehrlichia ruminantium

<400> SEQUENCE: 2
atgtatttag tctatttagt agctggtttt gtggtactat atagtaatta tcgagatata      60
aattatgata aaaaacttgc tattctttat tctaggggag aagatgatga atataaaatt     120
gttcctagga aagagcagaa taatcaatat tattttcata taaaattgta tagtgttaag     180
ttaaatttaa tgtcagatat tgttcaatta gatgttataa tgttaaaagg atttttattat     240 agcaatatgt ttaatgtctt tttattttaa                                       270

<210> SEQ ID NO 3
<211> LENGTH: 630
<212> TYPE: DNA
<213> ORGANISM: Ehrlichia ruminantium

<400> SEQUENCE: 3
atgaaaggat ctttatctgc taaagttatt tctgaaaatc taccattagt agagatggaa      60
aaagcagttc ttagtcctac tgctcgtatt tttctcacta atcataagtt gggacctgtc     120
atggaccttg gaatttatat cttaatacat catagtaatc ttcgtttatt aacgaaggaa     180
aacctttatc ctgctaataa cctaagtaaa attggtaaag tggtgctttg taaacctttg     240
tctataggca atggcataca tacagtacat atgtacttta atgaactcga agctttaaaa     300
gaattcggag gattagaaaa tgctcgcttt acaacagtac gtccggactc ccccttgcat     360
acacatacat ctaaaaaaaa gaaatcatta tttacaaaac gttcagatac ttgctataca     420
ctattatgtg aggaatctta tacagatcca ataataccg aaactgatag tacagtaaaa     480
gcaatatcac ataatgaaga agaagaaggt gcagtaagag gagatatacc acaatatcaa     540 cttttccaatg ccgaagcact aggtcgtggt cttgcttttt tccatgatgt tgcaagtaat     600
tttgaaacat tatgcagaag ataccattaa                                       630
```

<210> SEQ ID NO 4
<211> LENGTH: 828
<212> TYPE: DNA
<213> ORGANISM: Ehrlichia ruminantium

<400> SEQUENCE: 4

```
gtgtgttact taattggtaa ttttatgtta ttcaaataca atcctcaaaa tactaaagaa      60
ttacatgatg cagcttaaa ttgtttacgt catacaagat tatatgcata tagctaccgt     120
tgtataggac atactgaacc taatggaaca ctacatgtat tcataagtaa agataaatca     180
aataatttgt gtttaccaaa agaagggtat tctctattct atatagaatg tagtctatct     240
gataagagag tatctcagaa tcaggaaata agagatatga tgcaagcagt tgtccgccac     300
aaaattaacc gccttgcttt taataaccct cacacgacac ctaccataga tgtaggcatt     360
tatattttaa taaataaaag taaccttaat atgttaacaa agaacatat aacacctacc      420
aacaacatgg acagtgttgg ccatatgata ttatgcaaac ctgtacgtgc agctaatggt     480
ttactctcat tagacttcct attcaatgaa gaagaagctt taaaagagct tggaggatta     540
caaaatgcag tatttacgat aatagaaact acaccaccta ttaccaaaaa atcattattc     600
agaagacatt cactgggtta ttcacaacta tcagaagaac atagtaaacc tgaaacaatt     660
accagtagta ctattacaga gagtataaca agagaagaag cacaatcaag taacaagag     720
gaaggattag aaacacatca gctttccacc aatgtagtaa cacatggtat caattattta     780
actaatgtct cacttgcttt tgaacagcta tgtacaaaat atcattaa                  828
```

<210> SEQ ID NO 5
<211> LENGTH: 303
<212> TYPE: DNA
<213> ORGANISM: Ehrlichia ruminantium

<400> SEQUENCE: 5

```
atggatttaa ataaactaat aaagagatta gtattttcat ttgtaatgat taattttgtt      60
aataggtttt ttagtaatac agaaagtgaa agcttgcatt taagtgatag tttacgacat     120
tattattatt ttctatgttt gtgccatgca gtaatggggt ttattatagt aaatacagat     180
ggatataaca tccttgagga ttttatgttc tcagaacaaa tcgtaggtag agaaaatgca     240
gaaatgcttt caatatcaga tacagagggg ggggggggag agcttagtag aagaaaattc     300
tag                                                                   303
```

<210> SEQ ID NO 6
<211> LENGTH: 225
<212> TYPE: DNA
<213> ORGANISM: Ehrlichia ruminantium

<400> SEQUENCE: 6

```
ttgtacatag tatgtcttta tataaaagta agaattgatg attctactga tgttattact      60
tataactcta aaaaatat gtgtaaatta caattaactc agaaaagaa tagatcattt        120
atatatttgg ttaacagata ctatcataaa tcagaatata ggcttaccac actttcagtt     180
caatcttata gcaaattaga gcaactttat aacaatatcc agtaa                     225
```

<210> SEQ ID NO 7
<211> LENGTH: 1266
<212> TYPE: DNA
<213> ORGANISM: Ehrlichia ruminantium

<400> SEQUENCE: 7

```
atgggtattg ataattatga tggtgaaact tcaaaaacat taactatgca ggagttatat      60
aaagctcttg gtacaatgtt caaggaggca tatagccaat ttgcaggtaa ggatactaaa     120
aaagattcaa cggtgttgga tgatcagggt gatctatcta aaactacagt tccagtagca     180
catgaggatg aatcaagtgg tgaaatctct catgaagaag gcatagagt tttaggagaa      240 gatacacatg aagtacaaca tgcagttcca gtagcatatg aacatgaatc aagtggtgaa     300
atctctcatg aagaagacca tagggtttta ggagaagatg aagcacatga tatcgaacat     360
acagttccag tagcacatga gcatgaatca agtggtgaaa cctctcatgg agaaaaccat     420
agagttttag gagaagatga agcacatgat atcgaacatg cagttccagt agcacatgaa     480
catgaatcaa gtggtgaaat ctctcatgaa gaagatcata gagttttagg agaagatgcg     540
catggagtac aacatgcagt tccagtagca tctgagcatg aatcaagtga tgaaaaacct     600
tatgaagaag accataaagt tttaggagaa gatgaagcac atgatatcga acatacagtt     660
ccagtagcac atgagcatga atcaagtggt gaaacctctc atgaagaagg cataaagtt      720 ctaggagaag atgcacatga agtacaacat acagttccag tagcacatga ggatgaatca     780
agtagtgaaa cctctcatgg agaagaccat aaagttctag gagaagatgc gcatgcagta     840
caacatacag ttccagtagc acatgaacat gaatcaagtg gtgaaaaatt tgatgagaaa     900
gaccataaag tttcagaaga acctaagcat atatcaagtg gtgaagtatt ccagaaagaa     960
gaacaaccta ctgttccaat agaacctgtg ttagggaaga ctccagtact taaagtacaa    1020
gctagtcata cacatgagcc tattgtgata caatattact tatgtaatgt agaaaatggg    1080
aaagctgttt gtggggttca agaggtaaca ttacttggta taagtgctaa tcacaatgat    1140
gttatgaaat attatgatgt aaatacctct tctttaaaca actgtttgca tcatcatggt    1200
ggacatagta atgatatgca tcacactcat cattgtcctt gtaaccatga aattacattt    1260
gcttaa                                                               1266

<210> SEQ ID NO 8
<211> LENGTH: 1176
<212> TYPE: DNA
<213> ORGANISM: Ehrlichia ruminantium

<400> SEQUENCE: 8
atgggtattg ataattatga tggtgaaact tcaaaaaaat taactatgca agagttatat      60
aaagctcttg gtacaatgtt caaggaggca tatagccaat ttgcaggtaa ggatgctaaa     120
aaagattcaa cggtgttgga tgatcagggt gatctatcta aaactacagt tccagtagca     180
catgagcatg aaccaagtga tgaaaaacct tatgaagaaa tcatcaagt tctaggagaa      240 ggtgcgcatg gagtacaaca tgcagttcca gtagcatctg agcatgaatc aagtggtgaa     300
acctctcatg aagaagacca tagagtttta ggagaagatg aagcacatga tatagaacat     360
acagttccag tagcatctga gcatgaatca agtagtgaaa cctctcatga agaagagcat     420
aaagttctag gagaagaaga tgcgcatgaa gtacaacata cagttccagt agcatctgag     480
catgaatcaa gtggtgaaac ctctcatgaa gaagaccata agttctagg agaagaagat      540 gcgcatgaag tacaacatgc agttccagta gcacatgaac atgaatcaag tggtgaagcc     600
tctcatgaag aaggacataa agttctagga agaagaagatg cgcatgaagt acaacataca    660
gttccagtag cacataaaca tgaatcaagt ggtgaaacct ctcatgaaga aggacataaa     720
gttctaggag aagaagatgc gcatgaagta caacatacgg ttccagtagc acatgaacat     780
gaatcaagtg gtgaaaaatt tgatgagaaa gaccataaag tttcagaaga acctaagcat     840
```

| | |
|---|---:|
| atatcaagtg gtgaattatt gccggaagaa gaacaaccta ctgttccaat agaacctgtg | 900 |
| ttagggaaga ctccagtact taaagtacaa gctagtcata cacatgagcc tattgtgata | 960 |
| caatattact tatgtaatgt agaaaatggg aaagctgttt gtggggttca agaggtaaca | 1020 |
| ttacttggta taagtgctaa tcacaatgat gttatgaaat gttatgatgt aaatacctct | 1080 |
| tctttaaaca actgtttgca tcatcatggt ggacatagtc atgatatgca ccacactcat | 1140 |
| cattgtcctt gtaaccatga aattacattt gcttaa | 1176 |

<210> SEQ ID NO 9
<211> LENGTH: 3252
<212> TYPE: DNA
<213> ORGANISM: Ehrlichia ruminantium

<400> SEQUENCE: 9

| | |
|---|---:|
| ttgcataaaa ttatgcctac atcacttaaa accatagtta ctgatagtaa actaagatct | 60 |
| agtattattg atggatctag tgttaatttt tttaaaaaag gtaacattat tttttctgta | 120 |
| tattatacaa gaaataatgt tgatggatat gatgtaatat gtgagattca acatggtgct | 180 |
| tctatttatt atatgaaaat taatgatcat gcaattattg atcgtcgggc aacgaattat | 240 |
| ccaccagaga tgttatttgt aaagaatagt aatgatgatt tgatatttat tgttattcct | 300 |
| gaagaaagta aaggtagtaa agctttagtt atcaaaaatat ataagataaa ttataatcct | 360 |
| aatgtgtctt tatcccaatt acatgattta caattaatta gttgcaataa ctatctcaaa | 420 |
| gaagaagtga aatatcctgt tattttacat caggatacgg ttggtaggat tgttgttatt | 480 |
| gcaagagtag ataatgacta tcgaggtgat gttacagata gattgtatgt gatgtggcaa | 540 |
| ttgagatatc ataatagtag atttgaaatt ataggtttaa gtaatgggta tagacgattt | 600 |
| aatgctgcct acttatttaa gcattctggt tatattaatc gtggaaaatg tcatgataga | 660 |
| ctaattgtta aattaggatc ggatagtttt ataaattttc tttatgttgg gaaacatatt | 720 |
| tctagagatt acaatttttt ttctagtata tatgatttat ctataaatta taatatgcat | 780 |
| cttaatccag aagaatgttt ggtgggttct ttttatggtt gtaatgctag tagtggtagg | 840 |
| agatataata ttcctaatag ctgcattcat gttattgata ttttttcgtga tgatgggaat | 900 |
| gtatatatag catatattgg tactgtattt aatagtacat ttaagaataa aaagcagttg | 960 |
| gttattgttt atactatggg tgatgaacaa tcgcatgtgt atgattttat gcagattaca | 1020 |
| gaagatatta gtgccatata tataaattct actgaaaata ttttagcaat aacgactatg | 1080 |
| ggaagtgatt atcttgtaaa atatgagatt tcaaaattac agttaaaatt agggattgtt | 1140 |
| gatcatgttg atgttataaa aattccacgt aatgtagtga aaatatattgc taattttaca | 1200 |
| tatgttgttg atacaatttt agggtttgat agtgttgaac atattaatat tcgtaatgta | 1260 |
| ttagctacaa aatcaactgt taattataag gtatctcagt ttttttttaaa tattagagaa | 1320 |
| atggaatttg gtgattatt taagagttgg agtggtgaat ataatgactt gttaataggt | 1380 |
| tatactatgc ctgctagtta tggtgtaaat tatactacag aatatttaag cgatgttata | 1440 |
| actgtttcag gtaatgcagg ttttgtagag aagttcatat caactagtaa aatgggtgat | 1500 |
| gtatttaaga ttacagataa cttaattaat tatactagtg taaaccctac taatcatatg | 1560 |
| gcacatatga cattgcaatc aaaattgtca gatggtgagg gtattacaga gcgtgcgggt | 1620 |
| aataaatcag ataattctgt aagtgaaagt ttagctacag gattggttct tactagtaaa | 1680 |
| aatgatgatt tgtttaaaag tacagctagt cctattaatc atgcttttgg ttatgtaata | 1740 |
| aagcctactc gccatgtaac gcatgtaaca ttggaatcga agtcaccata tggtaaagag | 1800 |

```
gttgtgaggc atatgaatcc taaaacggat aattctatac atacaagttc aataccaaga    1860
tcagtactga ctagtagaag cgatgatgta ttgaaaagta cagctagtcc tattaatcat    1920
gcttttggtt atgtaataaa gcctactcgc catgtaacgc atgtaacatt ggaatcgaag    1980
ttaccatatg ataaagaggt tgtgaggcat atgagtccta aaacggataa ttctatacat    2040
acaagttcaa taccaagatc agtactgact agtaaaagcg atgatgtatt gaaaagtaca    2100
gctagtccta ttaatcatgc ttttggttat gtaataaagc ctactcgcca tgtaacgcat    2160
gtaacattgg aatcgaagtt accatatgat aaagaggttg tgaggcatat gagtcctaaa    2220
acggataatt ctatacatac aagttcaata ccaagatcag tactgactag tagaagcgat    2280
gatgtattga aaagtacagc tagtcctatt aatcatgctt ttggttatgt aataaagcct    2340
actcactatg taacgcatgt aacattggaa tcgaagtcac catatggtaa agaggttgtg    2400
aggcatatga tcctaaaac ggataattct atacatacaa gttcaatacc aagatcagta    2460
ctgactagta aagcgatga tgtattgaaa agtacagcta gtcctattaa tgatgctttt    2520
ggttatatga acctgctag ttctattgta gtatcattag gtgatactga tgtttcaaag    2580
caagtgaaaa gtgttagtaa tgttccagta tatcttactc ctacagtaag atcagtatta    2640
gtaggtgatg cgtatcatgt atctggtagt gaaaagata gtattggaca tgaacaagat    2700
ttgggtcatg gtgatgttag taccgatgtt gtattgaaac taatgagtga taatgtatca    2760
aacaatatta gtaggcatgt aaatgattct ttagctataa acataagat attaggtaaa    2820 aaaataaagt ataatataag gcgtagtact gttagatctg ctgttaatat tcgcaataaa    2880
agtacagtga gtacaagata tacatctcat ggcatacaag aggctaataa tatgaatgtt    2940
acattgttta atcctacaca gcataatatt agtagttata atggtagttt attaaatagt    3000
aattctgctt ttaatactga aagttctgtt gattataaag tagtaattgc agtaatatct    3060
agtatactgc ttatcttttt attattaggt ggatttaaat gtataaagtg gtatttagca    3120
aagttgaata aagaaggat gtctaataat gaacagggat ttgtgatttt taatttggat    3180
agtattcaaa gtagtgtttc tggtgtgcaa gtgacagaag gtaccacatc tcgaatagag    3240
agtctattct ag                                                       3252
```

<210> SEQ ID NO 10
<211> LENGTH: 2856
<212> TYPE: DNA
<213> ORGANISM: Ehrlichia ruminantium

<400> SEQUENCE: 10

```
ttgcataaaa tcatgcttac atcacttaaa actacagtta ctgataataa actaagatct      60
agtattatta atggatctag tgttaatttt tttaaaaaag gcaacattat tttttctgta     120
tattatacaa gaaataatgt taatggatat gatgtaatat gtgagattca acatggtgct     180
tctatttatt atatgaaaat taatgatcat gcaattattg atcgtcggac aacaaattat     240
ccaccagaga tgttatttgt aaagaatagt aatgatgatt tgatatttat tgttattcct     300
gaagaaagta aaggtcgtaa agctttagtt atcaaaatat ataagataaa ttataatcct     360
aatgtgtctt tatccaaatt acatgactta caattaatta gttgcaataa ctatctcaaa     420
gaagaagtga aatatcctat tattttacat caggatacgg tggtaggat tgttgttatt     480 gcaagagtag ataatgacta tcgaggtgat gttacagata gattgtatgt gatgtggcaa     540
ttgagatatc ataataatag atttgaaatt ataggtttaa gtaatgggta taggcaattt     600
aatgctgcct attattttaa gcattctggt tatattaatc gtggtaaatg tcatgataga     660
```

```
ctaattgtta aattaggatc ggatagtttt ataaattttc tttatgttgg gaaacatatt      720
tctagagatt acaatttttt ttctagtata tatgatttat ctataaatta taatatgcat      780
cttgatccag aagaatgttt ggtgggttct ttttatggtt gtaatgctag tagtggtagg      840
aaatataata ttcctaatag ctgtattcat gttattgata ttttttcgtga tgatgggaat     900 gtatatatag catatattgg tactgtattt aatagtacat ttaagaataa aaagcagttg      960
gttattgttt atactatggg tgatgaacaa tcgcctgtgt atgattttat gcagattaca     1020
gaagatatta gtgccatata tataaattct actgaaaata ttttagcaat aacgactatg     1080
ggaagtgatt atcttgtaaa atatgagatt tcaaaattac agttaaaatt agggattgtt     1140
gatcatgttg atgttataaa aattccacgt aatgtagtga aaatattgc taattttaca      1200 tatgttgttg atacagtttt agggtttgat agtgttgaac atattaatat tcgtaatgta     1260
ttagctacaa atcaactgt taatgataaa gtatctcagt tttttttaaa tattagagaa      1320
atggaatttg gtgatttatt taagagttgg agtggtgaat aaatgactt gttaataggt      1380 tatactatgc ctgctagtta tggtgtaaat tatactacag aatatttaag cgatgttata     1440
actgtttcag gtaatgcagg ttttgtagag aagttcatat caactagtaa aatgggtgat     1500
gtatttaaga ttacagataa cttaattaat tatactagtg taaaccctac taatcatatg     1560
gcacatgtga cattgcaatc aaaattatca gatggtgagg gtattacaga gcgtgcgggt     1620
aatagatcag ataattctgt aagtgaaagt ttagctacag gattggttct tactagtaaa     1680
agtgatgatt tgtttaaaag tacggctagt cctattaatc atgcttttgg ttatgtaata     1740
aagcctacta tccacgtaac gcatgttaca ttgcaaccga agtcaccata tggtaaagag     1800
gttgtgaggc ataaatcc taaaacggat aattctatac atacaagttc aataccaaga      1860
tcaatactga ctaatagaag cgatggtgta tttaaaagta cagctagtcc tattaatcat     1920
gcttttggtt atgtaataaa gcctactcgc catgtaacgc atgttacatt gcaaccgaag     1980
tcaccatatg gtaaagaggt tgtgaggcat ataaatccta aaacggataa ttctatacat     2040
acaagttcaa taccaagatc agtactgact agtaaaagct atgatgtatt taaaagtacg     2100
gctagtccta ttaatcatgc ttttggttat atgaaacctg ctagttctgt tgtagtgcca     2160
ttaggtgata ctgatgtttc aaagcaagtg gaaagtgtta gtaatgttcc agtacatctt     2220
actcctacag taagatcagt attagtaggt gatgcgtatc atgtatctgg cagtgaaaaa     2280
gatagtgttg gacatgaaca agatttgggt catggtgatg ttagtactga tgttgtattg     2340
aaactaatga gtgataatgt atccaacaat attagtaggc atgtgaataa ttctttagct     2400
ataaaacata agatattagg tagaaaagta aagtataata taaggcgtag tactgttaga     2460
tctggtgtta atattcgcaa taaaagtaca gtgagtacaa gatatacatc tcatggcata     2520
caagaggcta ataatatgaa tgttacattg tttaatccta cacagcataa tattagtagt     2580
tataatggta gtttattaaa tagtaattct gcttttaata ctgaaagttc tgttgattat     2640
aaagtagtaa ttgcagtaat atctagtata ctgcttatct ttttattatt aggtggattt     2700 aaaatgtataa agtggtattt agcaaagttg aatagaagaa ggatgtctaa taatgaacag     2760
ggatttgtga tttttaattt ggatagtatt caaagtagtg tttctggtgt gcaagtgaca     2820
aaaggtacca catctcgaat agagagtcta ttctag                               2856
```

<210> SEQ ID NO 11  
<211> LENGTH: 1836  
<212> TYPE: DNA  
<213> ORGANISM: Ehrlichia ruminantium

<400> SEQUENCE: 11

```
atgttattca aacccggttc acccgttgcc aagattacag aatctctgca taaatcagtt      60
atatatgagt tgaatagagt accagaaata catcttaata catgtcattg tataggagct     120
acaataggta caaaacttga tatctggatt gataataagt caggtcatcg gtgtactcca     180
gtaggaacat cttttatttct tatggaatgt attatacccca ctgctgtaat aaatcatcca    240
cgtaatatat ctttacaaaa gttgacacaa gtattgtcta gtcgcttttc aagaacacaa     300
ccacttaagg ctgatgtata ttttattgta tcagaggaag aattcgagaa tttcagaagt     360
acagtatccc ctttatgtag tatgggactt aatgaacttt tacctgttta atatattggt     420
aaattcggag cattttgcgt atgtaggcca aaaagtatag gtaatagagg tgtagatgta     480
ctatttgatg aatacaaagc tttaagggtt ttaggaggtc tagaggattc taattttttt     540
aaaacacccct tatcaacctc taataccaca aacgtaata caaaacaaag cacagcaaat     600
aatagagaac aaaaatttgt agtaactggt aagaaaattc aaagcaaaat acaaagtata     660
aaacatctac ataaaatatt ttctagatct tctactacac aatgttcacc tttaagtaca     720
ccagtcaata ctaaaacaca acataatata gaagaaaaaa cagcaagtag tacgcaagaa     780
ccaaatatcc aaaaggttat agtaactagc aatcaaccta atagagaaaa aacacaactt     840
atatgtacaa agtttcctga ggctccaaaa tatccatctt taaatcaaag acaagagaca     900
ggaggcaagt atttagaaca gcgtctatca aaaagtacag cagatagtac gccatttaca     960
caaaaggta caacgattc tcaacaagtt gttagaccaa aaacacaatt tgcatctagt     1020
ccttttttatt tttatcaaga acagccactt ttaactacaa acattcatc ttcaaatcaa    1080
agacaagaga caggaggcaa gtatttagaa cagcgcctat caaaaagtac agcagatagt    1140
acgccattta cacaaaaagg tacaacagat tctcaacaag ttgttagacc aaaaacacaa    1200
tttgcatcta gtccttttta ttttatcaa gaacagccac ttttaactac aaaacattca    1260
tcttcaaatc aaagacaaga gacaggaggc aagtatttag aacagcgcct atcaaaagt    1320
acagcagata gtacgccatt tacacaaaaa ggtacaacag attctcaaca gttgttaga    1380
ccaaaaacat ttgcatctag ttcttttttat aaagaatcgg cacttgcaat tacaaagcat    1440
ccatcttcaa atcaaagaca agaggcaaca acaagcatt tagaacagcg tccatcaaca    1500
aaaagtacag tagatcctca acaagttgtt aggccaaaaa cacaatctgc atctagtcgt    1560
gtttataaag aacagggact tccaactaca aaacataaaa tattaagtgc tataaaagaa    1620
tctacagata gtagtacatc agttaataca ttaagttctg aagaagattt acggtttta    1680
aatgtagatt attctagtag ttgtgaaata ttatacgata ctttcagaga atcttataga    1740
gttagtgctt taccaacatc acctctcatc ccatcacatc aacttgaaga tgatgtattt    1800
gttgaagatg gttatcctcg tgcatcttat ctttga                              1836
```

<210> SEQ ID NO 12
<211> LENGTH: 1659
<212> TYPE: DNA
<213> ORGANISM: Ehrlichia ruminantium

<400> SEQUENCE: 12

```
atgttattca aacccggttt acccatttcc aagattacag aatctctgca tagatcagtt      60
atacgtgagt tgaatagagc gtcagaaata catgttaata cgtgtcattg tataggagct     120
acaataaata aaaaaactct taatatctgc gttgataata agccaggtaa tcggtgtact     180
ccagtaggaa catctttatt tcgtatggaa tgtattatac ccgctcctgt aataaataat     240
```

```
ccacgtaata tatctttaca aaagttgaca caagtattgt ctagtccttt tttaataaca      300
ctagaaccac ttaaggttga tgcatatttt attgtaccag aggaagaatt aaagaatttc      360
atagatttag taaaacattt atctagtatg ccacgtgaag gacttttacc tatttataat      420
attggtaaat tcggaacatt ttccttatgt aggccaaaaa gtataggtaa tagagatgta      480
aggcatgatg taccatttga cgaattcaaa gctttaaata ttttaggagg tctagaggat      540 tctattttt ttaaaacacc ctcatcaatc cctgatatca caaaacgtaa tacaaaacaa       600
agcatagcag atagtaaaca acaaaaagtt gtagtaactg gtaaggaaat tcaacacaaa      660
atacaacata taaaaaaaat gttttctaga gtttctacta cacaatgttc accttcaagt     720
acaccagtca gtgctcaaat gacacataat atagaagaaa aaacagcaag tagtccgcaa     780
aagccagcta tccaaaaggt tatagtaact agcaaacaac ctcgtaaaga agaaatacaa     840
tttatatata caaagtttcc tgaggctcca gaagaacatt catcttcaaa tcaaacacaa     900
gagacaacaa gcaagcattt agaacagcat ctatcaaaaa gtatagtagg tggtgcgcca     960
cttatacaaa aggtacagt agatcctcaa caagttgtca gaccaaaaac atttgcatct     1020 agtcctttt ataagaatc gacacttcca actacaaaat atccatcttc aaatcaaaca     1080
caagaaacag caagcaagca tttagaacag catccatcaa aaattacaca aaaaggtaca     1140 ataaccttc aacaagttgt tagaccaaaa acacaatttt catctagtcc tttttataaa     1200
gaacaggtac ttccaaatat aaaacatcca tcttcaaatc aaagacaaga gacagcaaac     1260
aagcatttag aacagcgtac attaaaaaaa agtacactag gtagcatgcc gccatctata     1320
caaaaaggta caatagatcc tcaacaagtt gttaggccaa aaacacaatc tgcatctagt     1380
cctttttaca aagaatcgac acttccaact acaaaacatc aaatgttaag tgttatagaa     1440
gaatcgacaa atagtagtgt accaattaat acattaagtt ctgaagaaat accacggttt     1500
ttcagtgtag attattttag tagttataaa gtattgtacg atacttacaa agaatcttat     1560
aaagttgata ctttaccaac agcacctctc gtcccatcat gtcaacttga agatgatgta     1620
tttgttgaaa atagtaatcc ccatgtatct ttgaattaa                             1659
```

<210> SEQ ID NO 13
<211> LENGTH: 3570
<212> TYPE: DNA
<213> ORGANISM: Ehrlichia ruminantium

<400> SEQUENCE: 13

```
atgccactta cttttgatct atatgcatat gaaagaaaat taaattttct tctatgcaat       60
gctgtaaatt ctaatcctaa gttagttaat gtaataaatg tagtttgtgt aggatatact      120
gatgaaaata atcagttatt acttgctact gactacaaca ttccaccaga attcaccct       180 attcctagaa tcaatccctt attttcgtata atgctaata taaaaactag cattataaca      240
aattctttta gattatctca agagtttgct ttaacacaag aggagctaaa taatggtaat     300
gttaagtgtg aaatgtattg tttagtaggt aatgaaaatc ttgatgattt tactaaaata     360
tgtagtaagc ataagtaag atataaaaat ctaacaacaa tttccaagaa tatttacaca     420
caattattta cagcagatat attaaaattt cctattaaca tagaacatgc tctatcaaat     480
atagcaaatt taaatgcaca atatatatat gcatctgatc taataaaatga atctgatcta     540 ataaatgcgt ctgatctaat aaatgcgtct gatctaataa agaagaaaa aattaagaat       600 attagaggaa gtactagtat attatatgat gcaatatgca gtacatatgc aactaatgat      660
taccatgtac tttctgtaaa atgcatagga tatactcata ataatcgaca actcatagtt     720
```

```
cacactcaat gtccagagaa ccttttacct atacctcaaa gtaactctct atttattgta      780
tgtgttgata tatcaccaga tatcataaca aataatgaaa atttatcctc tacttttgaa      840
ttaacagaaa gtgaaagtaa acaaagtact atcaattgtg caatgtactg tttagttaat      900
gatgaacaac ttggaagttt tactcataaa tgtaatacta caaataataa accaaagctt      960
caagatatta ttcaattttg ttctgtaata tgtataacac tcaatacaga aagaatatca     1020
tcattacaaa ttagcgaaga agagctaata aatagtgtag gaataggtga tgtaacattc     1080
agaaattta gtgatctacg taaggaaaaa cttaagaaaa tacagcaaat aaagaatgaa      1140
ctatgtagtg caatatgcag tatatatgca gctaataact accatgtact ttctgtaaaa     1200
tgcataggat atactcataa taatcaacaa ctcatagttc acactcaatg tccagacagc     1260
cttttaccta tacctcaaag taactctcta tttattgtaa atgttgatgt atcaccagat     1320
atcataacaa ataataaaaa attatcctct acttttgcat taacagaaag tgaaagtaag     1380
caaagtactc tcaagtgtgc aatgtactgt ttagttaatg atgaacaact tgaaagtttt     1440
actcataaat gtgatattac aaataataaa ccaaggcttc aagatattat tcaattttgt     1500
tctgtaatat gtataacact caatacgaaa agaatgttat cattacaaat tagcgaagaa     1560
gagctaataa atagtgtagg aataggtgat gtaacattca aaaattttag tgatctacgt     1620
caggaaaaat ttaataaaat acagcaaaca aataatgaac tatgtagtgc aatatgcatt     1680
tcacctgaag aaaataaaat aattgatata aatgcgtag gacacactac cgctaagaat      1740
aaattagtag ttcatactga atgtccacta gctcttcttc ctacacctca aggtgattca     1800
ttattttcta tactgatggc tataccatac gctattatag caaataatgc catattatct     1860
cctgctttta aagtagtaaa aaatgatctt ggtattaata gtaattatat tttatgcact     1920
gcatactgtc tagtaactaa gcatgatctt caagatttta ctaatgaagt gtcatcggat     1980
ggtgcaatag gtgatagtat acaacaaaaa cgtcaaaaat ttgaaagtat cattaaatta     2040
tgttctgtaa aatgtgtaac attacataca caagaaatac tgtcattaaa tattagtcaa     2100
aaagaactaa tcaacgatat agggttatgt aatgcaactt tcaaatattt aagtaatctg     2160
catcaagaaa agattgatct acttaaacaa gtaaataata aattatgtcg tgaaatatgt     2220
aataaactta ggaaacataa aacacaatat ataagatgta taggaaatac tgttaatact     2280
aaattagtag ttaccactca gtgtccacga gatcttcttc cttttcctaa aggtcaatct     2340
ttattcatta taaggataaa tatatcacct aacattatat tacacagtaa aacactacgt     2400
aatacattta aattaacaac aagtgaaaga tcagatcatc acattaaatg tgatatgtat     2460
tgcctagtat atgaagaaaa tattaagagt tttattgatg tatgtgatga tccaaataag     2520
ccatatattg aagagttaat tcaatattgt tctgtaaaat gtataaaatt gtatacacaa     2580
gaaatgttat cattaaacat tagtgaagaa caactaatca acgatatagg gttatgtaat     2640
gcagaattta aatatgttga agtaaacat ataattgaat cagtattgga cgcatttaat      2700
tatatcgaaa tacaagcaaa taactcctca tgcggaattt tgcctacact tgtgctttta     2760
tataaaaaag attttctcat caaaaagata cgttgtatag gtaatactat agatcctgaa     2820
caaggattaa caatttatcc ttctagtata tacccaaagg aattcttacc aactgcccaa     2880
ggtacatctt tattttaat acgaactagg atattaactg aagttatatt aagtactcct      2940
gaactagtga atgtacatat tctaaatgat gaagaaatgt tgaataagta tttattatgt     3000
gatatatatt gcctagtaga tgagaaaaac cttagaaat ttaagaatct tgtacaaaa       3060
gcaagaaatc tttcagatat gataattaca tgtggtgtaa agtatgttag gatacataca     3120
```

| | |
|---|---|
| aaagattcta aaagatttcc atttgatgaa gcaaaggtat taaaacactt aggaggtata | 3180 |
| gacggaagat atctcgacga aggagatttt gacaaattac ttagttctgg actttatacc | 3240 |
| aaatcatcaa gtaagtcttc atcaacaata tcgactgaag aagaatcaag tacacaagaa | 3300 |
| gggacccata taaaacgtag tttaagatca acattattaa aaataagaaa acaaatagga | 3360 |
| cctgagtctt catcatctgc tacattctca agtggagatg agttagattc agaagacgaa | 3420 |
| cttcaagaaa gaagacaaaa aagacgtgca agattagcaa gactacaaca tgaagaatca | 3480 |
| caaacaacaa aaagtaaaac aggaataggt ggtatcttgt ctgatcaaga agtttcacat | 3540 |
| cataaatctc aaagtaaaga tttagattag | 3570 |

<210> SEQ ID NO 14
<211> LENGTH: 873
<212> TYPE: DNA
<213> ORGANISM: Ehrlichia ruminantium

<400> SEQUENCE: 14

| | |
|---|---|
| atgccactta ctttcgatct atatgcacat gaaaaaagat taaatcttct tctatgcaat | 60 |
| gctataaatt ccgctgctaa tctagttaat gaaatagata tatcttgtgt aggatatact | 120 |
| gatgaaaccg gtaaattagt ggcttttatt gaccctaaca ttccactaaa cttattccct | 180 |
| attcctcaaa atctatcctt atttcgtata agtggtacta taccaattac cattataaca | 240 |
| aattctaatt ctcaagaatt atctaaagag tttgttttca cagaaggtga ataaatagt | 300 |
| ggccttgtta gtgtgaaat gtattgttta gtaggtaatg aaaatcttga tgatttact | 360 |
| gaaatatgta gtaatcctaa aataggatat gaaaatttaa taaaaatttc caataatatt | 420 |
| tacacacaat tatttacaga agatatatta aaatttccta ttaacataga acatgctcta | 480 |
| tcaaatatag caaatttaaa tgcagaatat atatatgcat ctgatctagt aaggaaagaa | 540 |
| aaacttaagc agcttaaaga aagaaatgat gatttatgta atgcaatatg ccatgcatgt | 600 |
| aatgaggaga atgtaacttc tgtaaaatgc ataggacata ctcctgacag taatcaactc | 660 |
| acagttcata ttaatgtcc agaaagcctt ttacctatac ctcaaagtaa ctctctatt | 720 |
| cttgtcgaga tgagtatatt acctaatgtt atagggggca atcaaatatt atcctctact | 780 |
| tttgaattaa cagaaagtga atgtaaaaaa ggtgctctca attgtacaat gtactgttta | 840 |
| gttagtaagg agaaacttaa aaaattttac tga | 873 |

<210> SEQ ID NO 15
<211> LENGTH: 1740
<212> TYPE: DNA
<213> ORGANISM: Ehrlichia ruminantium

<400> SEQUENCE: 15

| | |
|---|---|
| atggctatac cacacactat tatagcaaat aatgccatat tatcttctac tttaaagta | 60 |
| gtaaaaaatg atcttggtat tgatagtgat tatattttat gcactgcata ctgtctagta | 120 |
| actaagcata atcttcaaga ttttactaat gaagtgtcat cggatgatgt aatagatgat | 180 |
| actacacaac aaaaacgtca aaatttaaa atatcatta aattatgttc tgtaaaatgt | 240 |
| gtaacattac atacacaaga aatgttatca ttaaacatta gtgaagaaga actaatcaac | 300 |
| gatataggt tatgtaatgc aactttcaaa tatttaagta atctgcatca agaaaagatt | 360 |
| gatatactta gacaagcaaa taataaatta tgtcgtgaaa tatgtcttaa acttaataaa | 420 |
| catcaaacaa actatataag atgtatagga aatactgttg ataatcaatt aatagttacc | 480 |
| actcagtgtc cacgagatct tcttcctttt cctaaaaatc aatctttatt cattataagg | 540 |

```
ataaatatac cacctaacat tatattacac agtaaaatac taaataatac atttaaatta      600
acaaaaagtg aaaagaaga ttattacatt aaatgtgata tgtattgcct agtatatgaa       660
gaagatatta agagttttat tgatgtatgt gatgatttag ataagccata tattgaagag      720
ttaattcaac attgttctgt aaaatgtata aaattgtata cacaagaaat gttatcatta      780
aacattagtg aagaagaact aatcaacgat ataggggttat gtaatgcaga gtttaaatat    840
gttgaaagta gacagataat tgaatcagta ctagacacat ttgagtatat cgaaatacaa     900
gcaaataaac tcctatgcag aattttgcct acactttgtg ctttatataa aaagattttt      960
ctcatcaaaa agatacgttg tataggtaat actatagatc ctgaacaagg attaacaatt     1020
tatcctccta gtatattctc aaaggaacac ttaccaactg ccaaaggtac atctttattt     1080
ttaatacgaa gtaggatgtt aactgaagtt atattaagta ctcctgaact agtgaatgta    1140
cataatctaa gtgatgaaga aatgtcgagt aagtatttat tatgtgatat atattgccta      1200
gtagataatc aaaacattaa tctatttaag aatctttgta caaagacaag acagttttct      1260
gatgttgtaa ttcatgtga tgtaagatat attaggatat atacaaaaga tgctagaaaa       1320
ttcccattta atgaggcaag tgtattaaaa caattaggaa atataaaagg aaaatatctc     1380
aatgaacaag actttaaagc attagttagt tctggacttt atactaaatc agcaagtgaa      1440
tcttcatcag cagtatcaac tgaagaagaa tcaattatac aacaagaact ccatgtaaaa      1500
cagagtttaa aatcaagatt atcacaaata agaaaacaac taacacctga ttcttcatca    1560
tctaatacag tatcaagtga agatgatata gatacaccag cagaaattaa aagaaaaaga    1620
gaagcaagac gtttaaaatt agcaaaatta caacaagaag aatcacaaac aacaggaata    1680
ggtatgttgt ctgatcaaga agtttccacat cataaatctc aaagtaaaga tttagattag    1740
```

<210> SEQ ID NO 16
<211> LENGTH: 6903
<212> TYPE: DNA
<213> ORGANISM: Ehrlichia ruminantium

<400> SEQUENCE: 16

```
atgtataatt ttattaaaaa tcattttata aaattattgt tacttttatt gatgactgca      60
tgtgaatcaa atcagcatcc ggtgcctaga tgtataccag ctgatgtatt tactgaaggc     120
aggacaactt ctgtgtctgc atattttgat cctacttctg aaaattttat gtctgacaat    180
aaggttttag gaaattctgt tgaagataat caggtagtgc ggtggaaata tactggatat     240
gtaacaaatg gtcatccgat tgtattaagg gctgaaggga tgtggacttc atgggctaag    300
aaaagtaata atgtaactga agttcaaaca aatactacag attatggaga tgatgatgta    360
gatcgttata atgctatctt ggcagttgat agagtttgtg gtccttataa aaaaatagag    420
aagcattttt ctaatggtac aaatcaatgt aaagtatcat gtgaaatgat ttctggagtt    480
caagacaatt tagagacagg aacatatggt ccaccttgtt ggtttagaaa tggttatggt     540
gcgtatctat tattcaaaag accagaagat cctgaaccaa atgaaacgat tactaatatg     600
agatatccaa cttctcctgt tatgcatata ggatataaac cattagaatt agcaggtact     660
catggtattt ctactagtag taagaaaatt aaggattctt cttgtaaaga tgttgaatta    720
aaaccgggat ggaaaatata tataaaaatc ttagataaaa attattatga taatgttggt    780
gggtatactg ttactttttat tgatgggata aaagctgaac aagaattttc tgcatttgaa    840
tgggttagaa aggaagttag aggtaggtta gataaagcag gagaagacct ttttaaaaat      900
atagttaaga atccagtatt taagaatttt gttttttagtt tattaacttt atttttttaata    960
```

```
tttggttcac ttgcttatat tctaggtatt gttcgtaccc catttgctga tattattgtt    1020
aggttgttga aaatatcttt aatgttattg ttaatttctc ctaatagttg ggatttcttt    1080
tataaccatt tacttcgttt attcattcat ggtacagatc aaattattgc tatgattaat    1140
agctatacag gtgattataa tcctcaagca ccatttctt ttatggatat aatgattaga    1200
gataagattt tttctccagt gatttggaaa ataaaaatta gagcattgat tgttgccaat    1260
ttttcttcga tatttgctgt attggtaatt gttattgctg ttttgattta tattgcattg    1320
tgcatatatg gttttgttat atatctcaca gcgtttgttg gtattacgtt tctagtaggg    1380
ttaatgccac tgttattgtt aggtattctt ttttctcaat ttaagagctt atttgatggt    1440
tggttaacac aatgtataag tttctcactg caggcaatat taatatttac tttgatttca    1500
ctgtttggga cacttattat gaattattat taccgtattt ttggatttac ggtatgttat    1560
aatgaatgga tgaaagtaaa aatttgttta tttggtaggg ttggatgttt agtagataaa    1620
agtttatttg gatggactcc gggtcagatg tatgatccaa aagttattgg aataacttca    1680
gattttaatg ttagtgataa aaaagcttcg agtgatgatc cagatgatat aaaaatgtct    1740
ggtaatgcaa gatataagtt tactggtgga ggttggtata ttagtgttcc tcctgatcat    1800
aaacataaag attttaggta tatagattat ccattccttg atccagatac tgaaagtgat    1860
agtaatccat atggtgttaa tgttgcaaaa gatagtaagc taaggaatt atcacatttt    1920 gttaatgcac tactaactac tgataagaaa tatgtagttg ctaggttagt tgctgatata    1980
agggttgagt tagagaaact ggtaaaaaat aacacaataa cctctgagag tcaaaataaa    2040
gtattaaata ttatagatga aagaattaag aaagataagg atgctggtaa aagtgaattg    2100
gataaatatg gtgatcaaaa tttcaagtca caaataatta gatctgttat tgataatgtt    2160
atcgatggag ctgctattac tcctactagt caagaaaaat taaatgaaca gtatgattat    2220
gctttaattc aaggaatacg tgctggagat ttaattttgt ggtctgaagt tggttcttta    2280
ttccttgctg cattactgat atggcaaatg cgtgcttttg tacaaagtgt tgctgtatct    2340
ctagcaggtg gtagtatgat gtcgcaaact attgcaagta tgtatgagga aggattccta    2400 aagactttt caagtattcc tgttgtgggt aaggtattta aaacaatcga tggaggttta    2460
gattcgtata aattattagt aggtaactat ataacagaaa cagcacgtag gccttttaaat   2520 atgttacaga aagttcctgt tttaggacat gctgttaaat ttactggtaa agttgccggt    2580
ggattgacat cttcatatgg tgaatatgat agaagacata gttcaaactt taagcagcta    2640
aattatgctc gtgctttcat aggagctcat ctaggatttt ctccgctgag tgcaatgaaa    2700
tatttaggtg ggtatgctgc tggaaaaatg ttaggtagta ggagtggtgg actaattcat    2760
aatatggttc aggatcgtaa agctgcattg gatagtttaa aggcacatat attggggcct    2820
gaacaacata agcctagtcc ttatataccg aaaaagaaag aagatgattc taatccttt     2880 gttaaaaatg atgctaaaaa tttaggaggt gattctagct ctcctggtag taaaaattat    2940
gatgggcatg taagaggtga gcctcattct attgcaagaa ctgatactgg taatgtgaga    3000
ggtgattctt atgatacaaa ttatgctggt aatgtaatag gtgatgctgc tgttgctaaa    3060
ggctatgctg gcggcgtagt aggcagttct ggtcctatta ctaggttaga attacaaaat    3120
cagcactctt tattggatga cgctggaaat gtacgtgtag gtaaggataa tttagcagat    3180
gctcttgaag caagggaaca acttaaaaca atgcgtgaaa atactaaaga tgaaactgca    3240
ttgataaata ttaattatga tattgatagg ctcgatagtc ccttacataa acatttaggt    3300
catgattttg agcaagtaac gcaagattat gctagttctc atatggctgt tcaacattcc    3360
```

```
gctgatttat cagcgactga ttattctaga ttaaatattg acgatatttc taaattagat    3420
agtacagcac aaatatccag tgcttctgtt ccagatacag gacaagatat attacatagt    3480
aatgctgctg cacaatcaag tatgctagat gttgggagag atgagatatc tgattttatt    3540
tctgcaagtg ctttaaaaga ggaaactata ccacacgaag taatagaatt aaatgtttta    3600
ggaacaagtt ctgggcagtc attatctagt gaaactagtg tacatgtaca agatgaagta    3660
caagttgaca gaagagaaac tgttacagca cctagtgata ctgcacaacc aagtgcgttg    3720
gatgtagaat tatctggagg tagagtatct gagattagtt ccacaggtgc ttcacaaggg    3780
gaaacttctc ctgagcagca attatctagt gaagttggtg tatatgtaca agatggagta    3840
caagttgaga gaagcgaaac agttacatca cctagtgata ctacacaacc aagtgcgtta    3900
gatgtagaat tatctggaga tggattgtct gatattagtt ctacaagtgt ttcacaaggg    3960
gaaacttctc cacaatctga agaaatagaa ttaaatgttt tgggagcaac ttctgagcag    4020
caattatcta gtgaagttgg tgtatatgta caagatggag tacaagttga gagaagcgaa    4080
gcagttacat cacctagtga tactacacaa ccaagtacgt tagatgtaga attatctgga    4140
gatggattat ctgatattag ttctacaggt gtttcacaag ggaaacttc ttcacaatct    4200 gaagatttag aggcaatctt tgatcaaaca ttaatcggtg aaaatgaatc gcatgctagt    4260
actagtgata atgatataga accaatagct agtgatgaaa atgtgttatt aggacatgaa    4320
aattttgata gccttcttga tacagatcct ttatctcatg atacacaaga agtactggt    4380 tttattgatg agaaatctag taatgaattc gaagaaagta aagagttagt tgatcataaa    4440
gatacaatag aaaatatacc agatgtagat catactcctg atgcgtttgg gaaggaactg    4500
gatgttcctc aaacttcaga tcaagaatta attgatatga atgcagaagg taattcttct    4560
gttaatgtgc tatctgatca atatcaagac actgcttctg aattatctag ttcagagagt    4620
tcagatggta gtgagtcaag aggttcagaa agtgatgata agtgttagaa cctgaatta    4680 caggcaaata cttattatgc tactgataat gaagttttag atgtggcttc tcttgaatta    4740
ggattgtctg gtgttgcagt aggaaatgta gagcctgctc cggaagatag tggaacaaaa    4800
cctgaagcat ttgaagtgga aagtaatgaa agtgaaggtg tagtaagtgt aacagaagga    4860
cacagtgaca gtgctgcttc tagtgaaagt attgataagg aaagtagtga agatagtcaa    4920
cttgatcaaa catcaatgga agaacaagat aaggtaggag aatttgaaag agatagtaat    4980
gctgaagata ctagtataga taagagggtt agtggaaaac cagatatagt agaacctgtt    5040
caagaaggta gtgaaacaaa acctgaagca gttgaagtgg agagtaatga agtgaaggt    5100 gtagtaagtg taacagaaga acacagtgac agtgctgctt ctagtgaaag tattgataag    5160
gaaagtagtg aagatagtca acttgatcaa acatcaatgg aagaacaaga taaggtagaa    5220
gaatttgaag tagctgaaga tactagtgta gataaagagg ttagtggaaa accagatata    5280
gtagagcctg ctcaagaagg tagtgaaaca aaacctgaag cagttgaagt ggaaagtaat    5340
gaaagtgaag gtgtagtaag tgtaacagaa gaacacagtg acagtgctgc ttctagtgga    5400
aatattgata aggaaagtag tgaagatagt caacttgatc aaacatcaat ggaagaacaa    5460
gataaggtag gagaatttga agtagctgaa gatactagtg tagataaaga ggttagtgga    5520
aaaccagata tagtagaacc tgctcaagaa ggtagtgaaa caaaacctga agcagttgaa    5580
gtggaaagta atgaaagtga aggtgtagta gatgtaacag aagaacacag tgacagtgct    5640
gcctctagta aagtattga taaggaaagt agtgaagata gtcaacttga tcaaacatca    5700
atggaagaac aagataaggt aggagaatct gaaagagata gtaatgctga agatgctagt    5760
```

-continued

```
atagatggta aagaagttag tggaaaacca gatatagtag aacctgttca agaaggtagt    5820
gaaacaaaac ctgaagcagt tgaagtggaa ggtaatgaaa gtgaaggtgt agtagatgta    5880
acagaagaac acagtgacag tgctgcttct agtgaaagta ttgataagga aagtagtgaa    5940
gatagtcaac ttgatcaaac atcaatggaa gaacaagata aggtaggaga atctgaagta    6000
gctgaagatg ctagtataga tggtaaagaa gttagtggaa aaccagatat agtgaacct    6060 gttcaagaag gtagcacaga agaagaatct acaagtgtac tagatgaaga tagtaaacgt    6120
gatgtggaag aatctgaaga gagggacat gatacttctt ctgatgaagg tacagaagtt    6180
gatgaagtag atagtgatgg tgatgatagt gcagacgtgg aaaaaggatc taatgataca    6240
ttagagaatg atttggaagc agaagagtct aaggtggaat taacagaaga gcttgcagtt    6300
aaagatatgc ctgaggagtc agtaactgaa gggcgtggaa tgaaaaagc ttctgttgtt    6360 actgatgata tgtcagaggg attagctgct gtccatcaag ttgatagtgg taaggaattc    6420
aagttgcaag aaaaatggg tctagaaggt gcacagtcta ttcatattcc taagtcgtta    6480
aaatctgaag aaaaggatgc tgtaagtaag aaaagtagta cggctaagaa aacagaatct    6540
acagatagta aagatagtgc taagagaaaa aaggtacact caacatctag taaaacaaag    6600
aaaacttctt taccaaaaat tatgtctggt gttaaatttt tggtaaatca atatgcaaaa    6660
cagatatcta cagggctatc agaatctttt gataaattct ttgaagatac tgaatctaag    6720
aaacgtggta aaagaaaacg ttcaaaagaa gatattgaat ctatggtaag agatcttgaa    6780
caattacttg tatctttaaa agataaaaaa tcaaagctta ctgatcctag tgagatagca    6840
aatatagaag atgatataag aaaattagaa agtacaataa aatccatttt agataatcaa    6900
tga                                                                  6903

<210> SEQ ID NO 17
<211> LENGTH: 2361
<212> TYPE: DNA
<213> ORGANISM: Ehrlichia ruminantium

<400> SEQUENCE: 17
gtgttattag gacatgaaaa ttttgatagc cttcttgata cagatccttt atctcatgat      60
acacaagaaa gtactgattt tattgatgag aaatctagta tgaattcga agaaagtaaa     120 gagttagttg atcataaaga tacaatagaa agtataccag atgtagatca cacttctgat     180
gcgtttggga aggaactgga tgttcctcaa acttcagatc aagaattaat tgatatgaat     240
gcagaaggta ttcttctgt taatgtgcta tctgatcaat atcaagacac tgcttctgaa     300
ttatctagtt cagagagttc agatggtact gagtcaagag gttcagaaag tgatgatcaa     360
gtattagaac ctgagttaca ggcaaatact tattatgcta ctgataatga agttttagat     420
gtggcttctc ttgaattagg attgcctggt gttgcagtag aaatgtaga gcctgttcaa     480 gaaggtagtg aaacaaaacc tgaagcagtt gaagtggaag gtaatgaaag tgaaggtgta     540
gtaaatgtaa cagaagaaca cagtgacagt gctgcttcta gtgaaagtat tgataaggaa     600
agtagtgaag atagtcaact tgatcaaacg tcaatggaag aacaagataa ggtagaagaa     660
tttgaaagag atagtaatgc tgaagatact agtgtagata agaggttag tgaaaaacca     720 gatatagtag agcctgctcc ggaagatagt ggaacaaaac ctgaagcagt tgaagtggaa     780
ggtaatgaaa gtgaaggtgt agtaaatgta acagaagaac acagtgacag tgctgcttct     840
agtgaaagta ttgataagga aagtagtgaa gatagtcaac ttgatcaaac atcaatggaa     900
gaacaagata aggtaggaga atctgaaaga gatagtaatg ctgaagatgc tagtatagat     960
```

```
ggtaaagaag ttagaggaaa accagatata gtagaacctg ctcaagaagg tagtgaaaca      1020
aaacctgaag cagttgaagt ggaaagtaat gaaagtgaag gtgtagtaag tgtaacagaa      1080
gaacacagtg acagtgctgc ttctagtgga aatattgata aggaaagtag tgaagatagt      1140
caacttgatc aaacatcaat ggaagaacaa gataaggtag gagaatctga aagagatagt      1200
aatgctgaag atgctagtgt agataaagag gttagtggaa aaccagatat agtgaaacct      1260
gctcaagaag gtagtgaaac aaaacctgaa gcagttgaag tggaaagtaa tgaaagtgaa      1320
ggtgtagtag atgtaacaga gaacacagt gacagtgctg cttctagtga agtattgat        1380 aaggaaagta gtgaagatag tcaacttgat caaacatcaa tggaagaaca agataaggta      1440
ggagaatctg aaagagatag taatgctgaa gatactagtg tagataaaga ggttagtgaa      1500
aaaccagata tagtagagcc tgctcaagaa ggtagcacag aagaagaatc tacaagtgta      1560
ctagatgaag atagtaaacg tgatgtggaa gaatctgaag aagagggaca tgatacttct      1620
tctgatgaag gtacagaagt tgatgaagta gatagtgatg gtgatagtgc agatgtggaa      1680
aaaggatcta atgatacatt agagaatgat ttggaagcag aagagtctaa ggtggaatta      1740
acagaagagc ttgcagttaa agatatgcct gaggagtcag taactgaagg gcatggaatg      1800
aaaaaagctt ctgttgttac tgatgatatg tcagagggat tagctgctgt ccatcaagtt      1860
gatagtggta aggaattcaa gttgcaagaa aaaatgggtc tagaaggtgc acagtctatt      1920
catattccta gtcgttaaa atctgaagaa aaggatgctg taagtaagaa aagtagtacg       1980
gctaagaaaa cagagtctac agatagtaaa gataatgcta aagagaaaaa aggtacatca      2040
acatctaata aaacaaagaa aacttcttta ccaaaaatta tgtctggtgt taaaattta       2100 gtaaatcaat atgcaaaaca gatatctaca gggctatcag aatcttttga taaattcttt      2160
gaagatactg aatctaagaa acgtggtaaa agaaaacttt caaaagaaga tattgaatct      2220
atggtaagag atcttgaaca attacttgta tctttaaaag ataaaaaatc aaagcttact      2280
gatcctagtg agatagcaaa catagaagat gatataagaa aattagaaag tacaataaaa      2340
tccattttag ataatcaatg a                                                2361
```

<210> SEQ ID NO 18
<211> LENGTH: 4473
<212> TYPE: DNA
<213> ORGANISM: Ehrlichia ruminantium

<400> SEQUENCE: 18

```
atgtataatt ttattaaaaa tcattttata aaattattgt tacttttatt gatgactgca        60
tgtgaatcaa atcagcatcc ggtgcctaga tgtgtaccag ctgatgtatt tactgaaggc       120
aggacaactt ctgtatctgc atattttgat cctacttctg aaaattttat gtctgacaat       180
aaggctttag gaaattctgt tgaagataat caagtagtgc ggtggaaata tactggatat       240
gtaacaaatg gtcatccgat tgtattaagg gctgaaggaa tgtggacttc atgggccaag       300
aaaagtaata atgtaactga agttcaaaaa aatactacag attatggaga tgatgatgta       360
gatcgttata atgctatctt ggcagttgat agagtttgtg gtccttataa aaaaatagag       420
aagacgtttt ctaatggtac aaatcaatgt aaagtatcat gtgaaatgat ttccggagtt       480
caagacaatt tagagacagg aacatatggt ccaccttgtt ggtttagaaa tggttatggt       540
gcgtacctat tattcaaaag accagaagat cctgaaccaa atgaaacgat tactaatatg       600
agatatccaa cttctcctgt tatgcatata ggatataaac cattagaatt agcaggtact       660
catggtattt ctactagtag taagaaaatt aaggattctt cttgtaaaga tgttgaatta       720
```

```
aaaccaggat ggaaaatata tataaaaatc ttggatagaa attattatga taatgttggt    780
gggtatacag ttacttttat tgatgggata aaagctgaac aagaattttc tgcatttgaa    840
tgggttagaa aggaagttag aggtaggtta gataaagcgg gagaagacct ttttaaaaat    900
atagttaaga atccggtatt taagaattt gttttagtt tattaactt atttttaata      960 tttggttcac ttgcttatat tctaggtatt gttcgtactc cgtttgctga tattattgtt   1020
aggttattga aaatatcttt aatgttattg ttaatttctc ctaatagttg ggatttcttt   1080
tataaccatt tacttcgttt attcattcat ggtacagatc aaattattgc tatgattaat   1140
agctatacag gtgattataa tcctcaagca ccatttctt ttatggatat aatgattagg    1200
gataagattt tttctccagt gatttggaaa ataaaaatca gagcattgat tgttgccaat   1260
ttttcttcaa tatttgctgt attggtaatt gttattgctg ttctgattta tattgcattg   1320
tgcatatatg gttttgttat atatctcaca gcgtttgttg gtattacctt tctagtaggg   1380
ttaatgccat tgttattgtt aggtattctt ttttctcaat ttaagagctt atttgatggt   1440
tggttaacac aatgtataag tttctcgttg caggcaatat taatatttac tttgatttca   1500
ttatttggga cacttattat gaattattat taccgtattt ttggatttac ggtatgttat   1560
aatgaatgga tgaaagtaaa aatttgttta tttggtagag ttggatgttt agtagataaa   1620
agtttatttg ggtggactcc aggtcagatg tatgatccaa aagttattgg aataacttca   1680
gattttaacg ttagtgataa gaaagcttct agtgatgatc cagatgatat aaaaatgtct   1740
ggtaatgcaa gatataagtt tactggtgga ggtggatata ttagtgttcc tcctgatcac   1800
aagtataagg atttaggta tatagattat ccgttccttg atccagatac tgaaagtgat   1860
agtaatccac atggtgttaa tgttgcaaaa gatagtcctt tcaaagaatt gtcgcatctt   1920
gttaatgcgc tactaactac tgataaaaaa tatatagttg ctaggttggt tgctgatata   1980
aagactgagt tagagaaatt ggtgaaaaat aagacaataa cctctgatag tcaaaataaa   2040
gtattgaaga ttatagatga cagaattaaa aaagataagg atgctggtaa aagtgaattg   2100
gataagtatg gtgatcaaag ttttaagtca caaataatta gatctgttat tgataatgtt   2160
atcgatggag ctgctattac tcctactagt caagaaaaat taaatgaaca gtatgattat   2220
gctttaattc aaggaatacg tgctggagat ttaattttgt ggtctgaagt tggttcttta   2280
ttccttgctg cattactgat atggcaaatg cgtgcttttg tacaaagtgt tgctgtatct   2340
ctagcaggtg gtagtatgat gtcacaaaact attgcaagta tgtatgagga aggattccta   2400 aagactttt caagtattcc tgttgtgggt aaggtattta aaacaatcga tggaggttta   2460
gattcgtata aattattagt aggtaactat ataacggaaa cagcacgtag gcctttaaat   2520
atgttacaga aagttcctgt gttaggacat gctgttaaat ttactggtaa agttgctggt   2580
ggattgacat cttcatatgg tgaatatgat agaaggcaca gttcaaactt taagcagcta   2640
aattatgctc gtgctttcat aggagctcac ctaggatttt ctccactgag tgcaatgaaa   2700
tatttaggtg ggtatgctgc tggaaaaatg ttaggtagta ggagtggtgg actaattcat   2760
aatatggttc aggatcgtaa agctgcattg gatagtttaa aggcacatat attggggcct   2820
gaacaacata gcctagtcc ttatataccg aaaagaaag aagatgattc taatccttt     2880 gttaaaaatg atgctaaaaa tttaggaggt gattctagct ctcctggtag taaaaattat   2940
gatgggcatg taagaggtga gcctcattct attgcaagaa ctgatactgg taatgtgaga   3000
ggtgattctt atgatacaaa ttatgctggt aatgtaatag gtgatgctgc tgttgctaaa   3060
ggctatgctg gcggcgtagt aggtagttct ggtcctatta ctaggttaga attacaaaat   3120
```

| | |
|---|---|
| cagcactctt tattagatga tgctggaaat gtacgtgtag gtaaggataa tttagcagat | 3180 |
| gctcttgaag caagggaaca acttaaaaca atgcgtgaaa atactaaaga tgaaactgca | 3240 |
| ttgataaata ttaattatga tattgatagg ctagatagtg ctttacataa gcatttaggt | 3300 |
| catgattttg agcaagtaac gcaagattat gctaattctc atatggctgt tcaacattcc | 3360 |
| tctgatttat cagcgactga ttattctaga ttaaatattg atgatatttc tagattagat | 3420 |
| ggtacagcac aaatatctag tgcttctgtt ccagatacag gacaagatat attacatagt | 3480 |
| aatgctgctg cacaatcaag tatgctagat gtcgggagag atgagatatc tgattttatt | 3540 |
| tctgcaagtg ctttaaaaga ggaaactata ccacacgaag taatagaatt aaatgtttta | 3600 |
| ggagcaactc ctgagcagca attatctagt gaaactggtg tacatgtaca agatgaagta | 3660 |
| caagttgata gaagcgaagc agttacatca cctagtgata ctacacaatc aagtgcgtta | 3720 |
| gatgtagaat tacctggaga tggattatct aatattagtt ccacaggtgt ttcacaaggg | 3780 |
| gaaacttctc cacaatctga agaaatagaa ttaaatgttt gggagcaac ttctgagcag | 3840 |
| caattatctg atgaagttgg tgtatatgta caagatggag tacaagttga gagaagcgaa | 3900 |
| gcagttacat cacctagtga tactacacaa ccaagtacgt tagatgtaga attatctgga | 3960 |
| gatggattat ctgatattag ttctacaggt gtttcacaag gggaaacttc tccacaatct | 4020 |
| gaagaaatag aattgaatgt tttaggagca acttctgagc agcaattatc tagtgaaact | 4080 |
| ggtgtacatg tacaagatga agtacaagtt gatagaagcg aagcagttac atcacctagt | 4140 |
| gatactacac aaccaagtgc gttagatgta gaattacctg gagatggatt atctgatatt | 4200 |
| agttccacag gtgtttcaca aggggaaact tcttcacaat ctgaagaaat agaattttat | 4260 |
| gttttgggag caacttctga gcagcaatta tctagtgaag ttggtgtata tgtacaagat | 4320 |
| gaagtacaag ttgatagaag cgaagcagtt acatcaccta gtgatactac acaaccaagt | 4380 |
| gcgttagatg tagaattatc tggagatgga ttatctgata ttagttctac aggtgtttca | 4440 |
| caggggaaac ttcttcacaa tctgaagatt tag | 4473 |

<210> SEQ ID NO 19
<211> LENGTH: 3522
<212> TYPE: DNA
<213> ORGANISM: Ehrlichia ruminantium

<400> SEQUENCE: 19

| | |
|---|---|
| atgaatgaga taatcctata cacagcagtg tcgctgtttt ttatatgtgt ttactatgtt | 60 |
| ctgcttgtgg ttaggtttgt atgttatgtg ttgagtgtta tgaagtataa gtcaaaggaa | 120 |
| ttggacatat cagataatta tacaaaaagt agggttactt attgtagtca gagtgaatat | 180 |
| gaaaagtacg aaatggacac tttatctgga aaagatggta ttgaatttct aaaatcagtt | 240 |
| taccataatg atagtgatga tataggtcat gttttaaaat caaatctac tgtttcatct | 300 |
| accaaaatgg atcaggtaac acatcaagtt cctggcgttc aaactataga acacgatagt | 360 |
| gcgatagaag gtcaccaagt tatggataag gaaaatgctg gtgttggtgt tcactatagt | 420 |
| catactgaaa ctactataaa aacaagtctt agttttaaat ctgatgttat ggttgatact | 480 |
| aaggataaat ctgtagagaa aaagtagtac cctgaaaata ctataagaat aaatgaaaaa | 540 |
| aagagagatg ttttttgtaag tgctagtatt caaactgata taaaaagtaa tcaagttaaa | 600 |
| ttatctagtt ctgtattaga aaaccagat gagaaaagtg atgttactga tacagcgtgt | 660 |
| acaggtagta ctaaggataa atctgtagag gaaaaagtag tacctgaagg tgatactata | 720 |
| agaataaatg aaaaaaagag agatgttttt gtaagtgcta gtgctcaaac tggtgatatg | 780 |

```
aaaagtgatc aagttaaatt atctggttct agattagaaa aactagatga gagaaaggat      840
gttactgata caggttgtgc aggtagtact aaggacaaat ctgtagagaa aaaagtagta      900
tctgaaggta ctgctataag agatgaaaag gagagtagtg ttgctagaag tgttggtgtt      960
acttttaatc ttcaaagtgg taatgtaaaa gatgataaag taaaactatc aggtgtagat     1020
ttaggtaaaa tagaggattc agttttatct gcttctagtt gtgaaactac tgttaaggat     1080
aataagcctg ttatatgtgt tggaaaagaa agtacgtttc aattagcttc aagtttggat     1140
ttggttaata ctgttgaaga tagttcaaga aatactcgtg gtttaagtga aacttgttct     1200
ttaatgttag attttgacag aaatggtaat cctgtatacg aagaggcaac tagtaagtta     1260
gtgcctagtt tctatcctga taatgttata tatcacacta aagaaaaaca ttgtggtgtt     1320
gatcttcctc aatcagaaga tcaactttat tcatgtatta ctaatgtgca tagtcaatat     1380
gatgtgactg aaaatagtgt aagtgtatat ccgcgtgatt tggttcctga tgatataaaa     1440
caagctaaac agaatgaaga tactaaacag ggtgctttta tagctacagg ttctacaacc     1500
gcggctgcgc atagtcaata tgatgtgact gaaaatagcg taagtgtatg tcagagtgat     1560
ttggttcctg atgatataaa acaagctaaa cagagtgaag atactaaaca gggtgctttt     1620
atagctacag gttctacaac cgcggctgcg catagtcaat atgatgtgac tgaaaatagt     1680
gttagtgtat atcagagtga cttagtttct gataatataa acaagctaa acagaatgaa     1740 gatactaagc agggtgcttt tatagctaca ggttctacaa ccgcggctgc gcatagtcaa     1800
tatgatatga ctgaaaatag cgtaagtgta tgtcagagtg acttagttcc tgatggtgta     1860
aaacaatcta acagcatga agatactaag cagggtgctt ttatagttac aggttctgta     1920
tctgctaagt tagatattgt tgatgtagtt agtttagggg aaaaacgtga tattgatgaa     1980
aaagttgtta agtcatcagg ttgtactact gctgattcag ttagtaatcc tgtaggtatg     2040
gataaagttc aatattgtgt acctgactta gagatgagag taaaaatgga tcttgtagaa     2100
gatcaccata atatggctag tatggaaaaa tgttatcctg atagagaagt tgttgagcaa     2160
ttaagtaatg ttactacttg tttggttagt actccagtaa ttgaacatag agttcatagt     2220
gttgagtctg ttgcagagtt acaagtaaaa ataggtcctt tagatgaggg aaaatgtaaa     2280
gacagtgtgg taaggagctc atcatttact agtgatacat gtttaaaaga tacaggtgca     2340
acaatgactg tagaagaata tggtaataaa cctagtacag gtctttgtgc tagtagggga     2400
gatgatagtg tttcttctat gattggtata ggttcgtatt ttatagataa gatgatttgt     2460
gatattgata ctactgtgca gcttaataat acattttcta cttagaaaa aagaaaaaac     2520 tgttttatag ataatattaa aaaaaataat gaaaaaatat ttagtaacct tgttaatatt     2580
atggatttaa taaagaaac ggtaggtatt caattttttg atactaaaag tacagatgat     2640
atatccaggt atgtaatgga acaatctagt ggtgtttatg atgatgttat gtcacaaatg     2700
cttatccaag atgaaaaata tttatttaag gtctttaaac atattattcc ggttttgct     2760 aaaatattct ttaacaatga tcctatatct tcaatggaat ggaaattagt agatgaattg     2820
ttctctatga aagggcagt cttacaagat aatgtgtatt ttcaaaggat atttttattgt     2880 atagtgtgtg catgtgaaaa aactgcaggt acaataaaga aaattcagtc gttatctaaa     2940
cagtgtgatg aaatacgaga aaagattaaa agtgtaatc taaggcaagg aaagaagaaa     3000
agtgcattgt cgaaatttac agatcatttt agtgaaaaaa aggaagacct gttgtgttta     3060
ttagataaaa tagaaaaaga actgaattta actaagcaag tttacactaa tcttatagca     3120 gaaaagagg cgttattaac aggagatgtt gcttatataa gatattttgt atcacgtatt     3180
```

```
gtttttgata gttggaaatt tgatgataag gctaaacagg ttgtcaaaaa tataaagaac    3240
ctagcaccat atgtgttatg tgatgtgttg tatgaagaag aaaaaaaata tctaggtttg    3300
gtgaagtgta ttgtttgtga gtacacggtt ttttataaag atatagataa tttttttacct   3360 atagttcaac aatatcatga tcgacgacaa tctagaagtg ctgcagccca aaaatttttat   3420 gatcaggaaa ttgatggtgt tcttcctatg gatactttag aaggtgtagg ggatcttgta    3480
gctatggaat taggacaaaa cagtaaatgt aatgcacatt aa                        3522

<210> SEQ ID NO 20
<211> LENGTH: 4122
<212> TYPE: DNA
<213> ORGANISM: Ehrlichia ruminantium

<400> SEQUENCE: 20
atgaatgaga taatcctata cacagcagta tcactgtttt ttatatgtat ttactatgtt      60
ctgcttgtgg ctaggtttgt gtgttatgtg ttaagtatta tgaagtataa gtcaagagaa    120
ttggatatat cggataatga tacaaaaagt agggttactt attgtagtca gagtgagtat    180
gaatatggaa agtacgagat ggaaacttta tctggaaaag atggtattga atttctaaaa    240
tcagtttacc atagtgatag tgatgatgta ggtgatgttt taaaatcaaa atctactgtc    300
tcatctacca aaatggatca ggtaacacat caaatttctg acgttcaaac tatagaacgc    360
gataatgtag aaggtcaaca agttatggtt aaggaaaatg ctggtgttgg tgttcactat    420
aatcatactg aaactattat aaaaacaagt cttagtttta aatctgatgt tatggttgat    480
actaaggata aatctataga ggaaaaagta gtacctgaag gtgatactat aagaataaat    540
gaaaaaaaga gagatgtttt tgtaagtgct agtgctcaaa ctgatatgaa aagtaatcaa    600
gttagattat ctggttctag attagagaaa ccagatgaga aagggatgt tactgataca    660 gcgtgtacag gtagtactaa ggataaatct gtagaggaaa aagtagtacc tgaaggtgat    720
actataagaa taaatgaaaa aagagagat gttttgtaa gtgctagtgc tcaaactgat    780
atgaaaagta atcaagttag attatctggt tctagattag agaaaccaga tgagaaaagg    840
gatgttactg atacagcgtg tacaggtagt actaaggata atctataga ggaaaaagta    900 gtacctgaag gtgatactat aagaataaat gaaaaaaaga gagatgtttt tgtaagtgct    960
agtgctcaaa ctggtgatat gaaaagtgat cacattaaat tatctggttc tagattagag   1020
aaaccagatg agaaagggga tgttactgat acagcgtgta caggtagtac taaggataaa   1080
tctgtagagg aaaaagtagt acctgaaggt gatactaaa gaataaatga aaaaaagaga   1140 gatgttttg taagtgctag tgctcaaact ggtgatatga aaagtgatca cattaaatta   1200
tctggttcta gattagagaa accagatgag agaagggatg ttactgatac aggttgtacg   1260
ggtaatacta aggataaatc tgtagaggaa aaagtagtac tgaaggtga tactataaga   1320 ataaatgaaa aaagagaga tgttttgta agtgctagtg ctcaaactgg tgatatgaaa   1380
agtaatcaag ttaaattatc tggttctaga ttagaaaaac tagatgagag aaaggatgtt   1440
actgatacag gttgtacggg taatactaag gataaatctg tagagaaaaa agtagtatct   1500
gaaggtactg ctataagaga tgaaaaggag agtagtgttg ctagaagtgt tgatgctact   1560
tttaatcttc aaagtggtaa tgtaaaagat gataagtaa aactatcagg tgtagattta   1620
ggtaaaatag aggattcagt tttatctgct tctagttgtg aaactactgt taaggataat   1680
aagcctgtta tatgtgttgg aaaagaaagt acgtttcaat tagcttcaag tttggatttg   1740
gttaatgctg ttgaagatag ttcaagaaat acttgtggtt taagtgaaac ttgttcttta   1800
```

```
atgttagatt ttgacagaaa tggtaatcct gtatacgaag aggcaactag taagttagtg   1860
cctagtttct atcctgataa tgttatatat cacactaaag aaaaacattg tggtgttgat   1920
cttcctcaat cagaagatca actttattca tgtattacta atgtgcatag tcaatatgat   1980
gtgactgaaa atagtgtaag tgtatatccg cgtgatttgg ttcctgatga tataaaacaa   2040
gctaaacaga atgaagatac taaacagggt gcttttatag ctacaggttc tacaaccgcg   2100
gctgcgcata gtcaatatga tgtgactgaa aatagcgtaa gtgtatgtca gagtgactta   2160
gttcctgatg atataaaaca agctaaacag aatgaagata ctaaacaggg tgcttttata   2220
gctacaggtt ctacaaccgc ggctgcgcat agtcaatatg atgtgactga aaatagtgtt   2280
agtgtatatc agagtgactt agttcctgat gatataaaac aagctaaaca gaatgaagat   2340
actaagcagg gtgcttttat agctacaggt tctgcaaccg cggctgcgca tagtcaatat   2400
gatatgactg aaaatagcgt aagtgtatgt cagagtgatt tggttcctga tgatataaaa   2460
caagctaaac agaatgaaga tactaagcag ggtgctttta tagttacagg ttctgtatct   2520
gctaagttag atattgttga tgtagttaat ttaggggaaa aacgtgatat tgatgaaaaa   2580
gttgttaagt catcaggttg tactactgct gattcagtta gtaatcctgt aggtatggat   2640
aaagttcaat attgtgtacc tgacttagag aggagagtga aaatggatct tgtagaagat   2700
cactataata tggctagtat ggaaaaatgt tatcctgata gagaagttgt tgagcaatta   2760
agtaatgtta ctacttgttt ggttagtagt ccagtaattg agcatagagt tcatagtgtt   2820
gagtctgttg cagagttaca agtaaaaata ggtcctttag atgagggaaa atgtagagac   2880
agtgtggtaa tgagctcatc atttactagt gatacatgtt taaagatac aggtgcaaca   2940
atgactgtag aagaatatgg taataaacct agtacaggtc tttgtgctag taggggtgat   3000
gatagtgttt cttctatgat tggtatgggt tcgtatttta tagataagat gatttgtgat   3060
attgatacta ctgtgcagct taataataca ttttctactt tagaaaaaag aaaaaaacat   3120
tttatagatg atattaaaaa aaataatgaa aaaatattta gtaaccttgt taatattatg   3180
gatttaataa agaaacggt aggtattcaa tttttttgata ctaaaagtac agatgatata   3240
tccaggtatg taatggaaca atctagtggt gtttatgatg atgttatgtc acaaatgctt   3300
atccaagatg aaaaatattt atttaaggtc tttaaacata ttattccggt ttttgctaaa   3360
atattcttta caatgatcc tatatcttca atggaatgga attagtaga tgaattgttc   3420
tctatgagaa gggcagtctt acaagataat gtgtattttc aaaggatatt ttattgtata   3480
gtgtgtgcat gtgaaaaaac tgcaggtgca ataagaaaa ttcagtcatt atctaaacag   3540
tgtgatgaaa tacgagaaaa gattaaaaag tgtaatctaa ggcaaggaaa gaagaaaagt   3600
gcattgtcga aatttacaga tcattttagt gaaaaaaagg aagacctgtt gtgtttatta   3660
gataaaatag aaaagaact gaatttaact aagcaagttt acactaatct tatagcagaa   3720
aaagaggcgt tattaacagg agatgttgct tatataagat attttgtatc acgtattgtt   3780
tttgatagtt ggaaatttga tgataaggct aaacaagtta tcaaaaatat aaagaaccta   3840
gcaccatatg tgttacgtga tgtgttgtat gaagaggaaa aaaatatct aggtttggtg   3900
aagtgtattg tttgtgagta cacggttttt tataaagata tagatgattt tttacctgcg   3960
gttcaagaat atcataatcg acgacaatct agaagtgctg cagcccgaaa attttatgat   4020
caggaaattg atggtattct tcttcctatg gatactttag aagatgtagg ggatcttgta   4080
gctatggaat taggacagaa cagtaaatgt aatgcacatt aa                     4122
```

<210> SEQ ID NO 21
<211> LENGTH: 21
<212> TYPE: DNA
<213> ORGANISM: Artificial sequence
<220> FEATURE:
<223> OTHER INFORMATION: P-ERGA-4340-A

<400> SEQUENCE: 21
atgagtcaca gttttattga g                                              21

<210> SEQ ID NO 22
<211> LENGTH: 21
<212> TYPE: DNA
<213> ORGANISM: Artificial sequence
<220> FEATURE:
<223> OTHER INFORMATION: P-ERGA-4340-B

<400> SEQUENCE: 22
cactcaaaat cacaagaagt a                                              21

<210> SEQ ID NO 23
<211> LENGTH: 25
<212> TYPE: DNA
<213> ORGANISM: Artificial sequence
<220> FEATURE:
<223> OTHER INFORMATION: P-ERGA-4980-A

<400> SEQUENCE: 23
atgtatttag tctatttagt agctg                                          25

<210> SEQ ID NO 24
<211> LENGTH: 23
<212> TYPE: DNA
<213> ORGANISM: Artificial sequence
<220> FEATURE:
<223> OTHER INFORMATION: P-ERGA-4980-B

<400> SEQUENCE: 24
ataacatcta attgaacaat atc                                            23

<210> SEQ ID NO 25
<211> LENGTH: 20
<212> TYPE: DNA
<213> ORGANISM: Artificial sequence
<220> FEATURE:
<223> OTHER INFORMATION: P-ERGA-5590-A

<400> SEQUENCE: 25
atgaaaggat ctttatctgc                                                20

<210> SEQ ID NO 26
<211> LENGTH: 20
<212> TYPE: DNA
<213> ORGANISM: Artificial sequence
<220> FEATURE:
<223> OTHER INFORMATION: P-ERGA-5590-B

<400> SEQUENCE: 26
ccttcttctt cttcattatg                                                20

<210> SEQ ID NO 27
<211> LENGTH: 19
<212> TYPE: DNA
<213> ORGANISM: Artificial sequence
<220> FEATURE:
<223> OTHER INFORMATION: P-ERGA-5600-A

<400> SEQUENCE: 27

```
aagaattaca tgatgcagc                                               19

<210> SEQ ID NO 28
<211> LENGTH: 22
<212> TYPE: DNA
<213> ORGANISM: Artificial sequence
<220> FEATURE:
<223> OTHER INFORMATION: P-ERGA-5600-B

<400> SEQUENCE: 28
tcttctcttg ttatactctc tg                                           22

<210> SEQ ID NO 29
<211> LENGTH: 23
<212> TYPE: DNA
<213> ORGANISM: Artificial sequence
<220> FEATURE:
<223> OTHER INFORMATION: P-ERGA-7580-A

<400> SEQUENCE: 29
atggatttaa ataaactaat aaa                                          23

<210> SEQ ID NO 30
<211> LENGTH: 19
<212> TYPE: DNA
<213> ORGANISM: Artificial sequence
<220> FEATURE:
<223> OTHER INFORMATION: P-ERGA-7580-B

<400> SEQUENCE: 30
gcattttctc tacctacga                                               19

<210> SEQ ID NO 31
<211> LENGTH: 25
<212> TYPE: DNA
<213> ORGANISM: Artificial sequence
<220> FEATURE:
<223> OTHER INFORMATION: P-ERWE-8330-A

<400> SEQUENCE: 31
gtctttatat aaaagtaaga attga                                        25

<210> SEQ ID NO 32
<211> LENGTH: 21
<212> TYPE: DNA
<213> ORGANISM: Artificial sequence
<220> FEATURE:
<223> OTHER INFORMATION: P-ERWE-8330-B

<400> SEQUENCE: 32
tgctataaga ttgaactgaa a                                            21

<210> SEQ ID NO 33
<211> LENGTH: 50
<212> TYPE: DNA
<213> ORGANISM: Artificial sequence
<220> FEATURE:
<223> OTHER INFORMATION: Oligo-ERGA-4340

<400> SEQUENCE: 33
cactaattaa caatattact tcttgtgatt ttgagtgtaa taaacaatga              50

<210> SEQ ID NO 34
<211> LENGTH: 51
<212> TYPE: DNA
<213> ORGANISM: Artificial sequence
```

```
<220> FEATURE:
<223> OTHER INFORMATION: Oligo-ERGA-4980

<400> SEQUENCE: 34
gttaaattta atgtcagata ttgttcaatt agatgttata atgttaaaag g          51

<210> SEQ ID NO 35
<211> LENGTH: 50
<212> TYPE: DNA
<213> ORGANISM: Artificial sequence
<220> FEATURE:
<223> OTHER INFORMATION: Oligo-ERGA-5590

<400> SEQUENCE: 35
aggtcgtggt cttgcttttt tccatgatgt tgcaagtaat tttgaaacat             50

<210> SEQ ID NO 36
<211> LENGTH: 50
<212> TYPE: DNA
<213> ORGANISM: Artificial sequence
<220> FEATURE:
<223> OTHER INFORMATION: Oligo-ERGA-5600

<400> SEQUENCE: 36
gtaaacaaga ggaaggatta gaaacacatc agctttccac caatgtagta             50

<210> SEQ ID NO 37
<211> LENGTH: 50
<212> TYPE: DNA
<213> ORGANISM: Artificial sequence
<220> FEATURE:
<223> OTHER INFORMATION: Oligo-ERGA-7580

<400> SEQUENCE: 37
ttgaggattt tatgttctca gaacaaatcg taggtagaga aaatgcagaa             50

<210> SEQ ID NO 38
<211> LENGTH: 51
<212> TYPE: DNA
<213> ORGANISM: Artificial sequence
<220> FEATURE:
<223> OTHER INFORMATION: Oligo-ERWE-8330

<400> SEQUENCE: 38
ttgatgattc tactgatgtt attacttata actctaaaaa aaatatgtgt a           51

<210> SEQ ID NO 39
<211> LENGTH: 50
<212> TYPE: DNA
<213> ORGANISM: Artificial sequence
<220> FEATURE:
<223> OTHER INFORMATION: MutERWE-1390N1

<400> SEQUENCE: 39
tgatgttaca gatagattgt atgtgatgtg gcaattgaga tatcataata             50

<210> SEQ ID NO 40
<211> LENGTH: 50
<212> TYPE: DNA
<213> ORGANISM: Artificial sequence
<220> FEATURE:
<223> OTHER INFORMATION: MutERWE-1390N2

<400> SEQUENCE: 40
tgtaataaag cctactcact atgtaacgca tgtaacattg gaatcgaagt             50
```

<210> SEQ ID NO 41
<211> LENGTH: 50
<212> TYPE: DNA
<213> ORGANISM: Artificial sequence
<220> FEATURE:
<223> OTHER INFORMATION: MutERWE-1390N3

<400> SEQUENCE: 41
tttttaattt ggatagtatt caaagtagtg tttctggtgt gcaagtgaca           50

<210> SEQ ID NO 42
<211> LENGTH: 50
<212> TYPE: DNA
<213> ORGANISM: Artificial sequence
<220> FEATURE:
<223> OTHER INFORMATION: MutERWE-4590N1

<400> SEQUENCE: 42
ttcctattaa catagaacat gctctatcaa atatagcaaa tttaaatgca           50

<210> SEQ ID NO 43
<211> LENGTH: 50
<212> TYPE: DNA
<213> ORGANISM: Artificial sequence
<220> FEATURE:
<223> OTHER INFORMATION: MutERWE-4590N2

<400> SEQUENCE: 43
atctaataaa tgcgtctgat ctaataaatg cgtctgatct aataaagaa            50

<210> SEQ ID NO 44
<211> LENGTH: 50
<212> TYPE: DNA
<213> ORGANISM: Artificial sequence
<220> FEATURE:
<223> OTHER INFORMATION: MutERWE-4600N3

<400> SEQUENCE: 44
tcatcaaaaa gatacgttgt ataggtaata ctatagatcc tgaacaagga           50

<210> SEQ ID NO 45
<211> LENGTH: 50
<212> TYPE: DNA
<213> ORGANISM: Artificial sequence
<220> FEATURE:
<223> OTHER INFORMATION: MutERWE-5460N1

<400> SEQUENCE: 45
tctttaaaag ataaaaaatc aaagcttact gatcctagtg agatagcaaa           50

<210> SEQ ID NO 46
<211> LENGTH: 50
<212> TYPE: DNA
<213> ORGANISM: Artificial sequence
<220> FEATURE:
<223> OTHER INFORMATION: MutERWE-5460N2

<400> SEQUENCE: 46
gaacaagata aggtaggaga atttgaagta gctgaagata ctagtgtaga           50

<210> SEQ ID NO 47
<211> LENGTH: 50
<212> TYPE: DNA
<213> ORGANISM: Artificial sequence
<220> FEATURE:
<223> OTHER INFORMATION: MutERWE-5470N3

<400> SEQUENCE: 47

```
gtgcttctgt tccagataca ggacaagata tattacatag taatgctgct                  50

<210> SEQ ID NO 48
<211> LENGTH: 25
<212> TYPE: DNA
<213> ORGANISM: artificial sequence
<220> FEATURE:
<223> OTHER INFORMATION: P-Z-1-ERGA-120

<400> SEQUENCE: 48
gtattgataa ttatgatggt gaaac                                             25

<210> SEQ ID NO 49
<211> LENGTH: 25
<212> TYPE: DNA
<213> ORGANISM: artificial sequence
<220> FEATURE:
<223> OTHER INFORMATION: P-Z-2-ERGA-120-S

<400> SEQUENCE: 49
gcacatgata tcgaacatgc agttc                                             25

<210> SEQ ID NO 50
<211> LENGTH: 25
<212> TYPE: DNA
<213> ORGANISM: Artificial sequence
<220> FEATURE:
<223> OTHER INFORMATION: P-Z-2-ERGA-120-AS

<400> SEQUENCE: 50
gaactgcatg ttcgatatca tgtgc                                             25

<210> SEQ ID NO 51
<211> LENGTH: 25
<212> TYPE: DNA
<213> ORGANISM: Artificial sequence
<220> FEATURE:
<223> OTHER INFORMATION: P-Z-3-ERGA-120

<400> SEQUENCE: 51
ggttacaagg acaatgatga gtgtg                                             25

<210> SEQ ID NO 52
<211> LENGTH: 25
<212> TYPE: DNA
<213> ORGANISM: Artificial sequence
<220> FEATURE:
<223> OTHER INFORMATION: P-Z-1-ERGA-1350

<400> SEQUENCE: 52
tccaccagag atgttatttg taaag                                             25

<210> SEQ ID NO 53
<211> LENGTH: 25
<212> TYPE: DNA
<213> ORGANISM: Artificial sequence
<220> FEATURE:
<223> OTHER INFORMATION: P-Z-2-ERGA-1350-S

<400> SEQUENCE: 53
cactatgtaa cgcatgtaac attgg                                             25

<210> SEQ ID NO 54
<211> LENGTH: 25
<212> TYPE: DNA
<213> ORGANISM: Artificial sequence
```

```
<220> FEATURE:
<223> OTHER INFORMATION: P-Z-2-ERGA-1350-AS

<400> SEQUENCE: 54
ccaatgttac atgcgttaca tagtg                                              25

<210> SEQ ID NO 55
<211> LENGTH: 25
<212> TYPE: DNA
<213> ORGANISM: Artificial sequence
<220> FEATURE:
<223> OTHER INFORMATION: P-Z-3-ERGA-1350

<400> SEQUENCE: 55
caacagaact ttcagtatta aaagc                                              25

<210> SEQ ID NO 56
<211> LENGTH: 25
<212> TYPE: DNA
<213> ORGANISM: Artificial sequence
<220> FEATURE:
<223> OTHER INFORMATION: P-Z-1-ERGA-4500

<400> SEQUENCE: 56
gttaagtgtg aaatgtattg tttag                                              25

<210> SEQ ID NO 57
<211> LENGTH: 25
<212> TYPE: DNA
<213> ORGANISM: Artificial sequence
<220> FEATURE:
<223> OTHER INFORMATION: P-Z-2-ERGA-4500-S

<400> SEQUENCE: 57
cgtctgatct aataaatgcg tctga                                              25

<210> SEQ ID NO 58
<211> LENGTH: 25
<212> TYPE: DNA
<213> ORGANISM: Artificial sequence
<220> FEATURE:
<223> OTHER INFORMATION: P-Z-2-ERGA-4500-AS

<400> SEQUENCE: 58
tcagacgcat ttattagatc agacg                                              25

<210> SEQ ID NO 59
<211> LENGTH: 25
<212> TYPE: DNA
<213> ORGANISM: Artificial sequence
<220> FEATURE:
<223> OTHER INFORMATION: P-Z-1/3-ERGA-4500-S

<400> SEQUENCE: 59
ctagtaagga aagaaaaact taagc                                              25

<210> SEQ ID NO 60
<211> LENGTH: 25
<212> TYPE: DNA
<213> ORGANISM: Artificial sequence
<220> FEATURE:
<223> OTHER INFORMATION: P-Z-1/3-ERGA-4500-AS

<400> SEQUENCE: 60
gcttaagttt tctttccctt actag                                              25
```

```
<210> SEQ ID NO 61
<211> LENGTH: 25
<212> TYPE: DNA
<213> ORGANISM: Artificial sequence
<220> FEATURE:
<223> OTHER INFORMATION: P-Z-3-ERGA-4500

<400> SEQUENCE: 61
cactttctgt taattcaaaa gtaga                                 25

<210> SEQ ID NO 62
<211> LENGTH: 25
<212> TYPE: DNA
<213> ORGANISM: Artificial sequence
<220> FEATURE:
<223> OTHER INFORMATION: P-Z-1-ERGA-5350

<400> SEQUENCE: 62
gaattaattg atatgaatgc agaag                                 25

<210> SEQ ID NO 63
<211> LENGTH: 26
<212> TYPE: DNA
<213> ORGANISM: Artificial sequence
<220> FEATURE:
<223> OTHER INFORMATION: P-Z-2-ERGA-5350-S

<400> SEQUENCE: 63
ggtaggagaa tttgaagtag ctgaag                                26

<210> SEQ ID NO 64
<211> LENGTH: 26
<212> TYPE: DNA
<213> ORGANISM: Artificial sequence
<220> FEATURE:
<223> OTHER INFORMATION: P-Z-2-ERGA-5350-AS

<400> SEQUENCE: 64
cttcagctac ttcaaattct cctacc                                26

<210> SEQ ID NO 65
<211> LENGTH: 25
<212> TYPE: DNA
<213> ORGANISM: Artificial sequence
<220> FEATURE:
<223> OTHER INFORMATION: P-Z-3-ERGA-5350

<400> SEQUENCE: 65
cttgtagatt cttcttctgt gctac                                 25

<210> SEQ ID NO 66
<211> LENGTH: 25
<212> TYPE: DNA
<213> ORGANISM: Artificial sequence
<220> FEATURE:
<223> OTHER INFORMATION: P-Z-1-ERGA-5740

<400> SEQUENCE: 66
gtaggccaaa aagtataggt aatag                                 25

<210> SEQ ID NO 67
<211> LENGTH: 25
<212> TYPE: DNA
<213> ORGANISM: Artificial sequence
<220> FEATURE:
<223> OTHER INFORMATION: P-Z-2-ERGA-5740-S

<400> SEQUENCE: 67
```

```
ttagaccaaa aacatttgca tctag                                              25

<210> SEQ ID NO 68
<211> LENGTH: 25
<212> TYPE: DNA
<213> ORGANISM: Artificial sequence
<220> FEATURE:
<223> OTHER INFORMATION: P-Z-2-ERGA-5740-AS

<400> SEQUENCE: 68
ctagatgcaa atgtttttgg tctaa                                              25

<210> SEQ ID NO 69
<211> LENGTH: 25
<212> TYPE: DNA
<213> ORGANISM: Artificial sequence
<220> FEATURE:
<223> OTHER INFORMATION: P-Z-3-ERGA-5740

<400> SEQUENCE: 69
caacaaatac atcatcttca agttg                                              25

<210> SEQ ID NO 70
<211> LENGTH: 25
<212> TYPE: DNA
<213> ORGANISM: Artificial sequence
<220> FEATURE:
<223> OTHER INFORMATION: P-Z-1-ERWE-7410

<400> SEQUENCE: 70
agggttactt attgtagtca gagtg                                              25

<210> SEQ ID NO 71
<211> LENGTH: 25
<212> TYPE: DNA
<213> ORGANISM: Artificial sequence
<220> FEATURE:
<223> OTHER INFORMATION: P-Z-2-ERWE-7410-S

<400> SEQUENCE: 71
gagaagggat gttactgata cagcg                                              25

<210> SEQ ID NO 72
<211> LENGTH: 25
<212> TYPE: DNA
<213> ORGANISM: Artificial sequence
<220> FEATURE:
<223> OTHER INFORMATION: P-Z-2-ERWE-7410-AS

<400> SEQUENCE: 72
cgctgtatca gtaacatccc ttctc                                              25

<210> SEQ ID NO 73
<211> LENGTH: 25
<212> TYPE: DNA
<213> ORGANISM: Artificial sequence
<220> FEATURE:
<223> OTHER INFORMATION: P-Z-3-ERWE-7410

<400> SEQUENCE: 73
cctcttcgta tacaggatta ccatt                                              25

<210> SEQ ID NO 74
<211> LENGTH: 25
<212> TYPE: DNA
<213> ORGANISM: Artificial sequence
```

```
<220> FEATURE:
<223> OTHER INFORMATION: P-WEGA-120-S

<400> SEQUENCE: 74
atgggtattg ataattatga tggtg                                    25

<210> SEQ ID NO 75
<211> LENGTH: 25
<212> TYPE: DNA
<213> ORGANISM: Artificial sequence
<220> FEATURE:
<223> OTHER INFORMATION: P-WEGA-120-AS

<400> SEQUENCE: 75
caaatgtaat ttcatggtta caagg                                    25

<210> SEQ ID NO 76
<211> LENGTH: 25
<212> TYPE: DNA
<213> ORGANISM: Artificial sequence
<220> FEATURE:
<223> OTHER INFORMATION: P-WEGA-1350-S

<400> SEQUENCE: 76
gcgatgttat aactgtttca ggtaa                                    25

<210> SEQ ID NO 77
<211> LENGTH: 25
<212> TYPE: DNA
<213> ORGANISM: Artificial sequence
<220> FEATURE:
<223> OTHER INFORMATION: P-WEGA-1350-AS

<400> SEQUENCE: 77
catgagatgt atatcttgta ctcac                                    25

<210> SEQ ID NO 78
<211> LENGTH: 25
<212> TYPE: DNA
<213> ORGANISM: Artificial sequence
<220> FEATURE:
<223> OTHER INFORMATION: P-WEGA-4500-S

<400> SEQUENCE: 78
gttaagtgtg aaatgtattg tttag                                    25

<210> SEQ ID NO 79
<211> LENGTH: 25
<212> TYPE: DNA
<213> ORGANISM: Artificial sequence
<220> FEATURE:
<223> OTHER INFORMATION: P-WEGA-4500-AS

<400> SEQUENCE: 79
ctaaatcttt actttgagat ttatg                                    25

<210> SEQ ID NO 80
<211> LENGTH: 25
<212> TYPE: DNA
<213> ORGANISM: Artificial sequence
<220> FEATURE:
<223> OTHER INFORMATION: P-WEGA-5350-S

<400> SEQUENCE: 80
atttatcagc gactgattat tctag                                    25
```

```
<210> SEQ ID NO 81
<211> LENGTH: 25
<212> TYPE: DNA
<213> ORGANISM: Artificial sequence
<220> FEATURE:
<223> OTHER INFORMATION: P-WEGA-5350-AS

<400> SEQUENCE: 81
ctagtacact tgtagattct tcttc                                              25

<210> SEQ ID NO 82
<211> LENGTH: 28
<212> TYPE: DNA
<213> ORGANISM: Artificial sequence
<220> FEATURE:
<223> OTHER INFORMATION: P-WEGA-5740-S

<400> SEQUENCE: 82
cgtaatatat ctttacaaaa gttgacac                                           28

<210> SEQ ID NO 83
<211> LENGTH: 28
<212> TYPE: DNA
<213> ORGANISM: Artificial sequence
<220> FEATURE:
<223> OTHER INFORMATION: P-WEGA-5740-AS

<400> SEQUENCE: 83
ttcaacaaat acatcatctt caagttga                                           28

<210> SEQ ID NO 84
<211> LENGTH: 25
<212> TYPE: DNA
<213> ORGANISM: Artificial sequence
<220> FEATURE:
<223> OTHER INFORMATION: P-WEGA-7410-S

<400> SEQUENCE: 84
atgaatgaga taatcctata cacag                                              25

<210> SEQ ID NO 85
<211> LENGTH: 25
<212> TYPE: DNA
<213> ORGANISM: Artificial sequence
<220> FEATURE:
<223> OTHER INFORMATION: P-WEGA-7410-AS

<400> SEQUENCE: 85
agtcacatca tattgactat gcaca                                              25
```

SEQUENCES FOR DIFFERENTIAL DIAGNOSTIC OF *EHRLICHIA RUMINANTIUM* AND USE THEREOF

REFERENCE TO SEQUENCE LISTING SUBMITTED ELECTRONICALLY

The official copy of the sequence listing is submitted electronically via EFS-Web as an ASCII formatted sequence listing with a file named "327165-SEQLIST.txt", created on Apr. 17, 2007, and having a size of 68 kilobytes and is filed concurrently with the specification. The sequence listing contained in this ASCII formatted document is part of the specification and is herein incorporated by reference in its entirety.

FIELD AND BACKGROUND OF THE INVENTION

*Rickettsia* are intracellular pathogenic bacteria responsible for various diseases on Humans and animals. *Rickettsia* are transmitted by arthropods, most frequently ticks, lice and mites, and cause major illnesses such as epidemic typhus or Rocky Mountain spotted fever. The genus *Ehrlichia* comprises several species pathogenic for humans and mammals such as *E. chaffeensis*, responsible for Human monocytic ehrlichiosis, *E. canis*, the causing agent of canine monocytic ehrlichiosis, or *E. phagocytophillia*, the agent of Human granulocytic ehrlichiosis.

Another species, *Ehrlichia ruminantium*, formerly known as *Cowdria ruminantium*, is the causing agent of heartwater or cowdriosis, an economically important disease of domestic ruminants. Heartwater can cause up to 80% mortality in susceptible animals. *E. ruminantium* is transmitted by *Amblyomma* ticks and is present in Sub-Saharan Africa and surrounding islands, including Madagascar. Heartwater is also present in several Caribbean islands and is threatening the American mainland.

Serological diagnostic tests of heartwater using crude antigens from whole bacteria detect false positive reactions due to common antigenic determinants. ELISA-based and serological diagnostics have been developed using the Map 1 (WO 9914233; Sumption et al. Clin Diagn Lab Immunol. 10: 910-916, 2003) and the GroEL (WO 9914233) antigens. Other peptides for serological diagnostic have been described (US 2002004051, US 20020132789, WO 02/066652). Although they have dramatically improved specificity, they still display cross reaction with *E. canis* and *E. chaffeensis*. Furthermore, the life span of anti-Map 1 antibodies is rather short.

PCR-based diagnostic methods represent methods of choice for the sensitive and specific detection of *Ehrlichia* in clinically reactive or asymptomatic carrier ruminants, as well as in vectors. However, in the field, hosts and vectors can be co-infested by several parasites and the diversity of pathogen species is further complicated by the existence of extensive intra-species diversity. Improved methods are required to discriminate between strains of differing pathogenesis.

Vaccination against heartwater has long been based on "infection and treatment". Naïve animals are inoculated with blood containing virulent organisms, a procedure which carries a high risk of uncontrolled clinical reactions and the inadvertent spread of undesirable parasites and viruses. A first generation of cowdriosis inactivated vaccine based on cell-cultured derived elementary bodies was developed. Although representing a considerable improvement and the first heartwater vaccine acceptable for widespread use, the level of protection conferred is still not fully satisfactory. Indeed, all animals develop a clinical reaction at challenge despite vaccination. Furthermore, livestock also faces challenge by genetically and antigenically diverse strains.

Diversity of *E. ruminantium* is a key problem which has been recognized for a long time, but insufficient information is available for optimum vaccine formulation and specific diagnostic. The diversity of *E. ruminantium* was demonstrated at the antigenic level by cross-immunisation studies. Variable antigens were identified by ELISA and immunoblot using cross-absorbed immune sera. Genetic diversity was later demonstrated when sequencing the Map 1 gene which showed a high degree of sequence heterogeneity concentrated in three hypervariable regions. This DNA polymorphism was shown to correlate with antigenic polymorphism. Genomic polymorphism was also detected using RAPD and RFLP markers. The map1 gene initially considered as a good marker for geographic diversity, was recently shown not to be geographically constrained. Furthermore, there is no evidence of evolution of map1 under positive selection pressure. Map1 was therefore reported as not being important for evasion of host immune response.

SUMMARY OF THE INVENTION

It is shown herein that between two strains of *Ehrlichia ruminantium*, i.e. strain Gardel and strain Welgevonden, the protection acquired through vaccination with one strain is without effect towards the other one. When an animal is protected by vaccination against the strain Gardel it remains susceptible to lethal infection with the strain Welgevonden, i.e. there is no cross protection between *E. ruminantium* strain Gardel and *E. ruminantium* strain Welgevonden.

Thus, it is important to provide means and diagnostic tools allowing not only to identify *E. ruminantium* but also to differentiate between *E. ruminantium* strain Gardel and *E. ruminantium* strain Welgevonden.

The invention provides genetic markers to differentiate between these two strains, and diagnostic methods using said genetic markers. More specifically, the invention identifies large genetic deletions that are specific either to *E. ruminantium* strain Gardel or to *E. ruminantium* strain Welgevonden, and provide means to distinguish between these two strains by detecting the presence or absence of at least one of said deletions. These deletions may result in the loss of a whole gene, or only of a part of it.

According to a first embodiment, the invention provides gene sequences present in only one of the two differing strains of *Ehrlichia ruminantium*. These sequences represent regions of high strain-specificity for development of diagnostic tools. They will be defined herein as "orphan genes", or "unique genes". They correspond to CDS which have no counterpart in the other strain.

According to a second embodiment, the present invention provides couples of genes which are present in both strains but whose sequences differ between the two strains, due to one or several mutations, including in particular deletions that represent a good target for strain-specific detection. These couples of genes will be defined herein as "allelic couples". The longest member of an allelic couple, that appears, on the basis of sequence data, to encode a potentially functional protein will be defined herein as the "native gene", or the "native allele". The truncated member of the allelic couple, which appears, on the basis of sequence data, to encode a modified protein which is potentially non-functional, or functionally altered, will be defined herein as the "mutant gene", or the "mutant allele".

The CDS corresponding to the native gene in one strain may have, depending on the type of mutation, one or two counterparts in the other strain. More specifically, in case wherein the mutation induces a frameshift where the initial reading frame is changed due to deletion of bases and results in a shift of the frame, a second or additional CDS might be predicted by the annotation software package (i.e. GenoStar package—www.genostar.org) downstream from the site of mutation. This additional CDS is not a novel gene per se but merely the continuation of part of the original full length gene which was shortened by the mutation. If the part of the coding sequence located downstream from the mutation meets the prediction requirements regarding minimal size and presence of a start and a stop codon, it will be considered by the annotation software as a "novel" CDS. A specific number will therefore be attached to this additional CDS although it is only part of the initial full length gene and does not correspond to a biologically distinct gene. As a consequence, in some cases, the beginning of the mutant counterpart of the native gene will be found within a first CDS, while the end of the mutant counterpart of the native gene will be found within a second CDS.

DETAILED DESCRIPTION OF THE INVENTION

Figure 1:
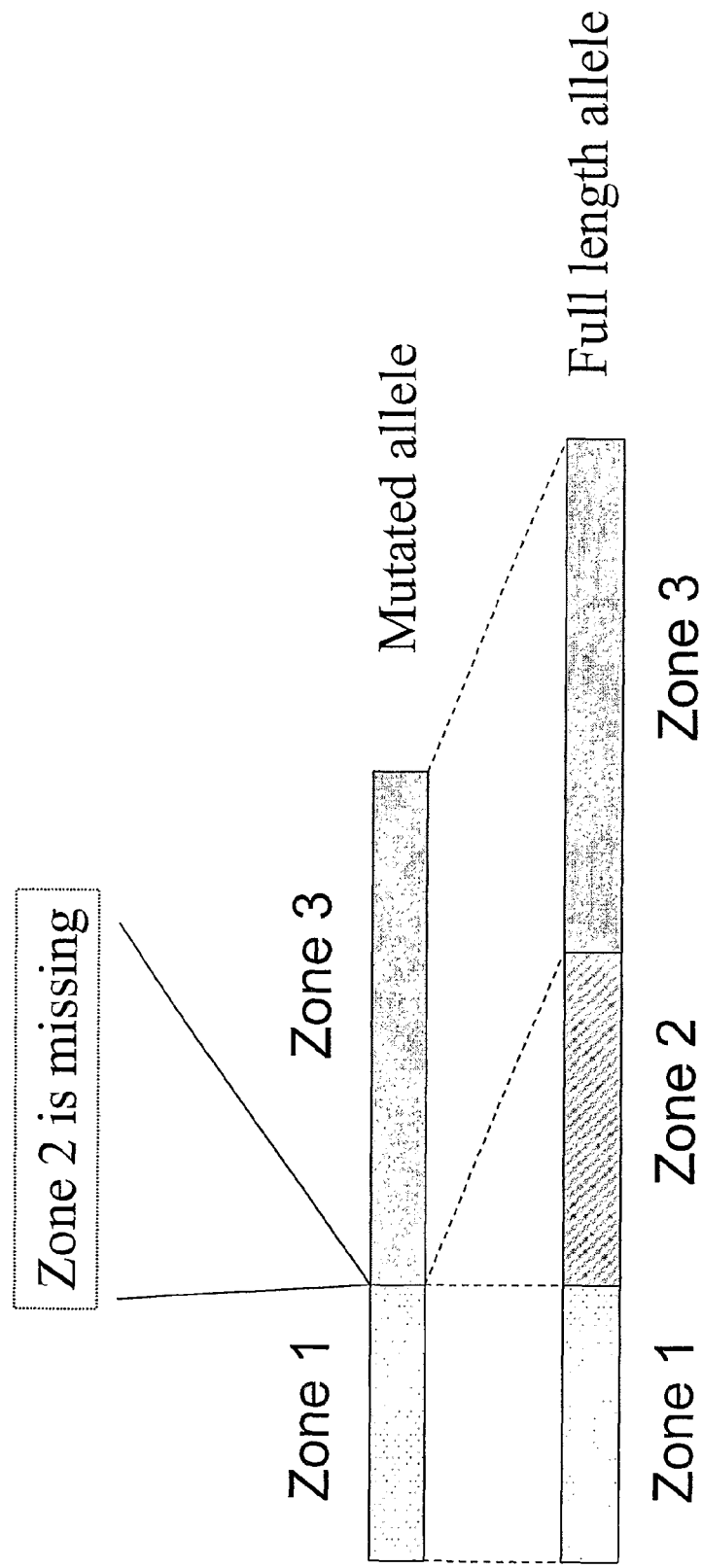
FIG. 1 compares a full length allele to a mutated allele in which a Zone 2 region has been deleted.

The invention provides methods of detecting *Ehrlichia ruminantium* and, advantageously, of discriminating between *Ehrlichia ruminantium* strain Gardel and *Ehrlichia ruminantium* strain Welgevonden, using any of the orphan genes or allelic couples defined above, or any combination thereof.

Accordingly, a first object of the invention is a method for discriminating between *Ehrlichia ruminantium* strain Gardel and *Ehrlichia ruminantium* strain Welgevonden, wherein said method comprises the detection of the presence or the absence, in the bacteria to be tested, of at least one orphan gene selected among:
ERGA_CDS_04340 (SEQ ID NO: 1)
ERGA_CDS_04980 (SEQ ID NO: 2)
ERGA_CDS_05590 (SEQ ID NO: 3)
ERGA_CDS_05600 (SEQ ID NO: 4)
ERGA_CDS_07580 (SEQ ID NO: 5)
ERWE_CDS_08330 (SEQ ID NO: 6)
ERGA_CDS_04340, ERGA_CDS_04980, ERGA_CDS_05590, ERGA_CDS_05600, and ERGA_CDS_07580 are found only in the genome of *E. ruminantium* strain Gardel.

ERWE_CDS_08330 is found only in the genome of *E. ruminantium* strain Welgevonden.

The method of the invention may comprise the detection of a single orphan gene among those listed above, or the detection of any subset of 2, 3, 4, 5, or 6 of these genes.

According to a preferred embodiment of the method of the invention, it comprises the detection of at least one gene selected among ERGA_CDS_05590, and ERGA_CDS_07580.

Another method provided by the present invention for discriminating between *Ehrlichia ruminantium* strain Gardel and *Ehrlichia ruminantium* strain Welgevonden relies on the detection of a member of an allelic couple of genes, as defined above.

Accordingly, a second object of the invention is a method for discriminating between *Ehrlichia ruminantium* strain Gardel and *Ehrlichia ruminantium* strain Welgevonden, wherein said method comprises the detection in the bacteria to be tested, of one of the members of at least one allelic couple of genes selected among:
a couple consisting of ERGA_CDS_00120 (SEQ ID NO: 7) and ERWE_CDS_00120 (SEQ ID NO: 8);
a couple consisting of ERGA_CDS_01350 (SEQ ID NO: 9) and ERWE_CDS_01390 (SEQ ID NO: 10);
a couple consisting of ERGA_CDS_05740 (SEQ ID NO: 11) and ERWE_CDS_05830 (SEQ ID NO: 12);
a couple consisting of ERGA_CDS_04500 (SEQ ID NO: 13) and ERWE_CDS_04590 (SEQ ID NO: 14)+ERWE_CDS_04600 (SEQ ID NO: 15)
a couple consisting of ERGA_CDS_05350 (SEQ ID NO: 16) and
ERWE_CDS_05460 (SEQ ID NO: 17)+ERWE_CDS_05470 (SEQ ID NO: 18)
a couple consisting of ERGA_CDS_07330 (SEQ ID NO: 19) and ERWE_CDS_07410 (SEQ ID NO: 20).
ERGA_CDS_00120, ERGA_CDS_01350, ERGA_CDS_05740, ERGA_CDS_04500 and ERGA_CDS_05350, are alleles herein defined as native alleles, that are found in strain Gardel. ERWE_CDS_07410 is an allele herein defined as a native allele, that is found in strain Welgevonden.

The method of the invention may comprise the detection of a member of a single allelic couple among those listed above, or the detection of a member of each allelic couple in a combination of 2, 3, 4, 5, or 6 of those listed above.

In the allelic couples disclosed above, the mutant allele differs from the native allele by the presence of a deletion resulting in the loss of part of the transcribed region corresponding to the central part of the native coding sequence. This deletion generates a truncation, that can be accompanied by a frameshift.

Three main regions can therefore be considered. These regions are presented in FIG. 1. The first region, named Zone 1, is the 5' region of the gene up to the beginning of the deletion in the mutant gene. Zone 1 is a conserved region of high similarity between *E. ruminantium* strain Gardel and *E. ruminantium* strain Welgevonden. An oligonucleotide designed to match this region will recognize both strains. Zone 2, corresponds to the region of deletion in the mutant gene and therefore only the native allele bears a sequence in this region and can be recognized by an oligonucleotide designed to match this region. Zone 3 is the second conserved region of high similarity between *E. ruminantium* strain Gardel and *E. ruminantium* strain Welgevonden. In this region also, an oligonucleotide designed to match Zone 3 will recognize both strains. In the mutant allele, Zone 1 adjoins Zone 3. An oligonucleotide designed to match the junction, i.e the regions of Zone 1 and Zone 3 immediately flanking the deletion, will recognize only the mutant strain.

Advantageously, the method of the invention comprises the detection, in the bacteria to be tested, of the presence or the absence of at least one orphan gene among those cited above, and the detection of at least one of the members of an allelic couple among those cited above.

Still another object of the invention is a method for detecting *E. ruminantium* wherein said method comprises the detection in the bacteria to be tested, of the presence or the absence of any of the members of at least one allelic couple of genes selected among:
SEQ ID NO: 7 and SEQ ID NO: 8;
SEQ ID NO: 9 and SEQ ID NO: 10;
SEQ ID NO: 11 and SEQ ID NO: 12;
SEQ ID NO: 13 and SEQ ID NO: 14+15;
SEQ ID NO: 16 and SEQ ID NO: 17+18;
SEQ ID NO: 19 and SEQ ID NO: 20.

The invention also provides tools for detecting the presence or the absence of the orphan genes listed above, as well as tools for detecting the allelic couples of genes listed above, and differentiating their members.

These tools include in particular isolated polynucleotides defined by the sequences SEQ ID NO: 1 to 20 disclosed above or their complement, as well as fragments of at least 15 consecutive bp, preferably at least 18 consecutive bp, thereof. They also include polynucleotides that hybridize selectively, under stringent hybridization conditions, with one or two of the polynucleotides defined by the sequences SEQ ID NO: 1 to 20 described above, or with the complement thereof, without hybridizing to other sequences within the genome of *Ehrlichia ruminantium*.

A polynucleotide that hybridize selectively with a given target sequence, is herein defined as a polynucleotide which does not hybridize, under the same hybridization conditions, with other sequences within the genome of *Ehrlichia ruminantium*.

Stringent hybridization conditions are defined as conditions that allow hybridization of only highly homologous sequences (i.e sequences having at least 90% and preferably at least 95 to 100% identity). It is known in the art that nucleic-acid hybridization is affected by such conditions as salt concentration, temperature, or organic solvents, in addition to the base composition, length of the complementary strands, and the number of mismatched bases between the hybridizing nucleic acids. Generally, stringent conditions for a given sequence can be obtained by performing hybridization at a temperature of about 10 to 20° C. lower than the melting point ($T_m$) for the hybrid formed by said sequence and its exact complement, and at least one wash at a temperature of about 1 to 10° C. lower, preferably at a temperature of about 1 to 5° C. lower than the $T_m$ for the hybrid formed by said sequence and its exact complement.

The polynucleotides of the invention can be divided in 3 sub-categories:

polynucleotides specific to one of the orphan genes described above: said polynucleotides are fragments of anyone of the sequences SEQ ID NO: 1 to 6 or of its complement, as well as polynucleotides able to hybridize selectively, under stringent conditions, with anyone of the sequences SEQ ID NO: 1 to 6 or with its complement;

polynucleotides common to both members of one of the allelic couples defined above: said polynucleotides are fragments, shared by both members of a given allelic couple, of anyone of the sequences SEQ ID NO: 7 to 20 or of its complement, or polynucleotides able to hybridize selectively, under stringent hybridization conditions, with a region shared by both members of a given allelic couple, of anyone of the sequences SEQ ID NO: 7 to 20 or of its complement. These polynucleotides are useful to detect *E. ruminantium*, and may also be used, as illustrated below, in methods for discriminating between *E. ruminantium* strain Gardel and *E. ruminantium* strain Welgevonden.

polynucleotides specific to one of the members of one of the allelic couples disclosed above: said polynucleotides are fragments of anyone of the sequences SEQ ID NO: 7 to 20 or of its complement, that are present in only one of the members of a given allelic couple, or polynucleotides able to hybridize selectively, under stringent hybridization conditions, with a region of anyone of the sequences SEQ ID NO: 7 to 20 or of its complement, that is present in only one of the members of a given allelic couple. For a given allelic couple, these polynucleotides include those consisting of Zone 2 (or fragments thereof) as well as those spanning the junction between Zone 1 and Zone 3. In the case of a polynucleotide spanning the junction between Zone 1 and Zone 3, it will preferably be chosen in such a way that about half of its sequence is derived from Zone 1 and about half of its sequence is derived from Zone 3.

Polynucleotides of the invention include in particular nucleic acid probes or PCR primers.

For use as PCR primers one will generally chose oligonucleotides of about 18 to 25 bp. A variety of procedures and softwares for designing appropriate primers for a target region are available. Thus, one skilled in the art can easily design, based on the information provided by the present invention, sets of PCR primers suitable to generate an amplification product specific to anyone of the orphan genes listed above, or to generate amplification products from both members of anyone of the allelic couples listed above, or to generate an amplification product from only one of the members of said allelic couple. By way of non-limitative example of oligonucleotide design software suitable for obtaining PCR primers of the invention, one can mention the software Vector NTI Advance 9.0 (Informax).

For use as nucleic acid probes, one will prefer polynucleotides that comprise at least 30 bp, preferably at least 50 bp, and up to the whole length of the target sequence. Many softwares and procedures are available to the one skilled in the art, who can easily design, based on the information provided by the invention, suitable polynucleotides useful for efficiently discriminate *E. ruminantium* strain Gardel from *E. ruminantium* strain Welgevonden.

Polynucleotides of the invention can be DNA, RNA, or synthetic analogs, such as peptide nucleic acids, wherein the ribose phosphodiester backbone of the polynucleotide is replaced with a pseudo-peptide (polyamide) backbone.

They can be obtained by classic methods, well known to the one skilled in the art, such as chemical synthesis, restriction enzyme digestion, by PCR amplification, etc. They can also be labeled, by radioactive or cold labeling. Numerous protocols for polynucleotide synthesis or labeling are well known in the art (cf. for instance Sambrook and Russell, 2001: *Molecular Cloning. A Laboratory Manual,* 3rd Ed., Cold Spring Harbor Laboratory Press, Cold Spring Harbor, N.Y.).

For the purpose of carrying out the invention, the polynucleotides of the invention can be used in many different ways, according to the various techniques for detection of a target nucleic acid sequence based on selective nucleic acid hybridization which are available in the art (cf. for instance Sambrook and Russell, 2001, mentioned above).

The methods of the invention can be performed either on whole bacteria previously lysed, or on nucleic acid (genomic DNA, cDNA or mRNA) isolated from said bacteria.

By way of example, polynucleotides of the invention can be used to detect *E. ruminantium*, and advantageously, to differentiate between *E. ruminantium* strain Gardel from *E. ruminantium* strain Welgevonden, in Southern hybridization, blot hybridization, Northern hybridization, colony hybridization on bacterial colonies, PCR amplification etc. They can be used individually in separate reactions, or they can be combined by 2 or more for use in a same reaction mixture. In this case, they will be labelled in order to be distinguished from each other, and/or they will be spatially separated by immobilization on different spots of a solid phase matrix.

According to a particularly preferred embodiment, polynucleotides of the invention are used as immobilized probes in DNA arrays. For this use, polynucleotides of at least 30 bp, preferably of at least 50 bp will be preferred. Appropriate polynucleotides may be designed from the target sequences provided by the invention, by methods known in themselves, for instance using OligoArray 2.1 (Rouillard et al. Nucleic Acids Research. 31: 3057-3062, 2003).

Non-limitative examples of polynucleotides of the invention that can be used as nucleic acid probes for detecting the orphan genes defined above are: oligo-ERGA-4340, oligo-ERGA-4980, oligo-ERGA-5590, oligo-ERGA-5600, oligo-ERGA-7580, and oligo-ERWE-8330, that respectively hybridize selectively with the orphan genes ERGA_CDS_04340, ERGA_CDS_04980, ERGA_CDS_05590, ERGA_CDS_05600, ERGA_CDS_07580 and ERWE_CDS_08330.

Other non-limitative examples of polynucleotides of the invention that can be used as nucleic acid probes for detecting the same orphan genes are the amplicons PCR-oligo-ERGA-4340, PCR-oligo-ERGA-4980, PCR-oligo-ERGA-5590, PCR-oligo-ERGA-5600, PCR-oligo-ERGA-7580, and PCR-oligo-ERWE-8330 that respectively hybridize selectively with the orphan genes ERGA_CDS_04340, ERGA_CDS_04980, ERGA_CDS_05590, ERGA_CDS_05600, ERGA_CDS_07580 and ERWE_CDS_08330.

The invention also includes nucleic acid probes useful for detecting E. ruminantium through the detection of any of the members of one or several allelic couple(s) of genes defined above. These probes can be directed to the Zone 1 region (P-Z-1 probe), or to the Zone 3 region (P-Z-3 probe), of the targeted allelic couple. A combination of a P-Z-1 probe and of a P-Z-3 probe can also be used.

The invention also includes nucleic acid probes useful for differentiating between E. ruminantium strain Gardel and E. ruminantium strain Welgevonden through the discrimination between the members of one or several allelic couple(s) of genes defined above. These probes are specific for the junction between Zone 1 and Zone 3, or preferably, for the Zone 2 region (P-Z-2 probe) of the targeted allelic couple. They are more particularly useful for discrimination between members of allelic couples where the size of the deletion in zone 2 is sufficiently important to allow its easy detection by DNA hybridization.

These allelic couples include:
the couple consisting of ERGA_CDS_01350 and ERWE_CDS_01390;
the couple consisting of ERGA_CDS_04500 and ERWE_CDS_04590+ERWE_CDS_04600;
the couple consisting of ERGA_CDS_05350 and ERWE_CDS_05460+ERWE_CDS_05470.

According to a preferred embodiment, the invention includes triplets of nucleic acid probes useful for discrimination between members of allelic couples, comprising a probe specific of the Zone 1 region (P-Z-1 probe), a probe specific of the Zone 2 region (P-Z-2 probe), and a probe specific of the Zone 3 region (P-Z-3 probe).

Non limitative examples of said triplets of probes, designated MutERWE multiplexes, comprise the following oligonucleotides:
MutERWE-1390N1, MutERWE-1390N2, and MutERWE-1390N3;
MutERWE-4590N1, MutERWE-4590N2, and MutERWE-4600N3;
MutERWE-5460N1, MutERWE-5460N2, and MutERWE-5460N3.

Advantageously, the nucleic acid probes of the invention are used in DNA arrays allowing to test simultaneously several genes of E. ruminantium, wherein said genes include at least one of the orphan genes defined above, and/or at least one member of any of the allelic couples defined above.

The invention also encompasses said DNA arrays.

DNA arrays of the invention are characterized in that they comprise at least one polynucleotide of the invention of at least 30 bp, preferably at least 50 bp, selected among:
a polynucleotide specific to anyone of the orphan genes defined above;
a polynucleotide common to both members of anyone of the allelic couples defined above (i.e targeted to the Zone 1 or the Zone 3 region of said allelic couple);
a polynucleotide specific to one of the members of anyone of the allelic couples disclosed above (i.e targeted either to the Zone 2 region or to the junction between Zone 1 and Zone 3 of said allelic couple).

Advantageously, DNA arrays of the invention comprise a combination of 2 or more of said polynucleotides.

Thus, DNA arrays of the invention allow to test in an E. ruminantium strain to be analyzed, various combinations of genes that can include from one to all of the orphan genes and/or from one to all of allelic couples defined above.

Non-limitative examples of DNA arrays of the invention are:
i) a DNA array comprising at least one polynucleotide selected among the following: PCR-oligo-ERGA-4340, PCR-oligo-ERGA-4980, PCR-oligo-ERGA-5590, PCR-oligo-ERGA-5600, PCR-oligo-ERGA-7580, and PCR-oligo-ERWE-8330, or any combination of 2, 3, 4, 5, or 6 of these polynucleotides;
ii) a DNA array comprising at least one polynucleotide selected among the following: oligo-ERGA-4340, oligo-ERGA-4980, oligo-ERGA-5590, oligo-ERGA-5600, oligo-ERGA-7580, and oligo-ERWE-8330, or any combination of 2, 3, 4, 5, or 6 of these polynucleotides.
iii) a DNA array comprising at least one polynucleotide selected among the following: MutERWE-1390N2, MutERWE-4590N2, and MutERWE-5460N2;
iv) a DNA array comprising at least one polynucleotide selected among the following: MutERWE-1390N1, MutERWE-1390N3, MutERWE-4590N1, MutERWE-4600N3, MutERWE-5460N1 and MutERWE-5460N3;
v) a DNA array comprising any combination of at least one of the polynucleotides listed in iii) with at least one of the polynucleotides listed in iv);
vi) a DNA array comprising any combination of at least one of the polynucleotides listed in i) or ii) with at least one of the polynucleotides listed in iii) and/or at least one of the polynucleotides listed in iv);

A large range of methods, protocols and techniques exist to develop and probe DNA arrays and read and analyse data. The person expert in the art has easy access to a large literature on the DNA array technology and can easily implement any kind of DNA array approach to identify E. ruminantium, and/or discriminate between E. ruminantium strain Gardel and E. ruminantium strain Welgevonden using information provided in the invention. One can find further information and start a broader literature review if needed from the following references: Lipshutz et al., Nat. Genet. 21: 20-24, 1999; Kiechle and Holland-Staley, Arch. Pathol. Lab. Med. 127: 1089-1097, 2003; Rast et al., Dev Biol. 228: 270-286, 2000; Manduchi et al., Bioinformatics 16: 685-698, 2000; Mäder et al., J. Bacteriol. 184: 4288-4295, 2002; Bowtell, Nat. Genet. 21: 25-32, 1999; WO 2004/061111.

The present invention also includes combinations of polynucleotides of the invention that can be used as sets of PCR primers.

Non limitative examples of sets of primers that can be used to discriminate between *E. ruminantium* strain Gardel and *E. ruminantium* strain Welgevonden by detecting the presence or the absence of the orphan genes described above are: P-ERGA-4340-A/P-ERGA-4340-B; P-ERGA-4980-A/P-ERGA-4980-B; P-ERGA-5590-A/P-ERGA-5590-B; P-ERGA-5600-A/P-ERGA-5600-B; P-ERGA-7580-A/P-ERGA-7580-B; P-ERWE-8330-A/P-ERWE-8330-B.

Other examples of sets of primers of the invention are those which allow depending on the way they are used, either to detect *E. ruminantium*, or to discriminate between *E. ruminantium* strain Gardel and *E. ruminantium* strain Welgevonden.

This type of sets of primers includes combinations of polynucleotides common to both members of anyone of the allelic couples defined above under sequences SEQ ID NO: 7 to 20. Typically, said combinations comprise:
  at least one polynucleotide specific of the region upstream from the mutation (i.e Zone 1); and/or
  at least one polynucleotide specific of the region downstream from the mutation (i.e Zone 3).

These sets of PCR primers allow obtaining an amplification product from both members of the allelic couple. In this case, the discrimination between the native and the mutant allele will be performed on the basis of the difference of size and/or of sequence between the amplification products, by way of example through their RFLP patterns after appropriate enzymatic digestion.

Non-limitative examples of such sets of primers are P-WEGA-120-S/P-WEGA-120-AS; P-WEGA-1350-S/P-WEGA-1350-AS; P-WEGA-4500-S/P-WEGA-4500-AS; P-WEGA-5350-S/P-WEGA-5350-AS; P-WEGA-5740-S/P-WEGA-5740-AS; P-WEGA-7410-S/P-WEGA-7410-AS.

Based on the information provided in the invention, a person skilled in the art can easily design other primers, detect other sequences and select different sets of restriction enzymes. A large range of RFLP strategies and techniques exist, some of them being for instance associated to PCR, to labeled probes, to Southern-blot analysis or to DNA sequencing, and a person expert in the art can easily implement a whole range of approaches to detect *E. ruminantium* or to discriminate between *E. ruminantium* strain Gardel and *E. ruminantium* strain Welgevonden using information from the invention. Similarly, a broad range of techniques exist to obtain, separate and analyze restriction fragments for RFLP analysis. Data provided in example 9 are compatible with any kind of technique for separation and analysis which are well described in the literature and known to a person expert in the art.

Another type of sets of primers of the invention are those which allow to discriminate between *E. ruminantium* strain Gardel and *E. ruminantium* strain Welgevonden, by detecting the presence or the absence of an amplification product.

This type of sets of primers includes polynucleotides common to both members of anyone of the allelic couples defined above under sequences SEQ ID NO: 7 to 20, and polynucleotides specific to one of the members of said allelic couple.

Typically, a combination of this second type comprises:
  at least one polynucleotide specific to the mutated region (i.e Zone 2, or the junction between Zone 1 and Zone 3), and thus specific to one of the members of the allelic couple; and
  at least one polynucleotide common to both members of the allelic couple, and specific of the region upstream from the mutation (i.e the Zone 1); and/or
  at least one polynucleotide common to both members of the allelic couple, and specific of the region downstream from the mutation (i.e the Zone 3).

Examples of such combinations include for instance:
  pairs of primers, where the sense primer recognizes the Zone 1 region (P-Z-1 primer) and the antisense primer recognises the Zone 2 region (P-Z-2-AS primer), or the sense primer recognises the Zone 2 region (P-Z-2-S primer) and the antisense primer recognises the Zone 3 region (P-Z-3-AS primer).
  pairs of primers where the sense primer recognizes the Zone 1 region (P-Z-1 primer) and the antisense primer recognises the junction between Zone 1 and Zone 3 (P-Z-1/3-AS primer), or the sense primer recognises the junction between Zone 1 and Zone 3 (P-Z-1/3-S primer) and the antisense primer recognises the Zone 3 region (P-Z-3-AS primer).

Such combinations are useful for instance to discriminate *E. ruminantium* strain Gardel and *E. ruminantium* strain Welgevonden, by carrying out a simple PCR in parallel on both strains, on the basis of the absence or presence of a PCR product.
  triplets of primers, wherein a sense primer recognizes the Zone 1 region (P-Z-1 primer), a first antisense primer recognises the Zone 2 region (P-Z-2-AS primer), or junction between Zone 1 and Zone 3 (P-Z-1/3-AS primer) and a second antisense primer recognises the Zone 3 region (P-Z-3 region). Such a combination allows discrimination between *E. ruminantium* strain Gardel and *E. ruminantium* strain Welgevonden by multiplex PCR performed in parallel in the 2 strains.

Using such combinations of three primers in the same PCR reaction yields differential patterns for *E. ruminantium* strain Gardel and *E. ruminantium* strain Welgevonden.

Non-limitative examples of such pairs or triplets of primers, and of their use for discriminating *E. ruminantium* strain Gardel from *E. ruminantium* strain Welgevonden by simple PCR and multiplex PCR are:
  P-Z-1-ERGA-120; P-Z-2-ERGA-120-S; P-Z-2-ERGA-120-AS; P-Z-3-ERGA-120;
  P-Z-1-ERGA-1350; P-Z-2-ERGA-1350-S;P-Z-2-ERGA-1350-AS;P-Z-3-ERGA-1350;
  P-Z-1-ERGA-4500;P-Z-2-ERGA-4500-S;P-Z-2-ERGA-4500-AS;P-Z-3-ERGA-4500;
  P-Z-1-ERGA-5350; P-Z-2-ERGA-5350-S;P-Z-2-ERGA-5350-AS;P-Z-3-ERGA-5350;
  P-Z-1-ERGA-5740;P-Z-2-ERGA-5740-S;P-Z-2-ERGA-5740-AS;P-Z-3-ERGA-5740;
  P-Z-1-ERWE-7410;P-Z-2-ERWE-7410-S;P-Z-2-ERWE-7410-ASP-Z-3-ERWE-7410.

For all these primers, an amplification product is obtained only from the native member of the allelic couple when a P-Z-2-S primer or a P-Z-2-AS primer is used.
  P-Z-1-ERGA-4500;P-Z-1/3-ERGA-4500-S; P-Z-1/3-ERGA-4500-AS;P-Z-3-ERGA-4500;

For these primers, an amplification product is obtained only from the mutant member of the allelic couple when a P-Z-1/3-S primer or a P-Z-1/3-AS primer is used.

These combinations are meant to exemplify the approach and do not limit the invention. A person skilled in the art can easily define other primers combinations and/or other primer orientations which will lead to the detection of *E. ruminantium* or to a clear discrimination between *E. ruminantium* strain Gardel and *E. ruminantium* strain Welgevonden.

The invention also comprises diagnostic kits for detecting *E. ruminantium* or for discriminating between strain Gardel and strain Welgevonden of *E. ruminantium*, wherein said kits comprise at least a nucleic acid probe and/or at least a set of primers of the invention.

The polynucleotides of the invention are also useful to produce polypeptides specific of either *E. ruminantium* strain Gardel and *E. ruminantium* strain Welgevonden. Expression of foreign genes in prokaryotic or eukaryotic systems for production of proteins is well known to the expert in the art. A broad range of techniques exist in the literature and/or are available from commercial companies to express foreign genes and produce and purify proteins.

The invention also includes the polypeptides encoded by the sequences SEQ ID NO: 1-20, an in particular the polypeptides encoded by the sequences SEQ ID NO: 1-6, SEQ ID NO: 7, 9, 11, 13, 16, and 20.

The invention also encompasses tools for producing said polypeptides, and in particular:
- a recombinant expression vector comprising a polynucleotide of the invention, selected among the polynucleotides defined by the sequences SEQ ID NO: 1-20, and in particular the polynucleotides defined by the sequences SEQ ID NO: 1-6, SEQ ID NO: 7, 9, 11, 13, 16, and 20;
- an host cell transformed by said expression vector.

The invention also provides, as tools for detecting the orphan genes or the allelic couples of genes listed above, antibodies raised against polypeptides of the invention. Production of polyclonal and monoclonal antibodies is well known to the expert in the art and custom development of antibodies is also provided by companies.

The invention also comprises diagnostic kits for detecting *E. ruminantium* or for discriminating between strain Gardel and strain Welgevonden of *E. ruminantium*, wherein said kits comprise at least a nucleic acid probe and/or at least a set of primers of the invention, or at least an antibody of the invention.

The methods and tools provided by the invention are suitable for use at various stages of the life cycle of *E. ruminantium*, more specifically but not limited to the domestic-ruminants infectious stage, vector-interaction stage or reservoir animals-interaction stage. Preferred utilisations of the methods and tools of the invention include but are not limited to, the detection of *Ehrlichia ruminantium* in a given territory, the strain specific identification of *Ehrlichia ruminantium* in a given territory, the discrimination between strains of *Ehrlichia ruminantium* in a given territory or between different geographical regions, the analysis of strain movements within a region or between geographically distinct regions, the differential presence of strains of *Ehrlichia ruminantium* according to vector species and/or populations or the early detection and risk assessment in regions where potential vectors are present but where the disease has not been recorded yet.

For a better discrimination between *E. ruminantium* strain Gardel from *E. ruminantium* strain Welgevonden, one can advantageously combine the detection of at least one orphan gene or of any combination of orphan genes among those listed herein, with the detection of at least one allelic couple or any combination of allelic couples among those listed herein.

The orphan genes and allelic couples disclosed in the invention are also candidates of choice for the further development of vaccines. Orphan genes and mutant genes are the only genes differing between the strains Gardel and Welgevonden of *E. ruminantium*. Since these two strains do not generate cross protection through vaccination, protective proteins involved must be different in each strain. For instance a protective protein yielding protection against *E. ruminantium* strain Gardel is most likely to be absent or altered in *E. ruminantium* strain Welgevonden, since an animal vaccinated and protected against *E. ruminantium* strain Gardel is not protected and dies when infected with *E. ruminantium* strain Welgevonden. The most obvious group of absent or altered proteins between both strains are those encoded by the orphan or mutant genes. Accordingly, vaccines comprising the polypeptides of the invention proteins will not only protect against heartwater, or cowdriosis, and *E. ruminantium*, but will permit to efficiently protect against non cross-protective strains and prevent the risk of deadly cross-infections.

Specifically exemplified herein is the identification of orphan genes and allelic couples from either or both the strains Gardel and Welgevonden from *Ehrlichia ruminantium*, and the use of PCR primers and nucleic acid probes derived from these genes for the development of DNA arrays, as well as the use of PCR primers derived from these genes for single-pair and multiplex PCR. The use of these primers and probes for differentiating *E. ruminantium* strain Gardel from *E. ruminantium* strain Welgevonden is also exemplified herein.

The genes and CDS described in these examples are designated according to the annotation of the genome sequences of strains Gardel and Welgevonden, which was performed using the GenoAnnot tool of the GenoStar package (www.genostar.org).

Example 1

Lack of Vaccinal Cross-Protection Between *E. ruminantium* Strain Gardel and *E. ruminantium* Strain Welgevonden The strain Gardel of *E. ruminantium* was isolated in Guadeloupe island in 1982 from a goat injected with an homogenate of a female individual of *A. variegatum* collected on cows (Uilenberg et al., Rev. Elev. Méd. Vét. Pays Trop. 34: 34-42, 1985). The strain Welgevonden of *E. ruminantium* was isolated in South Africa in 1985 from mice injected with individually homogenised infected field-collected *A. hebraeum* ticks (Du Plessis, 1985). The strain Welgevonden was multiplied in mice for 8 passages (Du Plessis, 1985). *E. ruminantium* was multiplied on bovine umbilical endothelial cell (BUEC) grown in Glasgow-MEM medium complemented with fetal calf serum, tryptose-phosphate broth and antibiotics (Bezuidenhout et al., J. Vet. Res. 52: 113-120, 1985) at 37° C., 5% $CO_2$ with a weekly reinfection (Martinez et al., Vet. Parasitol. 67: 175-184, 1990). Unlike the Gardel strain, the strain Welgevonden is highly infective to both rodents (mice) and ruminants through intravenous injection.

Vaccination assays were conducted on Creole goats originating from Les Saintes islands, a heartwater-free region of the Caribbean. Pre-bleed sera of all the animals were negative for anti-*Ehrlichia ruminantium* antibodies as determined by an indirect map-1b ELISA (van Vliet et al., J. Clin. Microbiol. 33: 2405-2410, 1995). After attenuated and virulent challenges, rectal temperature of each animal was daily monitored. *E. ruminantium* strain Gardel was attenuated after more than one hundred successive passages on goat endothelial cells. Virulent Gardel preparation (passage 34 and 42) derived from in vitro culture. The supernatant was collected when 70-80% of the cells were lysed by the bacteria for injection to goats. For immunization by infection with ticks and antibiotic treatment, *Amblyomma variegatum* larvae were fed on Gardel *E. ruminantium* infected animal. After moulting, infected nymphs, were engorged on a naive goat which was treated on the third day following hyperthermia with oxytetracycline at a dose of 20 mg/kg of body weight. For immunization with sublethal doses, in vitro *E. ruminantium* strain Gardel preparations (passage 14) were titrated by tissue culture lethal dose 50 (TCLD50) as described previously (Martinez et al., Vet Parasitol. 67: 175-184, 1996). Two-fold serial dilutions of inoculum were prepared to obtain sublethal *E. ruminantium* doses from 10 to 0.625 TCLD50. 5 groups of 5 goats were inoculated i.v. with these doses. Goats which survived following hyperthermia without antibiotic treatment were selected for the experiment.

Goats were vaccinated with *E. ruminantium* strain Gardel using different kinds of vaccines. The first kind of vaccine tested is an attenuated vaccine. In this case, the aggressiveness of the strain was reduced by successive passages on cell culture. In this case, strains are no longer aggressive after 200 serial passages. Strains having undergone less than 100 passages are virulent strains. Attenuated vaccine relies on a strain which is still alive. Another kind of vaccine, inactivated vaccine, was assessed. In this case, the bacteria were killed with sodium azide. Another means of vaccination investigated is infection with pathogenic strains followed by treatments with antibiotics. Animals were infected either with a virulent culture supernatant or by contact with infected ticks. When hyperthermia (fever) appears, the animals are then treated with tetracycline. Another way of vaccinating the animals was to inject sublethal doses of a virulent population and wait for the animal to recover without treatment with antibiotics. Experiments were conducted with animals vaccinated with all the various means of vaccination described above for further homologous or heterologous challenge with a virulent strain.

Vaccination and homologous and heterologous challenge experiments are summarized in Table 1 below.

Apr. 28, 1998 Heterologous challenge with a virulent population of *E. ruminantium* strain Welgevonden (8 passages)—800 µl of culture supernatant were injected intravenously. Hyperthermia appeared 12 days post infection and the animal was treated with antibiotic after 15 days to avoid death. This indicates that the animal was not protected against *E. ruminantium* strain Welgevonden.

Vaccination with Attenuated Vaccine and Serial Challenge (Goat NO 9412)

Feb. 28, 1994 Injection of *E. ruminantium* strain Gardel attenuated after 136 passages. No clinical reaction was observed indicating that the strain injected was not virulent.

Jun. 7, 1994 Homologous challenge with an a virulent population of *E. ruminantium* strain Gardel (42 passages)—2 ml of culture supernatant were injected intravenously.

No clinical reaction was observed, indicating that the animal was protected against *E. ruminantium* strain Gardel.

Mar. 20, 1997 Homologous challenge with a virulent population of *E. ruminantium* strain Gardel (34 passages)—2 ml of culture supernatant were injected intravenously No clinical reaction was observed, indicating that the animal remained protected against *E. ruminantium* strain Gardel after 3 years.

Apr. 28, 1998 Heterologous challenge with a virulent population of *E. ruminantium* strain Welgevonden (8 passages)—800 µl of culture supernatant were injected intravenously. Hyperthermia appeared 12 days post infection. The animal was not treated with antibiotic and death occurred 15 days after infection with *E. ruminantium* strain Welgevonden. This indicates that the animal was not protected against *E. ruminantium* strain Welgevonden.

Vaccination with Sublethal Doses (Goat NO 9642)

Oct. 4, 1996 Infection with a sublethal dose of *E. ruminantium* strain Gardel (0.625 TCLD50 of *E. ruminantium* strain Gardel after 14 passages).

TABLE 1

| | | Vaccination *E. ruminantium* strain Gardel | Homologous challenge *E. ruminantium* strain Gardel | Heterologous challenge *E. ruminantium* strain Welgevonden | |
|---|---|---|---|---|---|
| Goat NO | Vaccine type | Hyperthermia | Hyperthermia | Hyperthermia | Death |
| 9412 | Attenuated | No | No | Yes (12 D.A.I) | Yes (15 D.A.I) |
| 9642 | Attenuated | No | No | Yes (13 D.A.I.) | Yes (15 D.A.I) |
| 9627 | Sublethal dose | Yes | No | Yes (13 D.A.I | Yes (15 D.A.I) |
| 9506 | Infected ticks AB | Yes 10 D.A.I. | No | Yes (12 D.A.I.) | Yes (15 D.A.I) |
| 0037 | | Control | Yes 5 D.A.I. (A.B. to avoid death) | — | — |
| 0038 | | Control | Yes 6 D.A.I. (A.B. to avoid death) | — | — |
| 9707 | | Control | | Yes (12 D.A.I) | Yes (15 D.A.I) |

AB: Treatment with antibiotics
D.A.I: Day After Infection

Experiments were conducted as follows:
Vaccination with Attenuated Vaccine (Goat NO 9642)
Nov. 4, 1996 Injection of *E. ruminantium* strain Gardel attenuated after 224 passages.
No clinical reaction was observed indicating that the strain injected was not virulent.
Mar. 20, 1997 Homologous challenge with a virulent population of *E. ruminantium* strain Gardel (34 passages)—2 ml of culture supernatant were injected intravenously.
No clinical reaction was observed, indicating that the animal was protected against *E. ruminantium* strain Gardel.

Hyperthermia was observed but the animal survived and recovered without treatment with antibiotics.

Mar. 20, 1997 Homologous challenge with a virulent population of *E. ruminantium* strain Gardel (34 passages)—-2 ml of culture supernatant were injected intravenously.

No clinical reaction was observed, indicating that the animal was protected against *E. ruminantium* strain Gardel.

Apr. 28, 1998 Heterologous challenge with a virulent population of *E. ruminantium* strain Welgevonden (8 passages)—800 µl of culture supernatant were injected intravenously.

Hyperthermia appeared 13 days post infection and the animal was treated with antibiotic after 15 days to avoid death. This indicates that the animal was not protected against *E. ruminantium* strain Welgevonden.

Vaccination with Infected Ticks (Goat NO 9506)
Jun. 20, 1996 Infection with ticks infected with *E. ruminantium* strain Gardel.

Hyperthermia was observed 10 days post infection and the animal was treated with antibiotics to avoid death. The animal recovered and survived.

Mar. 20, 1997 Homologous challenge with a virulent population of *E. ruminantium* strain Gardel (34 passages)—2 ml of culture supernatant were injected intravenously.

No clinical reaction was observed, indicating that the animal was protected against *E. ruminantium* strain Gardel.

Apr. 28, 1998 Heterologous challenge with a virulent population of *E. ruminantium* strain Welgevonden (8 passages)—800 µl of culture supernatant were injected intravenously.

Hyperthermia appeared 12 days post infection and the animal was treated with antibiotic after 15 days to avoid death. This indicates that the animal was not protected against *E. ruminantium* strain Welgevonden.

Control for Susceptibility to *E. ruminantium* Strain Gardel (Goats NO 0037 and 038)

Apr. 28, 1998 Infection of naïve goats (not vaccinated) with a virulent population of *E. ruminantium* strain Gardel (32 passages)—500 µl of culture supernatant were injected intravenously.

Hyperthermia appeared 5 and 6 days post infection. Animals were treated with antibiotic to avoid death. This indicates that the animals were susceptible to *E. ruminantium* strain Gardel.

Control for Susceptibility to *E. ruminantium* Strain Welgevonden (Goat NO 9707)

Apr. 28, 1998 Infection of a naïve goat (not vaccinated) with a virulent population of *E. ruminantium* strain Welgevonden (8 passages)—800 µl of culture supernatant were injected intravenously.

Hyperthermia appeared 12 days post infection. The animal was not treated with antibiotic and death occurred 15 days after infection. This indicates that the animals were susceptible to *E. ruminantium* strain Welgevonden.

Example 2

General Features and Sequence Reference

For each strain, purified DNA was broken by sonication to generate fragments of differing sizes. After filling up the ends with Klenow polymerase, DNA fragments ranging from 0.5 kb to 4 kb were separated in a 0.8% agarose gel and collected after gelase (Epicentre) digestion of a cut agarose band. Blunt-end DNA fragments were inserted into pBluescript II KS (Stratagene) digested with EcoRV and dephosphorylated. Ligation was performed with the Fast-Link DNA Ligation kit (Epicentre) and competent DH10B *E. coli* were transformed prior to colony isolation on LB-agar+Ampicillin+Xgal+IPTG. About 15000 clones were isolated for each strain of *E. ruminantium*. Plasmidic DNA from recombinant *E. coli* strains was extracted according to the alkaline lysis method and inserts were sequenced on both strands using universal forward and reverse M13 primers and the ET DYEnamic terminator kit (Amersham). Sequences were obtained with ABI 373 et ABI 377 automated sequencers (Applied Biosystems). Data were analysed and contigs were assembled using Phred-Phrap et Consed software packages (http://www.genome.washington.edu). Gaps were filled in through primer-directed sequencing using custom made primers. A total of about 20000 raw sequence runs were generated and analysed for each *E. ruminantium* strain to generate a full length consensus sequence with a coverage of 6× to 7×.

The genome of *E. ruminantium* strains Gardel and Welgevonden is arranged as a circular chromosome of 1499920 bp and 1512977 bp, respectively. The respective G+C contents for the strains Gardel and Welgevonden is 27.51% and 27.48%. The genome of *E. ruminantium* strain Gardel comprises 948 coding sequences of an average size of 1018 bp which represent a total coding surface of 63% of the whole genome. The genome of *E. ruminantium* strain Welgevonden bears 957 genes of the same average size of 1018 bp. The genome surface of this strain devoted to coding sequences is 62%. Both genomes comprise 36 transfer RNAs (tRNA) and 3 ribosomal RNAs (rRNA).

Example 3

Identification of Orphan Genes in the Gardel and Welgevonden Strains of *E. ruminantium*

The differential analysis of the whole genomes of *E. ruminantium* strains Gardel and Welgevonden showed the presence of coding sequences which are present in only one of the strains and not in the other (orphan gene sequences). Some of the CDS which are unique to *E. ruminantium* strain Gardel and found only in the genome of this strain are presented in Table 2 (Seq ID NO 1 to Seq ID NO 5). One of the CDS which is unique to *E. ruminantium* strain Welgevonden and found only in the genome of this strain is also presented in Table 2 (Seq ID NO 6). Since these sequences are unique to one or the other strain, they clearly represent targets for the differential detection of *E. ruminantium* strain Gardel versus *E. ruminantium* strain Welgevonden.

TABLE 2

| CDS name | SeqID | Size (bp) | Annotated function | Strain |
| --- | --- | --- | --- | --- |
| ERGA_CDS_04340 | Seq ID NO 1 | 186 | unknown | Gardel |
| ERGA_CDS_04980 | Seq ID NO 2 | 270 | unknown | Gardel |
| ERGA_CDS_05590 | Seq ID NO 3 | 630 | unknown | Gardel |
| ERGA_CDS_05600 | Seq ID NO 4 | 828 | unknown | Gardel |
| ERGA_CDS_07580 | Seq ID NO 5 | 303 | unknown | Gardel |
| ERWE_CDS_08330 | Seq ID NO 6 | 225 | unknown | Welgevonden |

Example 4

Identification of Mutant Alleles in the Gardel and Welgevonden Strains of *E. ruminantium*

The differential analysis of the whole genomes of *E. ruminantium* strains Gardel and Welgevonden also showed the presence of coding sequences which are affected by one or several mutations in one of the two strains and for which a non-mutated, functionally active and normal allele is present in the genome of the other strain. These allelic couples of coding sequences are presented in Table 3.

TABLE 3

| Mutant allele in | SEQ ID NO | Size (bp) | Nature of mutation | Native allele in: | SEQ ID NO | Size (bp) | Annotated Function |
|---|---|---|---|---|---|---|---|
| Gardel | | | | Welgevonden | | | |
| ERGA_CDS_07330 | 19 | 3522 | Deletion | ERWE_CDS_07410 | 20 | 4122 | Unknown |
| Welgevonden | | | | Gardel | | | |
| ERWE_CDS_00120 | 8 | 1176 | Deletion | ERGA_CDS_00120 | 7 | 1266 | Unknown |
| ERWE_CDS_01390 | 10 | 2856 | Deletion | ERGA_CDS_01350 | 9 | 3252 | Unknown |
| ERWE_CDS_05830 | 12 | 1659 | Deletion | ERGA_CDS_05740 | 11 | 1836 | Unknown |
| ERWE_CDS_04590 + ERWE_CDS_04600 | 14 + 15 | 873 + 1740 | Deletion + Frameshift | ERGA_CDS_04500 | 13 | 3570 | Unknown |
| ERWE_CDS_05460 + ERWE_CDS_05470 | 17 + 18 | 2361 + 4473 | Deletion + Frameshift | ERGA_CDS_05350 | 16 | 6903 | Unknown |

Example 5

Differential DNA Array Detection of Strains of *E. ruminantium* Based on Recognition of Orphan Genes with Amplicons PCR primers were designed using Vector NTI Advance 9.0 (Informax).

These oligonucleotides are used to produce amplicons by PCR using *E. ruminantium* strain Welgevonden or strain Gardel DNA as template. Oligonucleotides used in this example as PCR primers, and the resulting amplicons are listed in Table 4. The sequence of the PCR primers is indicated in Table 15A.

MgCl2 and 125 µg of DNase in order to remove contaminating host cell DNA. After incubation for 90 min. at 37° C., the reaction is stopped by addition of 25 mM EDTA. Elementary bodies are washed three times in water and lysed by overnight incubation at 55° C. in a solution of 100 mM Tris-HCl (pH 8.0), 150 mM NaCl, 25 mM EDTA, 1.5% SDS and 250 µg/ml of proteinase K. Bacterial DNA is extracted with phenol-chloroform, precipitated with cold ethanol and resuspended in sterile distilled water. Contamination with cell DNA is evaluated by slot blot hybridization using labelled bovine DNA as a probe and dilutions of bovine DNA (12.5 ng and 25 ng) as positive controls.

Amplicons are amplified from DNA extracted from *E. ruminantium* elementary bodies using the primers described

TABLE 4

| Primer name | Orientation | Position relative to CDS | Size (mer) | CDS | Amplicon (size) |
|---|---|---|---|---|---|
| | | Strain Gardel | | | |
| P-ERGA-4340-A | Sense | 1-21 | 21 | ERGA_CDS_04340 | PCR oligo ERGA 4340 (173 bp) |
| P-ERGA-4340-B | Antisense | 153-173 | 21 | ERGA_CDS_04340 | PCR oligo ERGA 4340 (173 bp) |
| P-ERGA-4980-A | Sense | 1-25 | 25 | ERGA_CDS_4980 | PCR oligo ERGA 4980 (218 bp) |
| P-ERGA-4980-B | Antisense | 196-218 | 23 | ERGA_CDS_4980 | PCR oligo ERGA 4980 (218 bp) |
| P-ERGA-5590-A | Sense | 1-20 | 20 | ERGA_CDS_05590 | PCR oligo ERGA 5590 (509 bp) |
| P-ERGA-5590-B | Antisense | 490-509 | 20 | ERGA_CDS_05590 | PCR oligo ERGA 5590 (509 bp) |
| P-ERGA-5600-A | Sense | 56-74 | 19 | ERGA_CDS_05600 | PCR oligo ERGA 5600 (643 bp) |
| P-ERGA-5600-B | Antisense | 677-698 | 22 | ERGA_CDS_05600 | PCR oligo ERGA 5600 (643 bp) |
| P-ERGA-7580-A | Sense | 1-23 | 23 | ERGA_CDS_07580 | PCR oligo ERGA 7580 (239 bp) |
| P-ERGA-7580-B | Antisense | 221-239 | 19 | ERGA_CDS_07580 | PCR oligo ERGA 7580 (239 bp) |
| | | Strain Welgevonden | | | |
| P-ERWE-8330-A | Sense | 14-38 | 25 | ERWE_CDS_08330 | PCR oligo ERWE 8330 (180 bp) |
| P-ERWE-8330-B | Antisense | 173-193 | 21 | ERWE_CDS_08330 | PCR oligo ERWE 8330 (180 bp) |

Preparation of the Amplicons

DNA is extracted from elementary bodies of *E. ruminantium* as described by Perez et al. (FEMS Microbiol. Lett. 154: 73-79, 1997). *E. ruminantium* strains are grown in BUEC cells as described in Example 1 above. Elementary bodies are purified from the culture supernatant by differential centrifugation and resuspended in 350l of PBS to which is added 150 µl of buffer containing 25 mM Tris-HCl (pH 8.0), 10 mM in Table 4. A standard procedure is used to obtain the amplicons through PCR (Sambrook & Russel, "Molecular Cloning: a laboratory manual", $3^{rd}$ Edition, vol. 2, Chapter 8). PCR amplification of amplicons are obtained by mixing 250 ng of *E. ruminantium* DNA, 2.5 U of Taq DNA polymerase, 200 nM of each dNTP, 1 µM of each, sense and antisense, primer and 3 mM $MgCl_2$ in a final volume of 50 µl. Amplification is carried out under the following conditions: 5 min denaturation at 94° C., followed by 30 cycles of amplification with a 1-min denaturation, 45 sec of annealing at 45° C. and 2 min extension at 72° C. An extra extension step of 10 min at 72° C. is added after completion of the 30 cycles. PCR products, i.e. amplicons, are analysed by 1% agarose gel electrophoresis in Tris-borate-EDTA buffer.

Table 5 below indicates the size and position of the amplicons relative to the corresponding CDS.

TABLE 5

| Amplicon | | | CDS | |
|---|---|---|---|---|
| Name | Size | Position relative to CDS | Name | Size |
| Strain Gardel | | | | |
| PCR-oligo-ERGA-4340 | 173 bp | 1-173 | ERGA_CDS_04340 | 186 bp |
| PCR-oligo-ERGA-4980 | 218 bp | 1-218 | ERGA_CDS_04980 | 270 bp |
| PCR-oligo-ERGA-5590 | 509 bp | 1-509 | ERGA_CDS_05590 | 630 bp |
| PCR-oligo-ERGA-5600 | 643 bp | 56-698 | ERGA_CDS_05600 | 828 bp |
| PCR-oligo-ERGA-7580 | 239 bp | 1-239 | ERGA_CDS_07580 | 303 bp |
| Strain Welgevonden | | | | |
| PCR-oligo-ERWE-8330 | 180 bp | 14-193 | ERWE_CDS_08330 | 225 bp |

Preparation of DNA Microarrays

Amplicons are spotted using the Amersham Biosciences Lucidea Array spotter on aminosilane-coated mirror glass slides (7 Star, Amersham Biosciences) following the procedure recommended by the supplier. Negative and positive control DNAs are also printed into 24 different sectors of each slide. After printing, the slides are stored at room temperature in a dessicator. Prior to hybridization, DNA is cross-linked to the slides by UV irradiation, washed twice with 0.2% SDS solution and rinsed twice with distilled water.

Preparation of Labelled DNA from *E. ruminantium*

DNA is extracted from elementary bodies of *E. ruminantium* strain Gardel or strain Welgevonden as described above in this example. Purified DNA is fragmented by sonication as follows. A 500-μl DNA solution in TE buffer (10 mM Tris-HCl pH8.0, 0.3 mM EDTA) is sonicated for 3 cycles of 1 min each at amplitude 5. Samples are placed on ice while sonicated. Samples are incubated on ice for 1 min and centrifuged briefly to concentration the solution on the bottom of the tube after each cycle of sonication. The size of DNA fragments is checked by 1% agarose-gel electrophoresis under standard conditions. Preferred samples are ranging between 0.3 and 0.5 kb in size. Sonicated DNA from *E. ruminantium* strains Gardel and Welgevonden are labelled with different dyes. DNA from *E. ruminantium* Gardel is labelled with Cy3-dCTP (Amersham Biosciences) whereas *E. ruminantium* Welgevonden is labelled with Cy5-dCTP (Amersham Biosciences). In both cases DNA is labelled by random priming (BioPrime Array CGH Genomic labeling System from Invitrogen) following the procedure recommended by the supplier. 1 μg of sonicated DNA in 21 μl of sterile distilled water is mixed with 20 μl of the random primers solution and incubated at 95° C. for 5 min and immediately cooled on ice. Still on ice, the following reagents are added: 5 μL of 10×dCTP nucleotide mix, 3 μl of Cy3-dCTP (or 3 μl of Cy5-dCTP depending on the strain), 1 μl of exo-klenow fragment enzyme. The solution is mixed and quickly spinned down prior to incubation at 37° C. for 2 hours. Reaction is stopped by addition of 5 μl of stop buffer. Probes are purified through purification columns as recommended by the supplier of the kit. 45 μl of TE buffer are added as well as 400 μl of purification buffer A. Solution is vortexed for 30 sec and loaded on a purification column within a collection tube. The column is centrifuged at 11000 g for 1 min at room temperature and the flow-through is discarded. 600 μl of purification buffer B are added to the column prior to centrifugation at 11000 g for 1 min at room temperature and the flow-through is discarded. The purification column is placed in another collection tube and 50 μl of sterile distilled water is added. The column is incubated 1 min at room temperature and centrifuged at 11000 g for 1 min at room temperature. The flow-through contains the purified probe. *E. coli* DNA prepared and labelled in the very same way is used as control. When using Cy3-labelled DNA from *E. ruminantium* Gardel, the *E. coli* control DNA is labelled with Cy5-dCTP, whereas when using Cy5-labelled DNA from *E. ruminantium* Welgevonden, the *E. coli* control DNA is labelled with Cy3-dCTP.

Hybridization of DNA to the Microarrays

The labelled DNA preparations, samples and control, (0.9-1.2 μg per strain) are denaturated at 95° C. for 5 min. They are subsequently added to microarray hybridization buffer (Amersham Biosciences) and are applied to the microarrays in individual chambers of an automated slide processor (Amersham Biosciences). Hybridization is carried out at 42° C. for PCR array (or 37° C. for oligos array) for 12 h. Hybridized slides are washed at 45° C. successively with 1×SSC, 0.2% SDS for 10 min, twice with 0.1×SSC, 0.2% SDS for 10 min, with 0.1×SSC for 1 min and with isopropanol before air drying. Microarrays are immediately scanned in both Cy3 and Cy5 channels with Amersham generation III array scanner with a 10 μm resolution.

Results

DNA from strain Gardel hybridizes with all the spots of the micro-array bearing the amplicons PCR-oligo-ERGA-4340, PCR-oligo-ERGA-4980, PCR-oligo-ERGA-5590, PCR-oligo-ERGA-5600, PCR-oligo-ERGA-7580 and does not hybridizes with the spots bearing the amplicon PCR-oligo-ERWE-8330. On the other hand, DNA from strain Welgevonden hybridizes only with the spot bearing the amplicon PCR-oligo-ERWE-8330

These results show that *E. ruminantium* strain Gardel can be specifically discriminated from *E. ruminantium* strain Welgevonden using any combination from 1 to 6 of these amplicons.

Example 6

Differential DNA Array Detection of Strains of *E. ruminantium* Based on Recognition of Orphan Genes with Oligonucleotides This example is based on the use of oligonucleotide probes specific to the orphan genes to be detected. Oligonucleotides were designed using OligoArray 2.1 (Rouillard et al., Nucleic Acids Research. 31: 3057-3062, 2003). Table 6 below indicates the size of these oligonucleotides and their positions relative to the corresponding CDS.

TABLE 6

| Oligonucleotide | | | CDS recognized |
|---|---|---|---|
| Name | Size (bp) | Position relative to CDS sequence | by the oligonucleotide |
| Oligo-ERGA-4340 | 50 | 137-186 | ERGA_CDS_04340 |
| Oligo-ERGA-4980 | 51 | 180-230 | ERGA_CDS_04980 |
| Oligo-ERGA-5590 | 50 | 561-610 | ERGA_CDS_05590 |
| Oligo-ERGA-5600 | 50 | 710-759 | ERGA_CDS_05600 |
| Oligo-ERGA-7580 | 50 | 194-243 | ERGA_CDS_07580 |
| Oligo-ERWE-8330 | 51 | 35-85 | ERWE_CDS_08330 |

To prepare DNA arrays, the oligonucleotides are spotted on aminosilane-coated mirror glass slides (7 Star, Amersham Biosciences) following the procedure described for amplicons in Example 5 above. Labelled DNAs from *E. ruminantium* strain Gardel or *E. ruminantium* strain Welgevonden are prepared and hybridized to said arrays as disclosed in Example 5 above.

DNA from strain Gardel hybridizes with all the spots of the micro-array bearing the oligonucleotides Oligo-ERGA-4340, Oligo-ERGA-4980, Oligo-ERGA-5590, Oligo-ERGA-5600, Oligo-ERGA-7580 and does not hybridize with the spot bearing the oligonucleotide Oligo-ERWE-8330. On the other hand, DNA from strain Welgevonden hybridizes only with the spot bearing the oligonucleotide Oligo-ERWE-8330.

Thus *E. ruminantium* strain Gardel can be specifically discriminated from *E. ruminantium* strain Welgevonden using any combination from 1 to 6 of these oligonucleotides.

Example 7

Differential DNA Array Detection of Strains of *E. ruminantium* Based on Recognition of Mutated Genes with Oligonucleotides The genes targeted in this example are truncated genes for which part of the transcribed region is lost in the central part of the initial coding sequence. Three main regions can therefore be considered. The first region, named Zone 1, is the 5' region of the gene up to the beginning of the deletion in the mutated gene. Zone 1 is a conserved region of high similarity between *E. ruminantium* strain Gardel and *E. ruminantium* strain Welgevonden. An oligonucleotide designed to match this region (N1) recognizes both strains. Zone 2, corresponds to the region of deletion in the mutant allele and therefore only the native full length allele bears a sequence in this region and can be recognized by an oligonucleotide (N2). Zone 3 is the second conserved region of high similarity between *E. ruminantium* strain Gardel and *E. ruminantium* strain Welgevonden. In this region also, an oligonucleotide designed to match Zone 3 (N3) recognizes both strains.

Oligonucleotides probes targeted to Zone 1, Zone 2, and Zone 3 of each of the allelic couples:

ERGA_CDS_01350/ERWE_CDS_01390,
ERGA_CDS_04500/(ERWE_CDS_04590+ERWE_CDS_4600)
ERGA_CDS_05350/(ERWE_CDS_05460+ERWE_CDS_5470)

were designed using OligoArray 2.1 (Rouillard et al., cited above). Table 7 below indicates the size of these oligonucleotides and their positions relative to the corresponding CDS. The sequence of these oligonucleotides is indicated in Table 15A.

TABLE 7

| Oligonucleotide name | Zone | Size (mer) | Position relative to CDS | Mutant allele | Position relative to CDS | Native allele |
|---|---|---|---|---|---|---|
| MutERWE-1390N1 | 1 | 50 | 507-556 | ERWE_CDS_01390 | 507-556 | ERGA_CDS_01350 |
| MutERWE-1390N2 | 2 | 50 | — | ERWE_CDS_01390 | 2328-2377 | ERGA_CDS_01350 |
| MutERWE-1390N3 | 3 | 50 | 2771-2820 | ERWE_CDS_01390 | 3167-3216 | ERGA_CDS_01350 |
| MutERWE-4590N1 | 1 | 50 | 455-504 | ERWE_CDS_04590 | 449-498 | ERGA_CDS_04500 |
| MutERWE-4590N2 | 2 | 50 | — | ERWE_CDS_04590 | 536-585 | ERGA_CDS_04500 |
| MutERWE-4600N3 | 3 | 50 | 962-1011 | ERWE_CDS_04600 | 2777-2826 | ERGA_CDS_04500 |
| MutERWE-5460N1 | 1 | 50 | 2251-2300 | ERWE_CDS_05460 | 6793-6842 | ERGA_CDS_05350 |
| MutERWE-5460N2 | 2 | 50 | — | ERWE_CDS_05460 | 5455-5504 | ERGA_CDS_05350 |
| MutERWE-5470N3 | 3 | 50 | 3440-3489 | ERWE_CDS_05470 | 3440-3489 | ERGA_CDS_05350 |

These oligonucleotides can be used as oligonucleotide multiplexes for DNA array detection of *E. ruminantium* strain Gardel and *E. ruminantium* strain Welgevonden. These oligonucleotide multiplexes are listed in Table 8 below.

TABLE 8

| Mut oligonucleotide mutiplexes | Oligonucleotides | Mutant allele | Native allele | Zone |
|---|---|---|---|---|
| MutERWE-1390 | MutERWE 1390N1 | ERWE_CDS_01390 | ERGA_CDS_01350 | 1 |
| | MutERWE 1390N2 | ERWE_CDS_01390 | ERGA_CDS_01350 | 2 |
| | MutERWE 1390N3 | ERWE_CDS_01390 | ERGA_CDS_01350 | 3 |
| MutERWE-4590/4600 | MutERWE 4590N1 | ERWE_CDS_04590 | ERGA_CDS_04500 | 1 |
| | MutERWE 4590N2 | ERWE_CDS_04590 | ERGA_CDS_04500 | 2 |
| | MutERWE 4600N3 | ERWE_CDS_04600 | ERGA_CDS_04500 | 3 |
| MutERWE-5460/5470 | MutERWE 5460N1 | ERWE_CDS_05460 | ERGA_CDS_05350 | 1 |
| | MutERWE 5460N2 | ERWE_CDS_05460 | ERGA_CDS_05350 | 2 |
| | MutERWE 5470N3 | ERWE_CDS_05470 | ERGA_CDS_05350 | 3 |

To prepare DNA arrays, the oligonucleotides are spotted on aminosilane-coated mirror glass slides following the procedure described for amplicons in Example 5 above. Labelled DNAs from *E. ruminantium* strain Gardel or *E. ruminantium* strain Welgevonden are prepared and hybridized to said arrays as disclosed in Example 5 above.

A differential analysis on both strains is carried out by running a separate reaction for each oligonucleotide, N1, N2 and N3 in each strain making a total of six separate reactions, each on a specific spot (six separate spots). All members of the series hybridize with DNA from the strain bearing the native full length allele yielding three positive responses. The N1 and N3 oligonucleotides specific to the conserved Zone 1 and 3 hybridize with DNA from the strains bearing the mutation. The N2 oligonucleotide specific to the deleted region (Zone 2) does not hybridize onto the stain bearing the mutation and yields a negative response. A typical pattern for the strain bearing the mutation is a positive response for oligonucleotide N1 and N3 and a negative response for oligonucleotide N2.

The Mut oligonucleotide series described in this example allow differential discrimination between *E. ruminantium* strain Gardel and *E. ruminantium* strain Welgevonden through DNA arrays on three different genes with three different series of three oligonucleotides. This provides a high level of confidence in the specific identification of each strain.

Example 8

Differential PCR Detection of Strains of *E. ruminantium*

This example illustrates the discrimination between *E. ruminantium* strain Gardel and *E. ruminantium* strain Welgevonden based on the differential PCR amplification of native and mutant alleles of 6 different genes:

ERGA_CDS_00120/ERWE_CDS_00120
ERGA_CDS_01350/ERWE_CDS_01390
ERGA_CDS_05740/ERWE_CDS_05830
ERGA_CDS_04500/(ERWE_CDS_04590+ERWE_CDS_4600)
ERGA_CDS_05350/(ERWE_CDS_05460+ERWE_CDS_5470)
ERGA_CDS_07330/ERWE_CDS_07410

Primers were designed using Vector NTI Advance 9.0 (Informax).

Table 9 below provides a list of these primers and indicates their positions relative to the corresponding CDS. The sequence of these PCR primers is indicated in Table 15B.

TABLE 9

| Primer (orientation) | Zone | Position relative to CDS | Native allele | Position relative to CDS | Mutant allele |
|---|---|---|---|---|---|
| P-Z-1-ERGA-120 (sense) | 1 | 5-29 | ERGA_CDS_00120 | 5-29 | ERWE_CDS_00120 |
| P-Z-2-ERGA-120-S (sense) | 2 | 442-466 | ERGA_CDS_00120 | — | ERWE_CDS_00120 |
| P-Z-2-ERGA-120-AS (antisense) | 2 | 442-466 | ERGA_CDS_00120 | — | ERWE_CDS_00120 |
| P-Z-3-ERGA-120 (antisense) | 3 | 1222-1246 | ERGA_CDS_00120 | 1132-1156 | ERWE_CDS_00120 |
| P-Z-1-ERGA-1350 (sense) | 1 | 240-264 | ERGA_CDS_01350 | 240-264 | ERWE_CDS_01390 |
| P-Z-2-ERGA-1350-S (sense) | 2 | 2344-2368 | ERGA_CDS_01350 | — | ERWE_CDS_01390 |
| P-Z-2-ERGA-1350-AS (antisense) | 2 | 2344-2368 | ERGA_CDS_01350 | — | ERWE_CDS_01390 |
| P-Z-3-ERGA-1350 (antisense) | 3 | 3007-3031 | ERGA_CDS_01350 | 2611-2635 | ERWE_CDS_01390 |
| P-Z-1-ERGA-4500 (sense) | 1 | 301-325 | ERGA_CDS_04500 | 307-331 | ERWE_CDS_04590 |
| P-Z-2-ERGA-4500-S (sense) | 2 | 548-572 | ERGA_CDS_04500 | — | ERWE_CDS_04590 |
| P-Z-2-ERGA-4500-AS (antisense) | 2 | 548-572 | ERGA_CDS_04500 | — | ERWE_CDS_04590 |
| P-Z-3-ERGA-4500 (antisense) | 3 | 829-853 | ERGA_CDS_04500 | 775-799 | ERWE_CDS_04590 |
| P-Z-1-ERGA-5350 (sense) | 1 | 4525-4549 | ERGA_CDS_05350 | 223-247 | ERWE_CDS_05460 |
| P-Z-2-ERGA-5350-S (sense) | 2 | 5466-5491 | ERGA_CDS_05350 | — | ERWE_CDS_05460 |
| P-Z-2-ERGA-5350-AS (antisense) | 2 | 5466-5491 | ERGA_CDS_05350 | — | ERWE_CDS_05460 |
| P-Z-3-ERGA-5350 (antisense) | 3 | 6071-6095 | ERGA_CDS_05350 | 1532-1556 | ERWE_CDS_05460 |
| P-Z-1-ERGA-5740 (sense) | 1 | 443-467 | ERGA_CDS_05740 | 449-473 | ERWE_CDS_05830 |
| P-Z-2-ERGA-5740-S (sense) | 2 | 1376-1400 | ERGA_CDS_05740 | — | ERWE_CDS_05830 |
| P-Z-2-ERGA-5740-AS (antisense) | 2 | 1376-1400 | ERGA_CDS_05740 | — | ERWE_CDS_05830 |
| P-Z-3-ERGA-5740 (antisense) | 3 | 1780-1804 | ERGA_CDS_05740 | 1603-1627 | ERWE_CDS_05830 |
| P-Z-1-ERWE-7410 (sense) | 1 | 151-175 | ERWE_CDS_07410 | 151-175 | ERGA_CDS_07330 |
| P-Z-2-ERWE-7410-S (sense) | 2 | 639-663 | ERWE_CDS_07410 | — | ERGA_CDS_07330 |

TABLE 9-continued

| Primer (orientation) | Zone | Position relative to CDS | Native allele | Position relative to CDS | Mutant allele |
|---|---|---|---|---|---|
| P-Z-2-ERWE-7410-AS (antisense) | 2 | 639-663 | ERWE_CDS_07410 | — | ERGA_CDS_07330 |
| P-Z-3-ERWE-120 (antisense) | 3 | 1818-1843 | ERWE_CDS_07410 | 1222-1246 | ERGA_CDS_07330 |

P-Z-1 and P-Z-3 primers recognize the conserved regions Zone 1 and Zone 3, respectively, in both *E. ruminantium* strain Gardel and *E. ruminantium* strain Welgevonden. P-Z-2 primers are specifically binding to Zone 2 in the native full length allele and do not hybridise to the genome of the strain bearing the corresponding mutant allele.

In this example, P-Z-1 primers are sense primers whereas P-Z-3 primers are antisense primers. Two kinds of P-Z-2 primers are used, sense primer (labelled -S) and antisense primers (labelled -AS). They recognized the same region but on complementary strands and directed amplification in opposite orientations.

Two different ways of use of these primers are exemplified herein: simple PCR and multiplex PCR.

Simple PCR

DNA is extracted from *E. ruminantium* elementary bodies, as described in example 5 above. Simple direct PCR is performed using a standard procedure (Sambrook & Russel, Molecular Cloning "a laboratory manual", 3$^{rd}$ Edition, vol. 2, Chapter 8).

250 ng of *E. ruminantium* DNA, 2.5 U of Taq DNA polymerase, 200 nM of each dNTP, 1 µM of each, sense and antisense, primer and 3 mM MgCl$_2$ are mixed in a final volume of 50 µl. Amplification is done under the following conditions: 5 min denaturation at 94° C., followed by 30 cycles of amplification with a 1-min denaturation, 45 sec of annealing at 45° C. and 2 min extension at 72° C. An extra extension step of 10 min at 72° C. is added after completion of the 30 cycles. PCR products are analysed by 1% agarose gel electrophoresis in Tris-borate-EDTA buffer.

The amplification patterns obtained using three different pairs of primers (P-Z-1+P-Z-3, P-Z-1+P-Z-2-AS and P-Z-3+P-Z-2-S) are shown in Table 10.

For each doublet of native and mutant alleles, *E. ruminantium* strain Gardel and *E. ruminantium* strain Welgevonden can be discriminated according to the expected size of the amplification products.

Multiplex PCR:

Differential detection through multiplex PCR is performed on DNA prepared from *E. ruminantium* elementary bodies as described in Example 5 above.

For each couple of allele, the multiplex PCR is carried out by mixing 250 ng of *E. ruminantium* DNA, 2.5 U of Taq DNA polymerase, 200 nM of each dNTP, 1 µM of P-Z-1 primer, 0.5 µM of P-Z-2 primer, 0.5 µM of P-Z-3 primer and 3 mM MgCl$_2$ in a final volume of 50 µl. Amplification is done under the following conditions: 5 min denaturation at 94° C., followed by 30 cycles of amplification with a 1-min denaturation, 45 sec of annealing at 45° C. and 2 min extension at 72° C. An extra extension step of 10 min at 72° C. is added after completion of the 30 cycles. PCR products, i.e. doublets, are analysed by 1% agarose gel electrophoresis in Tris-borate-EDTA buffer.

The use, for any of the targeted gene, of a P-Z-1 sense primer and two antisense primers, i.e. P-Z-2-AS and P-Z-3, generates two PCR products of differing size in the same reaction when the gene present in the strain is the native full length allele. These two PCR products correspond to an amplification driven by the P-Z-1/P-Z-2-AS pair and by the P-Z-1/P-Z-3 pair. When a mutant allele is present, the PCR reaction generates only one amplification product driven by the P-Z-1/P-Z-3 pair.

The amplification patterns obtained on *E. ruminantium* strain Gardel and *E. ruminantium* strain Welgevonden are shown in Table 11.

TABLE 10

| Primer pairs | *E. ruminantium* strain Gardel (size) | *E. ruminantium* strain Welgevonden (size) |
|---|---|---|
| P-Z-1-ERGA-120 + P-Z-3-ERGA-120 | Positive (1242 bp) | Positive (1152 bp) |
| P-Z-1-ERGA-120 + P-Z-2-ERGA-120-AS | Positive (462 bp) | Negative |
| P-Z-3-ERGA-120 + p-Z-2-ERGA-120-S | Positive (805 bp) | Negative |
| P-Z-1-ERGA-1350 + P-Z-3-ERGA-1350 | Positive (2792 bp) | Positive (2396 bp) |
| P-Z-1-ERGA-1350 + P-Z-2-ERGA-1350-AS | Positive (2129 bp) | Negative |
| P-Z-3-ERGA-1350 + P-Z-2-ERGA-1350-S | Positive (688 bp) | Negative |
| P-Z-1-ERGA-4500 + P-Z-3-ERGA-4500 | Positive (553 bp) | Positive (493 bp) |
| P-Z-1-ERGA-4500 + P-Z-2-ERGA-4500-AS | Positive (272 bp) | Negative |
| P-Z-3-ERGA-4500 + P-Z-2-ERGA-4500-S | Positive (306 bp) | Negative |
| P-Z-1-ERGA-5350 + P-Z-3-ERGA-5350 | Positive (1571 bp) | Positive (1334 bp) |
| P-Z-1-ERGA-5350 + P-Z-2-ERGA-5350-AS | Positive (967 bp) | Negative |
| P-Z-3-ERGA-5350 + P-Z-2-ERGA-5350-AS | Positive (630 bp) | Negative |
| P-Z-1-ERGA-5740 + P-Z-3-ERGA-5740 | Positive (1362 bp) | Positive (1179 bp) |
| P-Z-1-ERGA-5740 + P-Z-2-ERGA-5740-AS | Positive (958 bp) | Negative |
| P-Z-3-ERGA-5740 + P-Z-2-ERGA-5740-S | Positive (429 bp) | Negative |
| P-Z-1-ERWE-7410 + P-Z-3-ERWE-7410 | Positive (1096 bp) | Positive (1693 bp) |
| P-Z-1-ERWE-7410 + P-Z-2-ERWE-7410-AS | Negative | Positive(513 bp) |
| P-Z-3-ERWE-7410 + P-Z-2-ERWE-7410-S | Negative | Positive(1205 bp) |

TABLE 11

| Primer triplets | E. ruminantium strain Gardel (size) | E. ruminantium strain Welgevonden (size) |
|---|---|---|
| P-Z-1-ERGA-120 + P-Z-2-ERGA-120-AS + P-Z-3-ERGA-120 | 2 PCR products (1242 bp and 462 bp) | 1 PCR product (1172 bp) |
| P-Z-1-ERGA-1350 + P-Z-2-ERGA-1350-AS + P-Z-3-ERGA-1350 | 2 PCR products (2792 bp and 2129 bp) | 1 PCR product (2396 bp) |
| P-Z-1-ERGA-4500 + P-Z-2-ERGA-4500-AS + P-Z-3-ERGA-4500 | 2 PCR products (553 bp and 272 bp) | 1 PCR product (493 bp) |
| P-Z-1-ERGA-5350 + P-Z-2-ERGA-5350-AS + P-Z-3-ERGA-5350 | 2 PCR products (1571 bp and 967 bp) | 1 PCR product (1334 bp) |
| P-Z-1-ERGA-5740 + P-Z-2-ERGA-5740-AS + P-Z-3-ERGA-5740 | 2 PCR products (1362 bp and 958 bp) | 1 PCR product (1179 bp) |
| P-Z-1-ERWE-7410 + P-Z-2-ERWE-7410-AS + P-Z-3-ERWE-7410 | 1 PCR product (1096 bp) | 2 PCR products (1693 bp and 513 bp) |

In the same way as for the simple PCR described above, *E. ruminantium* strain Gardel and *E. ruminantium* strain Welgevonden can be discriminated according to the size of the amplification products.

Example 9

Differential Discrimination Between *E. ruminantium* Strain Gardel and *E. ruminantium* Strain Welgevonden Based on RFLP and Sequence Analysis-Related Means This example illustrates the discrimination between *E. ruminantium* strain Gardel and *E. ruminantium* strain Welgevonden by PCR amplification of the members of same couples of genes as in example 8, followed by RFLP analysis of the amplification products.

Primers targeted to sequences that are present in both *E. ruminantium* strain Gardel and *E. ruminantium* strain Welgevonden and giving amplification products of different sizes depending on the strain, were designed using Vector NTI Advance 9.0 (Informax).

Table 12 below provides a list of these primers and indicates their positions relative to the corresponding CDS. The sequence of these PCR primers is indicated in Table 15B.

PCR Amplification

PCR amplification is carried out, for each couple of allele, by mixing 250 ng of *E. ruminantium* DNA, 2.5 U of Taq DNA polymerase, 200 nM of each dNTP, 1 μM of each, sense (S) and antisense (AS) primer, and 3 mM $MgCl_2$ in a final volume of 50 μl. Amplification is done under the following conditions: 5 min denaturation at 94° C., followed by 30 cycles of amplification with a 1-min denaturation, 45 sec of annealing at 45° C. and 2 min extension at 72° C. An extra extension step of 10 min at 72° C. is added after completion of the 30 cycles. PCR products are checked by running an aliquot on 1% agarose gel electrophoresis in Tris-borate-EDTA buffer.

The P-WEGA-120-S/P-WEGA-120-AS pair directs the amplification of a 1261 bp PCR product from ERGA_CDS__00120 in *E. ruminantium* strain Gardel (i.e. RFLP-ERGA-120) and a 1171 bp PCR product from ERWE_CDS__00120 in *E. ruminantium* strain Welgevonden (i.e. RFLP-ERWE-120).

The P-WEGA-1350-S/P-WEGA-1350-AS pair yields a 1482 bp PCR product from ERGA_CDS__01350 in *E. ruminantium* strain Gardel (i.e. RFLP-ERGA-1350) and a 1086 bp PCR product from ERWE_CDS__1390 in *E. ruminantium* strain Welgevonden (i.e. RFLP-ERWE-1390).

The P-WEGA-4500-S/P-WEGA-4500-AS pair drives amplification of a 3265 bp PCR product from ERGA_CDS-04500 in *E. ruminantium* strain Gardel (RFLP-ERGA-4500) and a 2675 bp PCR product from ERWE_CDS-04590/ERWE_CDS__04600 in *E. ruminantium* strain Welgevonden (i.e. RFLP-ERWE-4590/4600).

The P-WEGA-5350-S/P-WEGA-5350-AS pair drives amplification of a 2739 bp PCR product from ERGA_CDS-05350 in *E. ruminantium* strain Gardel (RFLP-ERGA-05350) and a 2765 bp PCR product from ERWE_CDS-05460/ERWE_CDS__05470 in *E. ruminantium* strain Welgevonden (i.e. RFLP-ERWE-5460/5470).

The P-WEGA-5740-S/P-WEGA-5740-AS pair drives amplification of a 1566 bp PCR product from ERGA_CDS-05740 in *E. ruminantium* strain Gardel (RFLP-ERGA-05740) and a 1386 bp PCR product from ERWE_CDS-05830 in *E. ruminantium* strain Welgevonden (RFLP-ERWE-5830).

Similarly, P-WEGA-7410-S/P-WEGA-7410-AS pair drives amplification of a 1389 bp PCR product from ERGA_CDS-07330 (RFLP-ERGA-07330), and a 1986 bp PCR product from ERWE_CDS-07410 in *E. ruminantium* strain Welgevonden (RFLP-ERWE-7410).

TABLE 12

| Primers | Orientation | Position relative to CDS Strain Gardel | Position relative to CDS Strain Welgevonden |
|---|---|---|---|
| P-WEGA-120-S | Sense | 1-25 (ERGA__CDS__00120) | 1-25 (ERWE__CDS__00120) |
| P-WEGA-120-AS | Antisense | 1237-1261 (ERGA__CDS__00120) | 1147-1171 (ERWE__CDS__00120) |
| P-WEGA-1350-S | Sense | 1430-1454 (ERGA__CDS__01350) | 1430-1454 (ERWE__CDS__01390) |
| P-WEGA-1350-AS | Antisense | 2887-2911 (ERGA__CDS__01350) | 2491-2515 (ERWE__CDS__01390) |
| P-WEGA-4500-S | Sense | 301-325 (ERGA__CDS__04500) | 307-331 (ERWE__CDS__04590) |
| P-WEGA-4500-AS | Antisense | 3541-3565 (ERGA__CDS__04500) | 1711-1735 (ERWE__CDS__04600) |
| P-WEGA-5350-S | Sense | 3365-3389 (ERGA__CDS__05350) | 3365-3389 (ERWE__CDS__05470) |
| P-WEGA-5350-AS | Antisense | 6079-6103 (ERGA__CDS__05350) | 1540-1564 (ERWE__CDS__05460) |
| P-WEGA-5740-S | Sense | 241-268 (ERGA__CDS__05740) | 244-271 (ERWE__CDS__05830) |
| P-WEGA-5740-AS | Antisense | 1779-1806 (ERGA__CDS__05740) | 1602-1629 (ERWE__CDS__05830) |
| P-WEGA-7410-S | Sense | 1-25 (ERGA__CDS__07330) | 1-25 (ERWE__CDS__07410) |
| P-WEGA-7410-AS | Antisense | 1365-1389 (ERGA__CDS__07330) | 1962-1986 (ERWE__CDS__07410) |

These PCR products are listed in Table 13 below.

TABLE 13

| PCR-product | Sense-primer | Antisense-primer | Gene-detected | Strain |
|---|---|---|---|---|
| RFLP-ERGA-120 | P-WEGA-120-S | P-WEGA-120-AS | ERGA_CDS_00120 | Gardel |
| RFLP-ERWE-120 | P-WEGA-120-S | P-WEGA-120-AS | ERWE_CDS_00120 | Welgevonden |
| RFLP-ERGA-1350 | P-WEGA-1350-S | P-WEGA-1350-AS | ERGA-CDS_01350 | Gardel |
| RFLP-ERWE-1390 | P-WEGA-1350-S | P-WEGA-1350-AS | ERWE_CDS_01390 | Welgevonden |
| RFLP-ERGA-4500 | P-WEGA-4500-S | P-WEGA-4500-AS | ERGA_CDS_04500 | Gardel |
| RFLP-ERWE-4590/4600 | P-WEGA-4500-S | P-WEGA-4500-AS | ERWE_CDS_04590 ERWE_CDS_04600 | Welgevonden |
| RFLP-ERGA-5350 | P-WEGA-5350-S | P-WEGA-5350-AS | ERGA_CDS_05350 | Gardel |
| RFLP-ERWE-5460/5470 | P-WEGA-5350-S | P-WEGA-5350-AS | ERWE_CDS_05460 ERWE_CDS_05470 | Welgevonden |
| RFLP-ERGA-5740 | P-WEGA-5740-S | P-WEGA-5740-AS | ERGA_CDS_05740 | Gardel |
| RFLP-ERWE-5830 | P-WEGA-5740-S | P-WEGA-5740-AS | ERWE_CDS_05830 | Welgevonden |
| RFLP-ERGA-7330 | P-WEGA-7410-S | P-WEGA-7410-AS | ERGA_CDS_07330 | Gardel |
| RFLP-ERWE-7410 | P-WEGA-7410-S | P-WEGA-7410-AS | ERWE_CDS_07410 | Welgevonden |

RFLP Analysis

The PCR products are used for further RFLP analysis with the following restriction endonucleases: AluI, DraI, EcoRV, HinfI, RsaI and TaqI.

PCR products are digested in a final volume of 20 µl with the selected enzyme under the conditions, i.e. buffer, time and temperature, recommended by the supplier of the enzyme. Following digestion, the restriction fragments are separated on 2% agarose gel electrophoresis in Tris-borate-EDTA buffer.

The results are shown in Table 14 below.

TABLE 14

| PCR product | Number of sites for selected restriction enzymes | | | | | |
|---|---|---|---|---|---|---|
| | AluI | DraI | EcoRV | HinfI | RsaI | TaqI |
| RFLP-ERGA-120 | 4 | 2 | 4 | 11 | 8 | 4 |
| RFLP-ERWE-120 | 4 | 2 | 1 | 9 | 9 | 1 |
| RFLP-ERGA-1350 | 8 | 2 | 1 | 10 | 14 | 5 |
| RFLP-ERWE-1390 | 5 | 4 | 1 | 1 | 10 | 1 |
| RFLP-ERGA-4500 | 6 | 5 | 4 | 10 | 14 | 5 |
| RFLP-ERWE-4590/4600 | 5 | 9 | 1 | 8 | 8 | 6 |
| RFLP-ERGA-5350 | 5 | 2 | 2 | 6 | 13 | 2 |
| RFLP-ERWE-5460/5470 | 2 | 2 | 2 | 8 | 17 | 2 |
| RFLP-ERGA-5740 | 2 | 4 | 1 | 8 | 17 | 2 |
| RFLP-ERWE-5830 | 3 | 3 | 2 | 6 | 12 | 4 |
| RFLP-ERGA-7330 | 2 | 3 | 1 | 2 | 9 | 1 |
| RFLP-ERWE-7410 | 2 | 3 | 1 | 2 | 17 | 1 |

These results show that depending on the strain's DNA used as template for the PCR, all the PCR products yield a different number of bands for at least one of the tested restriction enzymes.

Example 10

Discrimination Between E. ruminantium Strain Gardel and E. ruminantium Strain Welgevonden Based on DNA Hybridization This example illustrates the use of the Mut oligonucleotide series described in Example 7 as labelled DNA probes to specifically discriminate E. ruminantium strain Gardel from E. ruminantium strain Welgevonden through DNA hybridization analysis.

The Mut oligonucleotides used as DNA probes are labelled with α-32P dCTP by random priming using the Rediprime II DNA labeling system (Amersham Bioscience) following the procedure described by the supplier. DNA concentration is adjusted so that 45 μl of DNA solution in TE buffer (10 mM Tris-HCl, pH 8.0) contains 25 ng of DNA. DNA is denatured by incubation at 100° C. for 5 min, followed by immediate incubation in ice-cold water for 5 min. The tube is briefly centrifuged to bring the contents to the bottom of the tube. Denatured DNA is transferred to the reaction tube provided in the kit and mixed to 5 μl of Redivue [32P] dCTP. Reaction is incubated at 37° C. for 10 min and stopped by addition of 5 μl of 0.2 m EDTA. The labelled probe is heat denatured by incubation at 100° C. for 5 min followed by incubation for 5 min in ice-cold water prior to hybridization with *E. ruminantium* DNA.

Total DNA from strain Gardel or from strain Welgevonden is obtained as described in Example 5.

Heat denatured DNA is spotted on a nylon membrane (Hybond N+, Amersham) using a slot blot manifold (Hoeffer Scientific Instruments) following the procedure recommended by the supplier of the membrane (Amersham). DNA-DNA hybridization is conducted as described in the Hybond N+ user manual. Prehybridization is conducted overnight in an hybridization tube (meant for use in hybridization ovens) and incubated at 68° C. with 20 ml of prehybridization buffer (Denhardt 5×, SSPE 2×, SDS 0.5×, SSPE-Dextran 4×, denatured hering-sperm DNA). After removal of the prehybridization buffer, the membrane is incubated overnight at 68° C. in 10 ml of hybridization buffer (Denhardt 5×, SSPE 2×, SDS 0.5×, SSPE-Dextran 4×, denatured hering-sperm DNA, 30 ng/ml of labelled DNA probe). Following hybridization, the membrane is washed successively for 30 min in 2×SSC, 0.5% SDS at room temperature and in 0.1×SSC, 0.5% SDS at 68° C.

Hybridized probes are revealed by autoradiography.

MutERWE 1390N1, MutERWE 1390N3, MutERWE 4590N1, MutERWE 4600N3, MutERWE 5460N1, and MutERWE 5470N3, hybridize with DNA from both strains Gardel and Welgevonden, while MutERWE 1390N2, MutERWE 4590N2, MutERWE 5460N2 only hybridize with DNA from strain Gardel.

TABLE 15A

| Oligonucleotide or Primer name | Orientation | Sequence (from 5' to 3') | SEQ ID NO |
|---|---|---|---|
| P-ERGA-4340-A | sense | atgagtcacagttttattgag | 21 |
| P-ERGA-4340-B | antisense | cactcaaaatcacaagaagta | 22 |
| P-ERGA-4980-A | sense | atgtatttagtctatttagtagctg | 23 |
| P-ERGA-4980-B | antisense | ataacatctaattgaacaatatc | 24 |
| P-ERGA-5590-A | sense | atgaaaggatctttatctgc | 25 |
| P-ERGA-5590-B | antisense | ccttcttcttcttcattatg | 26 |
| P-ERGA-5600-A | sense | aagaattacatgatgcagc | 27 |
| P-ERGA-5600-B | antisense | tcttctcttgttatactctctg | 28 |
| P-ERGA-7580-A | sense | atggatttaaataaactaataaa | 29 |
| P-ERGA-7580-B | antisense | gcattttctctacctacga | 30 |
| P-ERWE-8330-A | sense | gtctttatataaaagtaagaattga | 31 |
| P-ERWE-8330-B | antisense | tgctataagattgaactgaaa | 32 |
| Oligo-ERGA-4340 | sense | cactaattaacaatattacttcttgtgattttgagtgtaataaacaatga | 33 |
| Oligo-ERGA-4980 | sense | gttaaatttaatgtcagatatttgttcaattagatgttataatgttaaaagg | 34 |
| Oligo-ERGA-5590 | sense | aggtcgtggtcttgcttttttccatgatgttgcaagtaattttgaaacat | 35 |
| Oligo-ERGA-5600 | sense | gtaaacaagaggaaggattagaaacacatcagctttccaccaatgtagta | 36 |
| Oligo-ERGA-7580 | sense | ttgaggattttatgttctcagaacaaatcgtaggtagagaaaatgcagaa | 37 |
| Oligo-ERWE-8330 | sense | ttgatgattctactgatgttattacttataactctaaaaaaaatatgtgta | 38 |
| MutERWE-1390N1 | sense | tgatgttacagatagattgtatgtgatgtggcaattgagatatcataata | 39 |
| MutERWE-1390N2 | sense | tgtaataaagcctactcactatgtaacgcatgtaacattggaatcgaagt | 40 |
| MutERWE-1390N3 | sense | tttttaatttggatagtattcaaagtagtgtttctggtgtgcaagtgaca | 41 |
| MutERWE-4590N1 | sense | ttcctattaacatagaacatgctctatcaaatatagcaaatttaaatgca | 42 |
| MutERWE-4590N2 | sense | atctaataaatgcgtctgatctaataaatgcgtctgatctaataaaagaa | 43 |
| MutERWE-4600N3 | sense | tcatcaaaaagatacgttgtataggtaatactatagatcctgaacaagga | 44 |
| MutERWE-5460N1 | sense | tcttaaaagataaaaaatcaaagcttactgatcctagtgagatagcaaa | 45 |
| MutERWE-5460N2 | sense | gaacaagataaggtaggagaatttgaagtagctgaagatactagtgtaga | 46 |
| MutERWE-5470N3 | sense | gtgcttctgttccagatacaggacaagatatattacatagtaatgctgct | 47 |

TABLE 15B

| Oligonucleotide or Primer name | Orientation | Sequence (from 5' to 3') | SEQ ID NO |
|---|---|---|---|
| P-Z-1-ERGA-120 | sense | gtattgataattatgatggtgaaac | 48 |
| P-Z-2-ERGA-120-S | sense | gcacatgatatcgaacatgcagttc | 49 |
| P-Z-2-ERGA-120-AS | antisense | gaactgcatgttcgatatcatgtgc | 50 |
| P-Z-3-ERGA-120 | antisense | ggttacaaggacaatgatgagtgtg | 51 |
| P-Z-1-ERGA-1350 | sense | tccaccagagatgttatttgtaaag | 52 |
| P-Z-2-ERGA-1350-S | sense | cactatgtaacgcatgtaacattgg | 53 |
| P-Z-2-ERGA-1350-AS | antisense | ccaatgttacatgcgttacatagtg | 54 |
| P-Z-3-ERGA-1350 | antisense | caacagaactttcagtattaaaagc | 55 |
| P-Z-1-ERGA-4500 | sense | gttaagtgtgaaatgtattgtttag | 56 |
| P-Z-2-ERGA-4500-S | sense | cgtctgatctaataaatgcgtctga | 57 |
| P-Z-2-ERGA-4500-AS | antisense | tcagacgcatttattagatcagacg | 58 |
| P-Z-1/3-ERGA-4500-S | sense | ctagtaaggaaagaaaaacttaagc | 59 |
| P-Z-1/3-ERGA-4500-AS | antisense | gcttaagttttctttccttactag | 60 |
| P-Z-3-ERGA-4500 | antisense | cactttctgttaattcaaaagtaga | 61 |
| P-Z-1-ERGA-5350 | sense | gaattaattgatatgaatgcagaag | 62 |
| P-Z-2-ERGA-5350-S | sense | ggtaggagaatttgaagtagctgaag | 63 |
| P-Z-2-ERGA-5350-AS | antisense | cttcagctacttcaaattctcctacc | 64 |
| P-Z-3-ERGA-5350 | antisense | cttgtagattcttcttctgtgctac | 65 |
| P-Z-1-ERGA-5740 | sense | gtaggccaaaaagtataggtaatag | 66 |
| P-Z-2-ERGA-5740-S | sense | ttagaccaaaaacatttgcatctag | 67 |
| P-Z-2-ERGA-5740-AS | antisense | ctagatgcaaatgttttggtctaa | 68 |
| P-Z-3-ERGA-5740 | antisense | caacaaatacatcatcttcaagttg | 69 |
| P-Z-1-ERWE-7410 | sense | agggttacttattgtagtcagagtg | 70 |
| P-Z-2-ERWE-7410-S | sense | gagaagggatgttactgatacagcg | 71 |
| P-Z-2-ERWE-7410-AS | antisense | cgctgtatcagtaacatcccttctc | 72 |
| P-Z-3-ERWE-7410 | antisense | cctcttcgtatacaggattaccatt | 73 |
| P-WEGA-120-S | sense | atgggtattgataattatgatggtg | 74 |
| P-WEGA-120-AS | antisense | caaatgtaatttcatggttacaagg | 75 |
| P-WEGA-1350-S | sense | gcgatgttataactgttcaggtaa | 76 |
| P-WEGA-1350-AS | antisense | catgagatgtatatcttgtactcac | 77 |
| P-WEGA-4500-S | sense | gttaagtgtgaaatgtattgtttag | 78 |
| P-WEGA-4500-AS | antisense | ctaaatctttactttgagattatg | 79 |
| P-WEGA-5350-S | sense | atttatcagcgactgattattctag | 80 |
| P-WEGA-5350-AS | antisense | ctagtacacttgtagattcttcttc | 81 |

TABLE 15B-continued

| Oligonucleotide or Primer name | Orientation | Sequence (from 5' to 3') | SEQ ID NO |
|---|---|---|---|
| P-WEGA-5740-S | sense | cgtaatatatctttacaaaagttgacac | 82 |
| P-WEGA-5740-AS | antisense | ttcaacaaatacatcatcttcaagttga | 83 |
| P-WEGA-7410-S | sense | atgaatgagataatcctatacacag | 84 |
| P-WEGA-7410-AS | antisense | agtcacatcatattgactatgcaca | 85 |

The invention claimed is:

1. A method for discriminating between *Ehrlichia ruminantium* strain Gardel and *Ehrlichia ruminantium* strain Welgevonden, wherein said method comprises:
   providing a lysate or an isolated nucleic acid from *Ehrlichia ruminantium* strain Gardel and *Ehrlichia ruminantium* strain Welgevonden; and
   detecting the presence or the absence of the orphan gene ERGA_CDS 04980 having SEQ. ID NO: 2 in said lysate or said isolated nucleic acid.

2. The method of claim 1, which further comprises the detection of the presence or the absence, in said lysate or said isolated nucleic acid of at least one orphan gene selected among:
   ERGA_CDS 04340 (SEQ ID NO: 1)
   ERGA_CDS 05590 (SEQ ID NO: 3)
   ERGA_CDS 05600 (SEQ ID NO: 4)
   ERGA_CDS 07580 (SEQ ID NO: 5)
   ERWE_CDS 08330 (SEQ ID NO: 6).

3. The method of claim 1, which further comprises the detection, in said lysate or said isolated nucleic acid, of one of the members of at least one allelic couple of genes consisting of ERGA_CDS_01350 having the SEQ ID NO: 9 and ERWE_CDS_01390 having the sequence SEQ ID NO: 10.

4. The method of claim 2, which further comprises the detection, in said lysate or said isolated nucleic acid, of one of the members of at least one allelic couple of genes consisting of ERGA_CDS_01350 having the SEQ ID NO: 9 and ERWE_CDS_01390 having the sequence SEQ ID NO: 10.

5. The method of claim 3, which further comprises the detection, in said lysate or said isolated nucleic acid, of one of the members of at least one allelic couple of genes selected among:

a couple consisting of ERGA_CDS__00120 having the SEQ ID NO: 7 and ERWE_CDS__00120 having the SEQ ID NO: 8;

a couple consisting of ERG A_CDS__01350 having the SEQ ID NO: 9 and ERWE_CDS__01390 having the SEQ ID NO: 10;

a couple consisting of ERGA_CDS__05740 having the SEQ ID NO: 11 and ERWE_CDS__05830 having the SEQ ID NO: 12;

a couple consisting of ERGA_CDS__04500 having the SEQ ID NO: 13 and ERWE_CDS__04590 having the SEQ ID NO: 14+ERWE_CDS__04600 having the SEQ ID NO: 15;

a couple consisting of ERGA_CDS__05350 having the SEQ ID NO: 16 and ERWE_CDS__05460 having the SEQ ID NO: 17+ERWE_CDS__05470 having the SEQ ID NO: 18; and a couple consisting of ERGA_CDS__07330 having the SEQ ID NO: 19) and ERWE_CDS__07410 having the SEQ ID NO: 20.

6. The method of claim 4, which further comprises the detection, in said lysate or said isolated nucleic acid, of one of the members of at least one allelic couple of genes selected among:

a couple consisting of ERGA_CDS__00120 having the SEQ ID NO: 7 and ERWE_CDS__00120 having the SEQ ID NO: 8;

a couple consisting of ERG A_CDS__01350 having the SEQ ID NO: 9 and ERWE_CDS__01390 having the SEQ ID NO: 10;

a couple consisting of ERGA_CDS__05740 having the SEQ ID NO: 11 and ERWE_CDS__05830 having the SEQ ID NO: 12;

a couple consisting of ERGA_CDS__04500 having the SEQ ID NO: 13 and ERWE_CDS__04590 having the SEQ ID NO: 14+ERWE_CDS__04600 having the SEQ ID NO: 15;

a couple consisting of ERGA_CDS__05350 having the SEQ ID NO: 16 and ERWE_CDS__05460 having the SEQ ID NO: 17+ERWE_CDS__05470 having the SEQ ID NO: 18; and a couple consisting of ERGA_CDS__07330 having the SEQ ID NO: 19) and ERWE_CDS__07410 having the SEQ ID NO: 20.

* * * * *